(12) United States Patent
Chatterjee et al.

(10) Patent No.: US 10,398,608 B2
(45) Date of Patent: Sep. 3, 2019

(54) CHASSIS DESIGN FOR ABSORBENT ARTICLE

(71) Applicant: The Procter & Gamble Company, Cincinnati, OH (US)

(72) Inventors: Kumardipti Chatterjee, Indian Hill, OH (US); Jeromy Thomas Raycheck, South Lebanon, OH (US); Michael Devin Long, Springfield Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 581 days.

(21) Appl. No.: 15/186,820

(22) Filed: Jun. 20, 2016

(65) Prior Publication Data

US 2017/0000661 A1 Jan. 5, 2017

Related U.S. Application Data

(60) Provisional application No. 62/186,738, filed on Jun. 30, 2015.

(51) Int. Cl.
*A61F 13/49* (2006.01)
*A61F 13/494* (2006.01)
(Continued)

(52) U.S. Cl.
CPC ........ *A61F 13/49015* (2013.01); *A61F 13/49* (2013.01); *A61F 13/4906* (2013.01);
(Continued)

(58) Field of Classification Search
CPC .......... A61F 13/49012; A61F 13/49015; A61F 13/49017; A61F 13/4906; A61F 13/49413;
(Continued)

(56) References Cited

U.S. PATENT DOCUMENTS 3,848,594 A 11/1974 Buell
3,860,003 A 1/1975 Buell
(Continued)

FOREIGN PATENT DOCUMENTS

EP 0172036 2/1986
EP 1621168 2/2006
(Continued)

OTHER PUBLICATIONS

International Search Report, PCT/US2016/038368, dated Sep. 19, 2016, 12 pages.

*Primary Examiner* — Catharine L Anderson
(74) *Attorney, Agent, or Firm* — Wednesday G. Shipp

(57) ABSTRACT

A disposable absorbent article may include a first waist region, a second waist region, a crotch region disposed between the first and the second waist regions, and a chassis having a topsheet, backsheet, absorbent core, and chassis periphery. The chassis periphery has a varying width, $W_v$. The varying width $W_v$ has a first maximum width, $W_1$, in the first waist region, a minimum width, $W_{min}$, in the crotch region, and a second maximum width, $W_2$, in the second waist region, wherein $W_1$ is greater than $W_2$.

22 Claims, 22 Drawing Sheets

(51) Int. Cl.
*A61F 13/496* (2006.01)
*A61F 13/551* (2006.01)

(52) U.S. Cl.
CPC ...... *A61F 13/496* (2013.01); *A61F 13/49012* (2013.01); *A61F 13/49017* (2013.01); *A61F 13/49413* (2013.01); *A61F 13/55105* (2013.01); *A61F 2013/49082* (2013.01); *A61F 2013/49092* (2013.01)

(58) Field of Classification Search
CPC ...... A61F 13/58; A61F 13/622; A61F 13/625; A61F 2013/49028; A61F 2013/49068; A61F 2013/49074; A61F 2013/49076; A61F 2013/49077; A61F 2013/49082; A61F 2013/49092; A61F 2013/4944; A61F 2013/586; A61F 2013/587
See application file for complete search history.

(56) References Cited

U.S. PATENT DOCUMENTS

| | | | |
|---|---|---|---|
| 4,116,892 A | 9/1978 | Schwarz | |
| 4,319,572 A | 3/1982 | Widlund et al. | |
| 4,610,678 A | 9/1986 | Weisman et al. | |
| 4,662,875 A | 5/1987 | Hirotsu et al. | |
| 4,673,402 A | 6/1987 | Weisman et al. | |
| 4,695,278 A | 9/1987 | Lawson | |
| 4,699,622 A | 10/1987 | Toussant et al. | |
| 4,808,178 A | 2/1989 | Aziz | |
| 4,834,735 A | 5/1989 | Alemany et al. | |
| 4,834,741 A | 5/1989 | Sabee | |
| 4,846,815 A | 7/1989 | Scripps | |
| 4,888,231 A | 12/1989 | Angstadt | |
| 4,892,536 A | 1/1990 | DesMarais et al. | |
| 4,894,060 A | 1/1990 | Nestegard | |
| 4,909,803 A | 3/1990 | Aziz et al. | |
| 4,946,527 A | 8/1990 | Battrell | |
| 4,963,140 A | 10/1990 | Robertson et al. | |
| 4,990,147 A | 2/1991 | Freeland | |
| 5,037,416 A | 8/1991 | Allen et al. | |
| 5,137,537 A | 8/1992 | Herron et al. | |
| 5,143,679 A | 9/1992 | Weber et al. | |
| 5,147,345 A | 9/1992 | Young et al. | |
| 5,151,092 A | 9/1992 | Buell et al. | |
| 5,156,793 A | 10/1992 | Buell et al. | |
| 5,167,653 A | 12/1992 | Igaue et al. | |
| 5,167,897 A | 12/1992 | Weber et al. | |
| 5,221,274 A | 6/1993 | Buell et al. | |
| 5,242,436 A | 9/1993 | Weil et al. | |
| 5,260,345 A | 11/1993 | Desmarais et al. | |
| 5,269,775 A | 12/1993 | Freeland et al. | |
| 5,342,338 A | 8/1994 | Roe | |
| 5,387,207 A | 2/1995 | Dyer et al. | |
| 5,397,316 A | 3/1995 | Lavon et al. | |
| 5,422,172 A | 6/1995 | Ames et al. | |
| 5,499,978 A | 3/1996 | Buell et al. | |
| 5,507,736 A | 4/1996 | Clear et al. | |
| 5,518,801 A | 5/1996 | Chappell et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,575,783 A * | 11/1996 | Clear | A61F 13/49009 604/385.22 |
| 5,580,411 A | 12/1996 | Nease et al. | |
| 5,591,152 A | 1/1997 | Buell et al. | |
| 5,607,416 A | 3/1997 | Yamamoto et al. | |
| 5,607,760 A | 3/1997 | Roe | |
| 5,609,587 A | 3/1997 | Roe | |
| 5,625,222 A | 4/1997 | Yoneda et al. | |
| 5,635,191 A | 6/1997 | Roe et al. | |
| 5,643,588 A | 7/1997 | Roe et al. | |
| 5,667,609 A * | 9/1997 | Liu | A61F 13/494 156/290 |
| 5,827,259 A | 10/1998 | Laux et al. | |
| 5,865,823 A | 2/1999 | Curro | |
| 5,938,652 A | 8/1999 | Sauer | |
| 5,993,433 A * | 11/1999 | St. Louis | A61F 13/4942 604/385.27 |
| 6,004,306 A | 12/1999 | Robles et al. | |
| 6,107,537 A | 8/2000 | Elder et al. | |
| 6,120,487 A | 9/2000 | Ashton | |
| 6,123,694 A | 9/2000 | Pieniak et al. | |
| 6,156,023 A | 12/2000 | Yoshioka et al. | |
| 6,325,786 B1 * | 12/2001 | Bjorklund | A61F 13/49 604/358 |
| 6,432,098 B1 | 8/2002 | Kline et al. | |
| 6,511,465 B1 * | 1/2003 | Freiburger | A61F 13/15203 604/385.01 |
| 6,607,515 B2 | 8/2003 | Glaug et al. | |
| 6,682,515 B1 | 1/2004 | Mizutani et al. | |
| 6,706,030 B1 | 3/2004 | Okuda et al. | |
| 6,740,071 B2 * | 5/2004 | Gibbs | A61F 13/5622 604/389 |
| 7,163,530 B1 | 1/2007 | Toyoshima et al. | |
| 7,462,174 B2 | 12/2008 | Nishitani et al. | |
| 7,626,073 B2 | 12/2009 | Catalan | |
| 8,475,423 B2 | 7/2013 | Datta et al. | |
| 8,568,382 B2 * | 10/2013 | Kline | A61F 13/49011 604/385.22 |
| 9,023,007 B2 | 5/2015 | Hashino et al. | |
| 2003/0088225 A1 | 5/2003 | Glaug et al. | |
| 2004/0181200 A1 | 9/2004 | Desai et al. | |
| 2004/0193133 A1 | 9/2004 | Desai et al. | |
| 2006/0069379 A1 | 3/2006 | VanGompel et al. | |
| 2007/0142798 A1 | 6/2007 | Goodlander et al. | |
| 2010/0082006 A1 | 4/2010 | Rogone et al. | |
| 2011/0196327 A1 | 8/2011 | Chhabra et al. | |
| 2011/0247199 A1 | 10/2011 | LaVon et al. | |
| 2013/0197463 A1 | 8/2013 | Malowaniec | |
| 2014/0000070 A1 | 1/2014 | Ashraf et al. | |
| 2014/0144579 A1 | 5/2014 | Brown et al. | |
| 2014/0148323 A1 | 5/2014 | Brown et al. | |
| 2014/0148773 A1 | 5/2014 | Brown et al. | |
| 2014/0148774 A1 | 5/2014 | Brown et al. | |
| 2014/0171897 A1 | 6/2014 | Roe et al. | |
| 2015/0025490 A1 | 1/2015 | Sakaguchi et al. | |
| 2015/0065983 A1 | 3/2015 | Sakaguchi et al. | |
| 2015/0305948 A1 | 10/2015 | Sakaguchi | |
| 2016/0113823 A1 | 4/2016 | Iwasaki | |

FOREIGN PATENT DOCUMENTS

| | | |
|---|---|---|
| FR | 2862868 | 6/2005 |
| JP | 05015933 U | 3/1993 |
| JP | 05317364 | 12/1993 |
| JP | 06075443 U | 10/1994 |
| JP | 08071106 | 3/1996 |
| JP | 10243961 | 9/1998 |
| JP | 11047189 | 2/1999 |
| JP | 2000288025 | 10/2000 |
| JP | 2001025485 | 1/2001 |
| JP | 2001095841 | 4/2001 |
| JP | 2001095844 | 4/2001 |
| JP | 2001293031 | 10/2001 |
| JP | 2003180736 | 7/2003 |
| JP | 2004041310 | 2/2004 |
| JP | 2004181253 | 7/2004 |
| JP | 2005111212 | 4/2005 |
| JP | 2006223881 | 8/2006 |
| JP | 2007143697 | 6/2007 |
| JP | 2008307223 | 12/2008 |
| JP | 2012200365 | 10/2012 |
| JP | 2012200366 | 10/2012 |
| WO | WO 95/16746 | 6/1995 |
| WO | WO 2004/80359 | 9/2004 |
| WO | WO 2005/095700 | 10/2005 |
| WO | WO 2005/110731 | 11/2005 |
| WO | WO 2007/069226 | 6/2007 |
| WO | WO 2011/024542 | 3/2011 |
| WO | WO 2012/003965 | 1/2012 |
| WO | WO 2013/089186 | 6/2013 |
| WO | WO 2013/147058 | 10/2013 |

(56) References Cited

FOREIGN PATENT DOCUMENTS

| WO | WO 2013/161952 | 10/2013 |
| WO | WO 2013/161956 | 10/2013 |
| WO | WO 2014/005043 | 1/2014 |
| WO | WO 2014/084230 | 6/2014 |
| WO | WO 2014/084236 | 6/2014 |

* cited by examiner

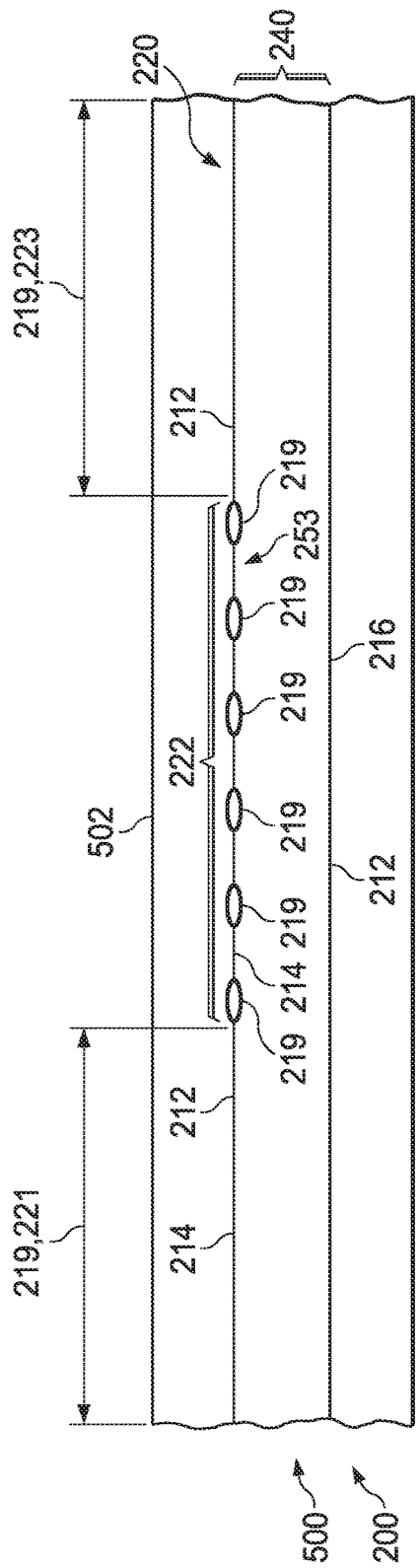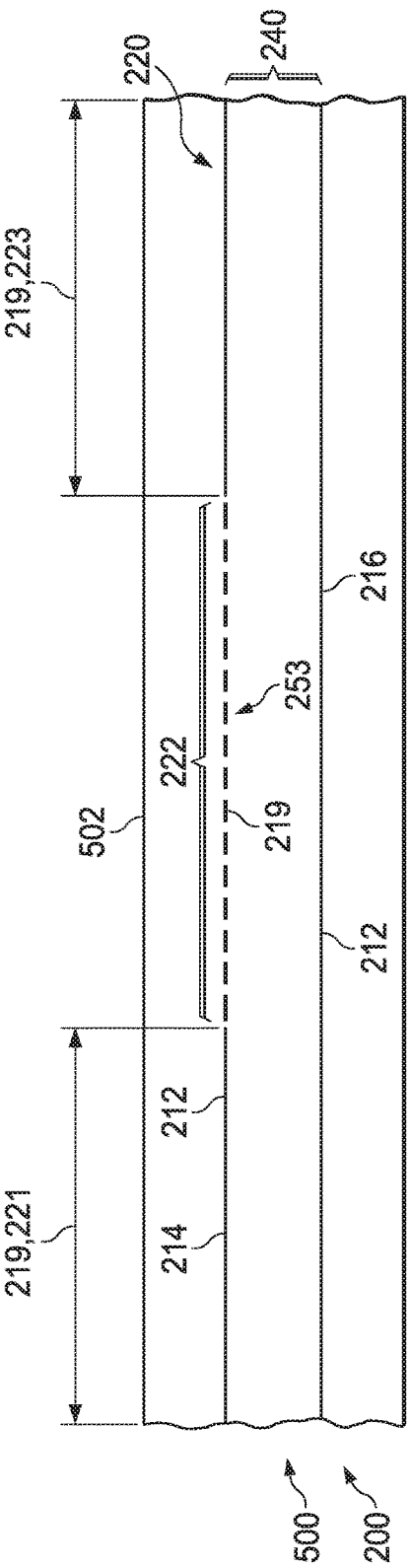

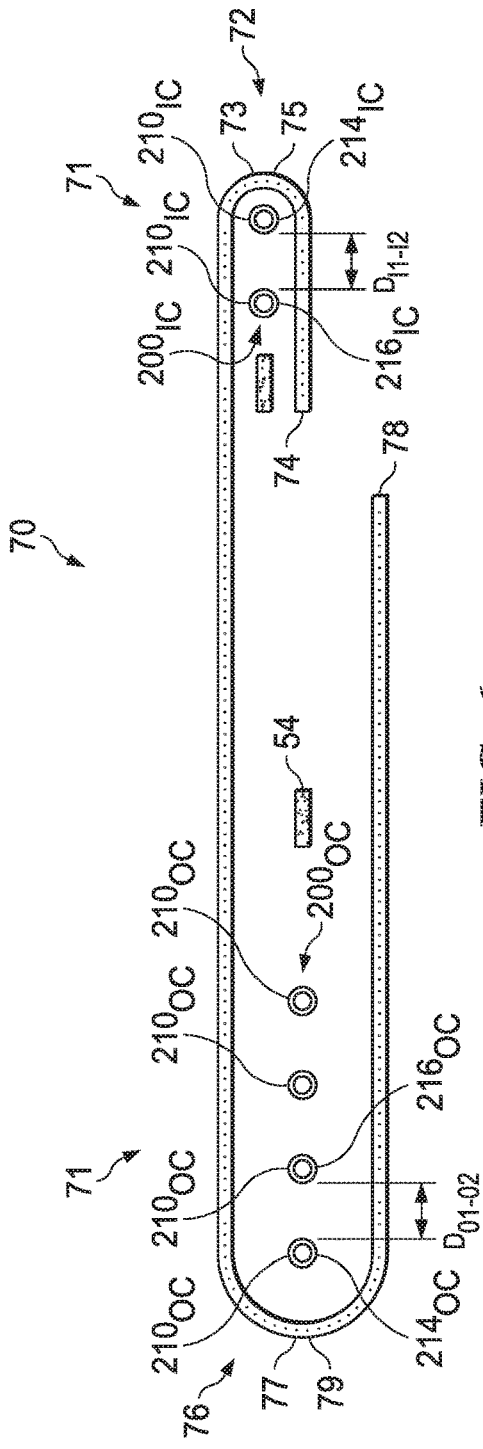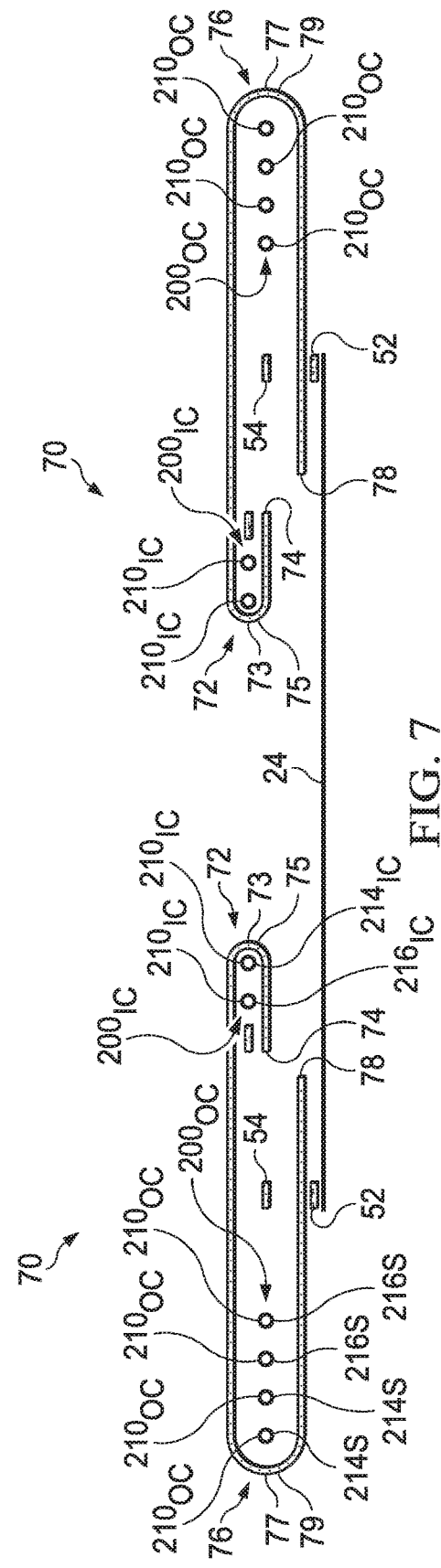
FIG. 6
FIG. 7

CHASSIS DESIGN FOR ABSORBENT ARTICLE

FIELD OF THE INVENTION

This invention relates to absorbent articles (e.g., diapers, adult incontinence articles, feminine hygiene pads) having improved structural design of elasticized regions and/or the chassis to provide enhanced comfort and/or ease of use while maintaining fit.

BACKGROUND OF THE INVENTION

It has long been known that absorbent articles such as conventional absorbent articles (e.g., diapers, adult incontinence articles, feminine hygiene pads) offer the benefit of receiving and containing urine and/or other bodily exudates (e.g., feces, menses, mixture of feces and urine, mixture of menses and urine, etc.). To effectively contain bodily exudates, the article should provide a snug fit around the waist and legs of a wearer.

Manufacturers often use the shape of an article and/or elasticized areas within the article to help achieve a snug fit. However, to date, manufacturers have not designed a shape that provides a sufficiently wide front waist region and permits the optimal utilization of side ear panels, while maintaining fit and garment-like appearance. Moreover, the tight contact provided by elastics can lead to skin irritation and discomfort. Further, the contraction of elastics may preclude an article from lying flat during application and may create defects such as wrinkles or gaps in areas of the article.

Accordingly, there is a need to provide an absorbent article that balances fit and/or containment of exudates with comfort and/or ease of application. Further, there is a continued need to provide signals to the consumer and/or wearer that the absorbent article will perform as desired.

SUMMARY OF THE INVENTION

In an embodiment, a disposable absorbent article for wearing about the lower torso of a wearer includes a first waist region having a first waist edge, a second waist region having a second waist edge, a crotch region disposed between the first and second waist regions; and a first longitudinal edge and a second longitudinal edge and a longitudinal centerline. The article also includes a chassis comprising a topsheet, a backsheet, and an absorbent core disposed between the topsheet and backsheet; and a back ear joined to the chassis in the second waist region. The first longitudinal edge, second longitudinal edge, first waist edge and second waist edge define a chassis periphery, and the chassis periphery has a varying width, $W_v$. The varying width $W_v$ has a first maximum width, $W_1$, in the first waist region, a minimum width, $W_{min}$, in the crotch region, and a second maximum width, $W_2$, in the second waist region. The first maximum width, $W_1$, is greater than the second maximum width, $W_2$.

In a further embodiment, a disposable absorbent article for wearing about the lower torso includes a first waist region having a first waist edge, a second waist region having a second waist edge, a crotch region disposed between the first and second waist regions and a first longitudinal edge and a second longitudinal edge; and a longitudinal centerline. The article also includes a chassis comprising a topsheet, a backsheet, and an absorbent core disposed between the topsheet and backsheet. The first longitudinal edge, second longitudinal edge, first waist edge and second waist edge define a chassis periphery, and the chassis periphery has a varying width, $W_v$. The varying width $W_v$ has a first maximum width, $W_1$, in the first waist region, a minimum width, $W_{min}$, in the crotch region, and a second maximum width, $W_2$, in the second waist region. The first maximum width, $W_1$, is greater than the second maximum width, $W_2$. The article further includes an elasticized component joined to the chassis and having an elasticized region.

In another embodiment, a disposable absorbent article for wearing about the lower torso of a wearer includes a first waist region having a first waist edge, a second waist region having a second waist edge, a crotch region disposed between the first and second waist regions; and a first longitudinal edge and a second longitudinal edge, and a longitudinal centerline. The article also includes a chassis comprising a topsheet, a backsheet, and an absorbent core disposed between the topsheet and backsheet. The first longitudinal edge, second longitudinal edge, first waist edge and second waist edge define a chassis periphery that has an hour-glass shape. The article also includes a discrete ear joined to a garment-facing side of the chassis in the second waist region, wherein the discrete ear has a fastener having an inboard fastener edge. A minimum lateral distance between the inboard fastener edge and the chassis periphery, $D_{LE-FE}$, is from about 0 mm to about 40 mm such that the chassis periphery is coterminous with or inboard of the inboard fastener edge at the minimum lateral distance.

BRIEF DESCRIPTION OF THE DRAWINGS

FIGS. 4D-4E are schematic plan views of exemplary embodiments of elasticized components as detailed herein. The elasticized components are shown in a flat, uncontracted state.

FIG. 6 is a schematic cross-sectional view of an exemplary embodiment of one of the leg gasketing systems of FIG. 1, taken along the lateral centerline. The leg gasketing system is shown in a flat, uncontracted state.

FIG. 7 is a schematic cross-sectional view of an exemplary embodiment of the leg gasketing systems and topsheet of FIG. 1, the cross section taken along the lateral centerline. The leg gasketing systems are shown in a flat, uncontracted state.

DETAILED DESCRIPTION OF THE INVENTION

Definitions

Figure 1:
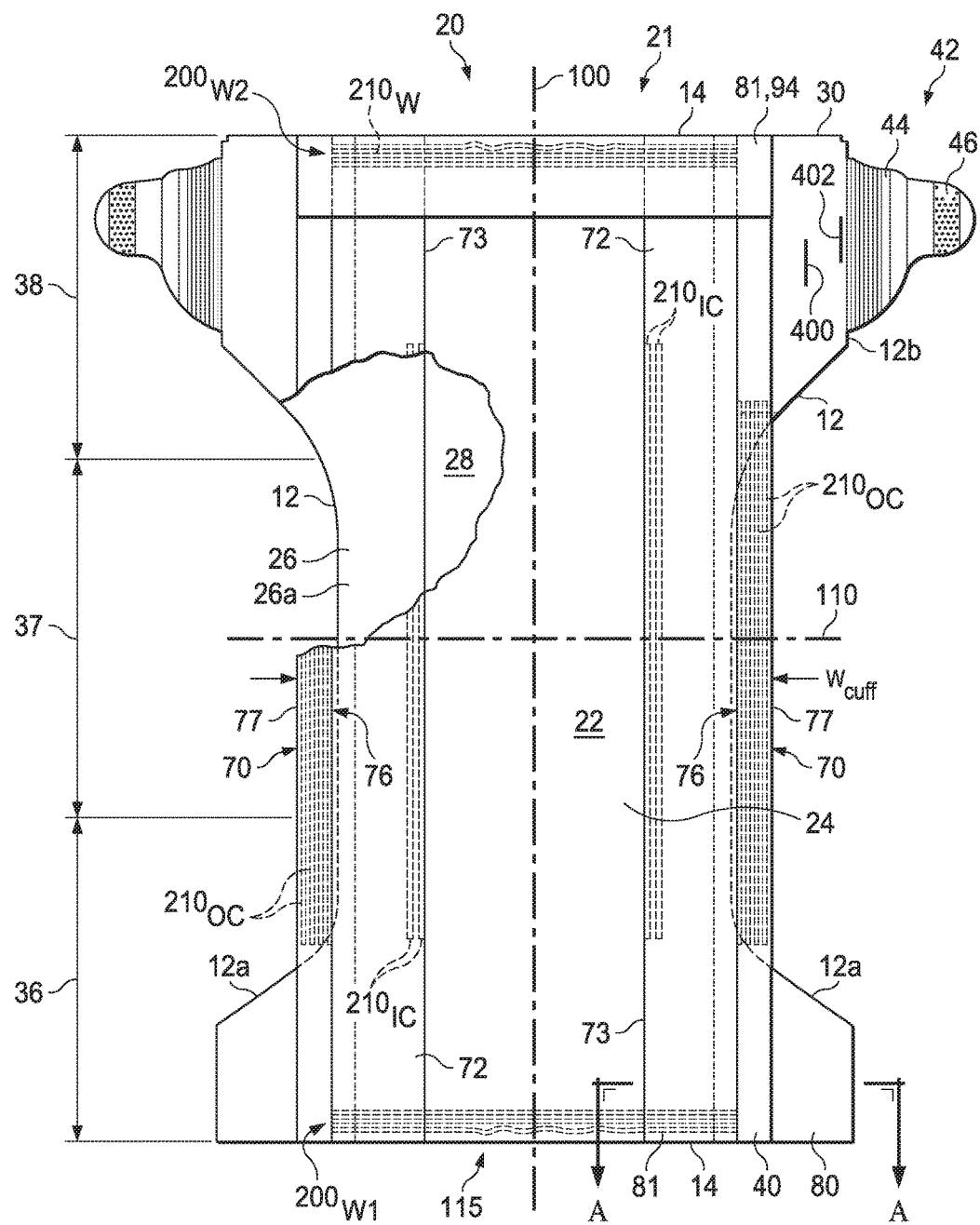
FIG. 1 is a schematic plan view of an exemplary embodiment of an absorbent article as detailed herein. The absorbent article is shown in a flat, uncontracted state.

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Proximal" and "Distal" refer respectively to the location of an element relatively near to or far from the longitudinal or lateral centerline of a structure (e.g., the proximal edge of a longitudinally extending element is located nearer to the longitudinal centerline than the distal edge of the same element is located relative to the same longitudinal centerline).

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal." Longitudinal distances are measured between points disposed along the same longitudinal line.

"Lateral" refers to a direction running from a longitudinal edge to an opposing longitudinal edge of the article and generally at a right angle to the longitudinal direction. Directions within 45 degrees of the lateral direction are considered to be "lateral." Lateral distances are measured between points disposed along the same lateral line.

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable."

"Elongatable," "extensible," or "stretchable" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery). Elastomeric materials may include elastomeric films (including but not limited to films derived from rubber and/or other polymeric materials), polyurethane films, elastomeric foams, scrims, elastic nonwovens, synthetic fibers such as LYCRA® and other sheet-like structures. An elastic member comprises elastomeric material.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

"Adjacent" as it refers to elastic members or sets of elastic members herein means that there are no elastic members disposed between said adjacent elastic members or between said adjacent sets of elastic members.

Overview

The present invention is directed to a disposable absorbent article with features that improve comfort, fit, ease of use and/or appearance. In embodiments, the chassis may comprise a maximum width in the front waist region, such that the front waist region is wider than the remaining portions of the article. In further embodiments, the article comprises an elasticized region having two elastic members proximate to one another and comprising different properties, such as different strain levels, different attachment patterns, and/or different contraction region lengths and/or attachment starting points and/or ending points positioned on different axes. In a further embodiment, the article comprises an array of elastic members in a waist region, wherein the elastic members are selected such that their relative contractive forces and/or relative moments of force compensate for changes in stiffness and/or bendability of surrounding materials in the article.

Absorbent Article

FIG. 1 is a plan view of an exemplary, non-limiting embodiment of an absorbent article 20 of the present invention in a flat, uncontracted state. The body-facing surface 115 of the absorbent article 20 is facing the viewer. The absorbent article 20 includes a longitudinal centerline 100 and a lateral centerline 110. The absorbent article 20 comprises a chassis 22. The absorbent article 20 and chassis 22 are shown to have a first waist region 36, a second waist region 38 opposed to the first waist region 36, and a crotch region 37 located between the first waist region 36 and the second waist region 38. The waist regions 36 and 38 generally comprise those portions of the absorbent article 20 which, when worn, encircle the waist of the wearer. The waist regions 36 and 38 may include elastic members $210_w$ such that they gather about the waist of the wearer to provide improved fit and containment. The crotch region 37 is the portion of the absorbent article 20 which, when the absorbent article 20 is worn, is generally positioned between the legs of the wearer.

The chassis 22 may comprise a liquid permeable topsheet 24, a backsheet 26, and an absorbent core 28 between the topsheet 24 and the backsheet 26. In embodiments that include one or more opacity strengthening patches 80, the chassis 22 also comprises the opacity strengthening patch(es) 80. The absorbent core 28 may have a body-facing surface and a garment-facing surface. The backsheet 26 may have a body-facing side 26a and a garment-facing side 26b. The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. In some embodiments, an acquisition-distribution system is disposed between the topsheet 26 and the absorbent core 28.

In certain embodiments, the chassis 22 comprises the main structure of the absorbent article 20 with other features added to form the composite absorbent article structure. While the topsheet 24, the backsheet 26, and the absorbent core 28 may be assembled in a variety of well-known configurations, absorbent article configurations are described generally in U.S. Pat. Nos. 3,860,003; 5,151,092; 5,221,274; 5,554,145; 5,569,234; 5,580,411; and 6,004,306.

Topsheet:

The topsheet 24 is generally a portion of the absorbent article 20 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is generally supple, soft feeling, and non-irritating to a wearer's skin. Generally, at least a portion of the topsheet 24 is liquid pervious, permitting liquid to readily penetrate through the thickness of the topsheet 24. One topsheet 24 useful herein is available from BBA Fiberweb, Brentwood, Tenn. as supplier code 055SLPV09U. The topsheet 24 may be apertured.

Any portion of the topsheet 24 may be coated with a lotion or skin care composition as is known in the art. Non-limiting examples of suitable lotions include those described in U.S. Pat. Nos. 5,607,760; 5,609,587; 5,635,191; and 5,643,588. The specific examples are not limiting, as any lotion or skin care composition known in the art may be utilized. The topsheet 24 may be fully or partially elasticized or may be foreshortened so as to provide a void space between the topsheet 24 and the core 28. Exemplary structures including elasticized or foreshortened topsheets are described in more detail in U.S. Pat. Nos. 4,892,536; 4,990,147; 5,037,416; and 5,269,775.

Absorbent Core:

The absorbent core 28 may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. In one embodiment, at least a portion of the absorbent core is substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material does not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The amount of absorbent material, such as absorbent particulate polymer material present in the absorbent core may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. In some embodiments, the absorbent core may comprise one or more channels, wherein said channels are substantially free of absorbent particulate polymer material. The channels may extend longitudinally or laterally. The absorbent core may further comprise two or more channels. In one nonlimiting example, two channels are symmetrically disposed about the longitudinal axis.

Exemplary absorbent structures for use as the absorbent core 28 are described in U.S. Pat. Nos. 4,610,678; 4,673, 402; 4,834,735; 4,888,231; 5,137,537; 5,147,345; 5,342, 338; 5,260,345; 5,387,207; 5,397,316; and 5,625,222.

Backsheet:

The backsheet 26 is generally positioned such that it may be at least a portion of the garment-facing surface 120 of the absorbent article 20. Backsheet 26 may be designed to prevent the exudates absorbed by and contained within the absorbent article 20 from soiling articles that may contact the absorbent article 20, such as bed sheets and undergarments. In certain embodiments, the backsheet 26 is substantially water-impermeable. Suitable backsheet 26 materials include films such as those manufactured by Tredegar Industries Inc. of Terre Haute, Ind. and sold under the trade names X15306, X10962, and X10964. Other suitable backsheet 26 materials may include breathable materials that permit vapors to escape from the absorbent article 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 26 including, but not limited to, surface treatments, particular film selections and processing, particular filament selections and processing, etc.

Backsheet 26 may also consist of more than one layer. The backsheet 26 may comprise an outer cover and an inner layer. The outer cover may be made of a soft, non-woven material. The inner layer may be made of a substantially liquid-impermeable film, such as a polymeric film. The outer cover and an inner layer may be joined together by adhesive or any other suitable material or method. A particularly suitable outer cover is available from Corovin GmbH, Peine, Germany as supplier code A18AH0, and a particularly suitable inner layer is available from RKW Gronau GmbH, Gronau, Germany as supplier code PGBR4WPR. While a variety of backsheet configurations are contemplated herein, it would be obvious to those skilled in the art that various other changes and modifications can be made without departing from the spirit and scope of the invention.

Ears/Fasteners:

The absorbent article 20 may include front ears 40 and/or back ears 42. The ears 40, 42 may be extensible, inextensible, elastic, or inelastic. The ears 40, 42 may be formed from nonwoven webs, woven webs, knitted fabrics, polymeric and elastomeric films, apertured films, sponges, foams, scrims, and combinations and laminates thereof. In some embodiments, the ear 40, 42 may include elastomers (e.g., elastic strands, LYCRA® fibers), such that the ear is stretchable. In certain embodiments, the ears 40, 42 may be formed of a stretch laminate such as a nonwoven/elastomeric material laminate or a nonwoven/elastomeric material/nonwoven laminate, which also results in the ear being stretchable. Stretch laminates may be formed by any method known in the art. For example, the ears 40, 42 may be formed as a zero strain stretch laminate, which includes at least a layer of non-woven material and an elastomeric element. The elastomeric element is attached to the layer of non-woven material while in a relaxed or substantially relaxed state, and the resulting laminate is made stretchable (or more stretchable over a further range) by subjecting the laminate to an activation process which elongates the nonwoven layer permanently, but the elastomeric element temporarily. The nonwoven layer may be integral with at least a portion of the chassis 22, in which case the elastomeric element may be attached to the nonwoven layer and the non-woven/elastomeric element laminate is subsequently activated. Alternatively, the nonwoven layer may be a separate component, in which case the elastomeric element is attached to the nonwoven layer to form the laminate, which is then coupled to the main portion. If one or more layers of the ear 40, 42 are provided separately, the laminate may be activated either before or after attachment to the main portion. Zero strain activation processes are further disclosed in U.S. Pat. Nos. 5,167,897 and 5,156,793. A suitable elastic ear may be an activated laminate comprising an elastomeric film (such as is available from Tredegar Corp, Richmond, Va., as supplier code X25007) disposed between two nonwoven layers (such as is available from BBA Fiberweb, Brentwood, Tenn. as supplier code FPN332).

An ear 40, 42 may be highly extensible wherein the ear 40, 42 is capable of extending up to 150%. It is believed that highly extensible ears 40, 42 allow an absorbent article 20 to expand to comfortably fit a range of wearers who vary in shape and/or weight. Suitable highly extensible ears 40, 42 are described in U.S. Pat. Nos. 4,116,892, 4,834,741, 5,143, 679; 5,156,793; 5,167,897; and U.S. Pat. Nos. 5,422,172; and 5,518,801; PCT App. No. WO 2005/110731; and U.S. App. Nos. US 2004/0181200 and US 2004/0193133.

In an embodiment, the ears 40, 42 may be discrete. A discrete ear is formed as separate element which is joined to the chassis 22.

The absorbent article 20 may also include a fastening system 44. When fastened, the fastening system 44 interconnects the first waist region 36 and the rear waist region 38 resulting in a waist circumference that may encircle the wearer during wear of the absorbent article 20. The fastening system 44 may comprise a fastener 46 such as tape tabs, hook and loop fastening components, interlocking fasteners such as tabs & slots, buckles, buttons, snaps, and/or hermaphroditic fastening components, although any other known fastening means are generally acceptable. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system 44 may also provide a means for holding the article in a disposal configuration as disclosed in U.S. Pat. No. 4,963,140. The fastening system 44 may also include primary and secondary fastening systems, as disclosed in U.S. Pat. No. 4,699,622. The fastening system 44 may be constructed to reduce shifting of overlapped portions or to improve fit as disclosed in U.S. Pat. Nos. 5,242,436; 5,499,978; 5,507,736; and 5,591,152. In some embodiments, the fastening system 44 and/or the fastener 46 is foldable.

The fastening system 44 may be joined to any suitable portion of the article 20 by any suitable means. In some embodiments, the fastening system is joined to the ear 40, 42. In one nonlimiting example, the fastening system 44 and/or the fastener 46 is mechanically bonded to the ear 40, 42 through one or more mechanical bonds. In one nonlimiting example, the ear 40, 42 comprises a first fastener bond 400 disposed inboard and a second fastener bond 402 disposed outboard as shown in FIG. 1. The first and/or second fastener bond 400, 402 may be mechanical.

Figure 1A:
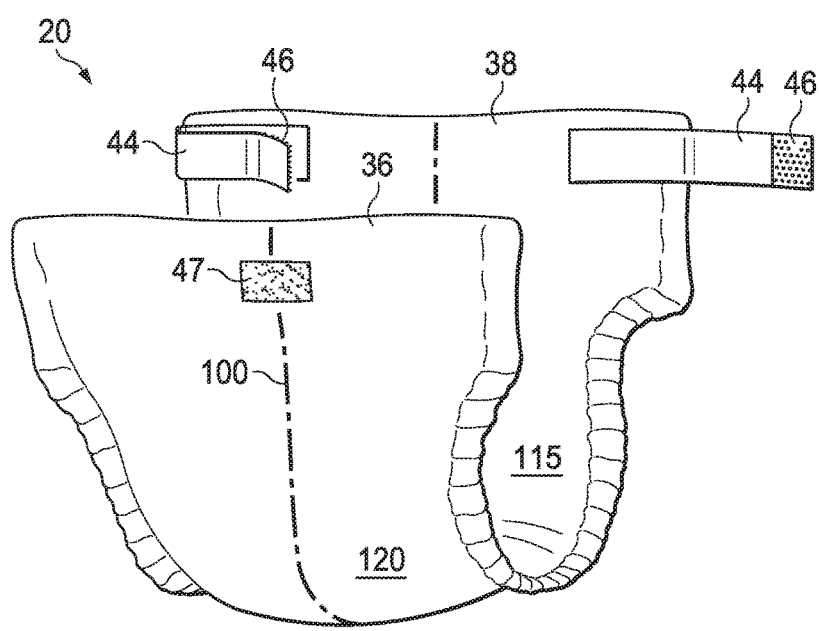
FIG. 1A is a schematic perspective view of an exemplary embodiment of an absorbent article as detailed herein.

The article 20 may comprise a landing zone 47 disposed in the first waist region 36 (as shown in FIG. 1A). The fastener 46 may attach to the first waist region 36 in the landing zone 47, or the fastening system 44 may be otherwise capable of joining the waist regions by connecting at the landing zone 47. In one nonlimiting example, the landing zone 47 is partially disposed on the longitudinal centerline 100. In another nonlimiting example, the landing zone 47 is disposed about 2 mm or less from the longitudinal centerline 100, or about 1 mm or less from the longitudinal centerline 100. The landing zone may comprise fastening components (e.g., mechanical closure elements comprising hook and loop fastening materials, adhesive, or other known means).

Chassis Design

The outer periphery 30 of the chassis 22 is defined by longitudinal edges 12 and waist edges (first waist edge 13 in first waist region 36 and second waist edge 14 in second waist region 38). The longitudinal edges 12 may be subdivided into a front longitudinal edge 12a, which is the portion of the longitudinal edge 12 in the first waist region 36, and a rear longitudinal edge 12b, which is the portion of the longitudinal edge 12 in the rear waist region 38. The chassis 22 may have opposing longitudinal edges 12 that are oriented generally parallel to the longitudinal centerline 100. However, for better fit, longitudinal edges 12 may be curved or angled to produce, for example, an "hourglass" shape article 21 when viewed in a plan view as shown in FIGS. 1-3A, for example. The chassis 22 may have opposing lateral edges 13, 14 (i.e., the first waist edge 13 and second waist edge 14) that are oriented generally parallel to the lateral centerline 110.

Figure 2:
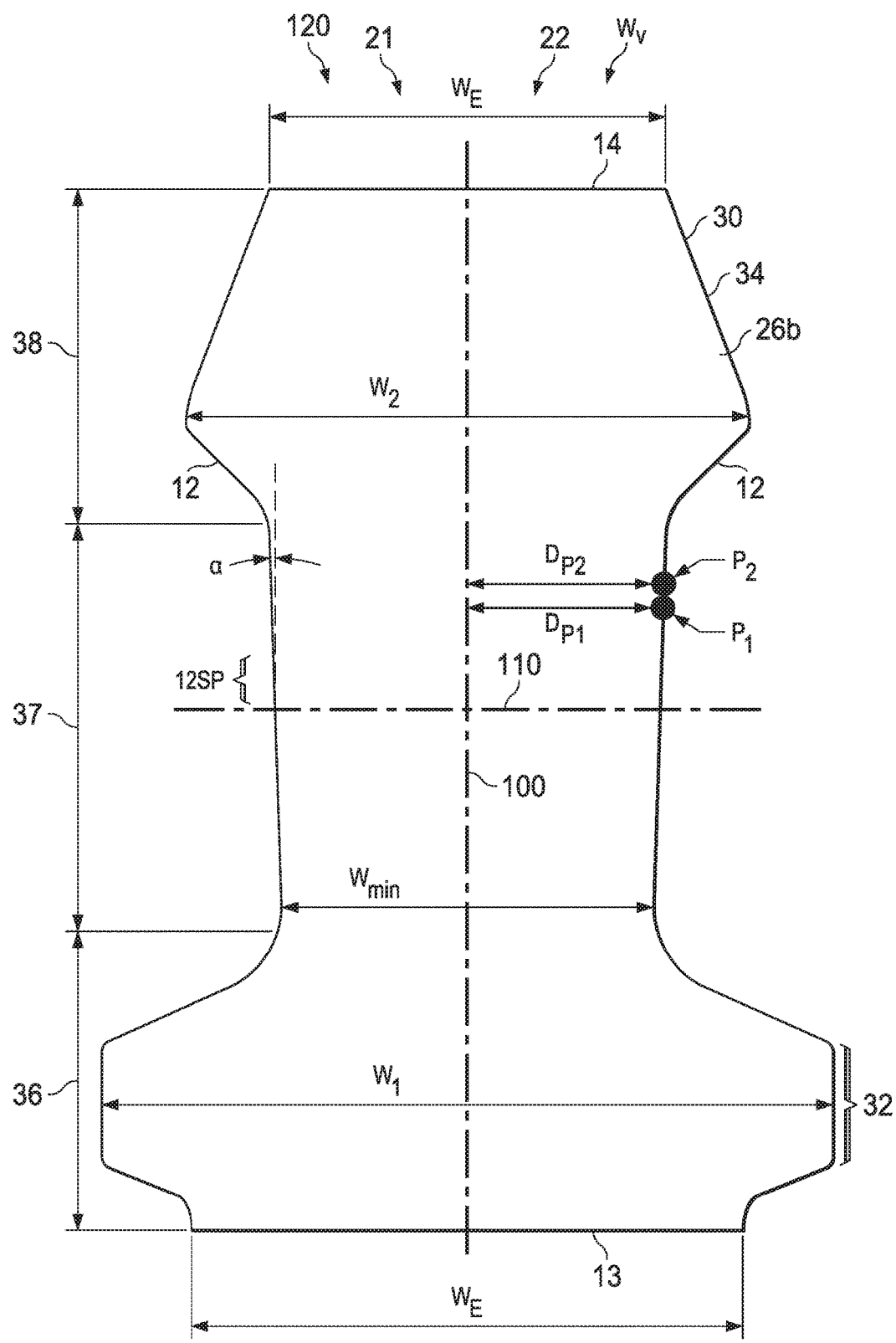
FIG. 2 is a schematic plan view of a chassis in accordance with one embodiment of the present invention.

In an embodiment depicted in FIG. 2, the chassis periphery 30 comprises a varying width, $W_v$. (FIG. 2 is a schematic view of the chassis with the garment-facing side 120 facing the viewer.) The varying width, $W_v$, may comprise multiple zones having different widths between the longitudinal edges 12. In one nonlimiting example, the chassis periphery comprises a first maximum width zone 32 disposed in the first waist region 36. The first maximum width zone 32 is a section in the first waist region 36 having a first maximum width, $W_1$, extending between the longitudinal edges 12 in the first waist region 36. The first maximum width, $W_1$, is the largest width dimension in the chassis periphery 30. The first maximum width, $W_1$, may be from about 150 mm to about 400 mm, or from 200 mm to about 380 mm, or from about 250 mm to about 360 mm, reciting for each range every 10 mm interval therebetween. In a further nonlimiting example, the chassis periphery 30 comprises a minimum width, $W_{min}$, disposed in the crotch region 37. The minimum width, $W_{min}$, is the smallest width dimension in the chassis periphery 30. The minimum width, $W_{min}$, may be from about 90 mm to about 180 mm, from about 100 mm to about 175 mm, or from about 140 mm to about 170 mm, reciting for each range every 10 mm interval therebetween. The chassis periphery 30 may further comprise a first maximum width to minimum width ratio, $W_1:W_{min}$, of from about 1.4 to about 2.7, or from about 1.6 to about 2.4, or from about 1.8 to about 2.2, reciting for each range every 0.1 interval therebetween.

In another nonlimiting example, the chassis periphery 30 comprises a second maximum width, $W_2$, disposed in the second waist region 38. The second maximum width, $W_2$, is the maximum width between the longitudinal edges 12 in the second waist region 38. The second maximum width, $W_2$, may be less than the first maximum width, $W_1$. The chassis periphery 30 may further comprise a first maximum width to second maximum width ratio, $W_1:W_2$ of from about 1.1 to about 1.7, reciting for said range every 0.1 interval therebetween.

To date, manufacturers have made taped diaper chassis with symmetric front and back waist regions or with back waist regions that have a greater maximum width than the maximum width of the front region. However, various benefits may be achieved by providing a wider first waist region 36, such as (i) the wide front may cover more skin around the front and side waist regions, signaling comfort and proper fit; (ii) rough fastening elements may be prevented from directly contacting the skin, thereby reducing skin irritation and abrasion; and/or (iii) the front waist region may be easier to find and grasp, reducing the time and effort required to apply an absorbent article. Further, sufficient overlap of the front waist region 36 and back waist region 38 around the wearer's waist can improve fit, reducing sagging and gapping about the waist and legs. In addition, sufficient overlap of these regions 36, 38 may increase the garment-like appearance of the article 20 during use.

In an embodiment, the width of a waist edge, $W_E$, is less than the first maximum width, $W_1$. In one nonlimiting example, both waist edges, 13, 14 comprise the same waist width, $W_E$.

Figure 3A:
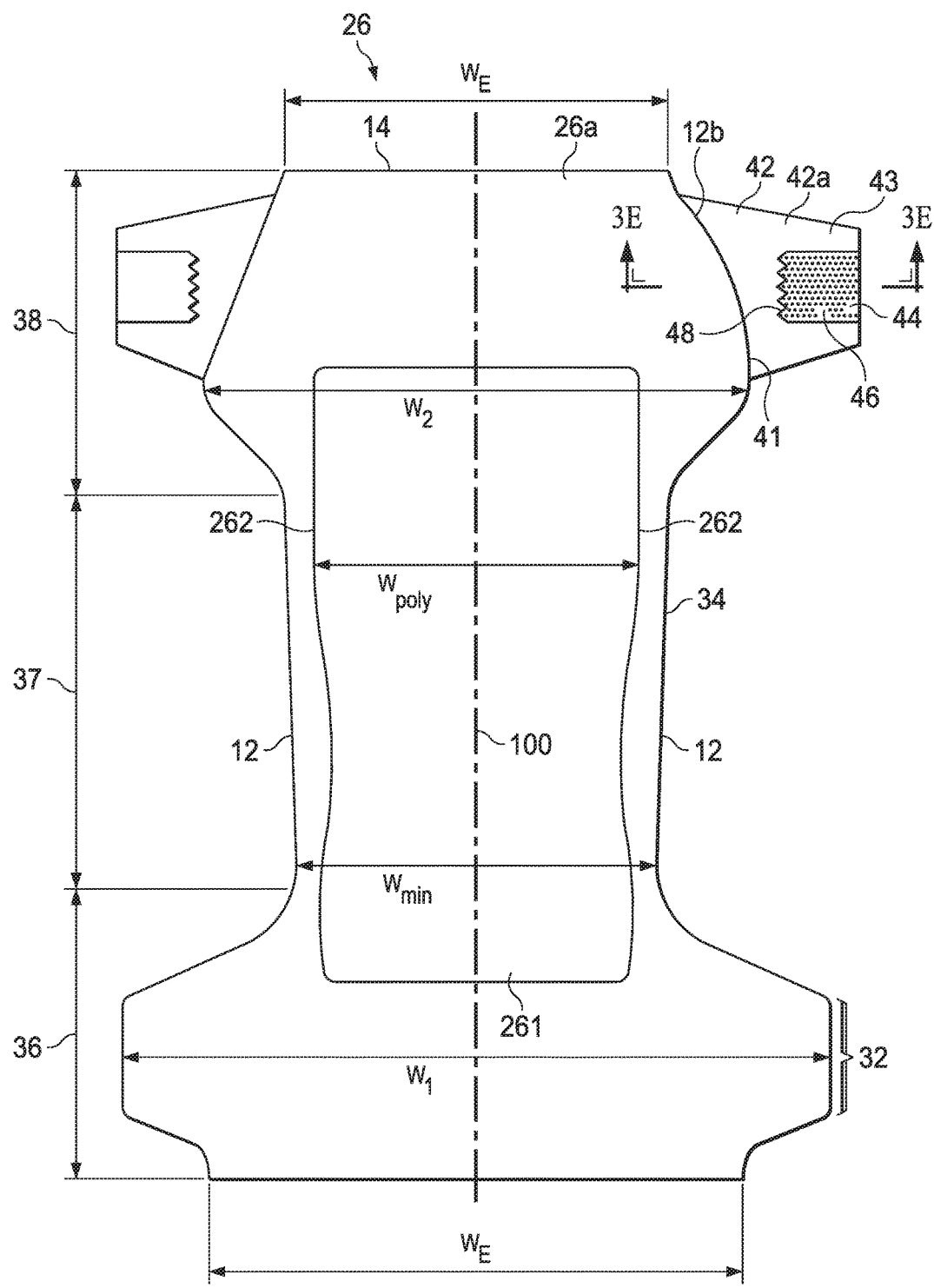
FIG. 3A is a schematic plan view of a backsheet in accordance with an embodiment of the present invention.

The backsheet 26 may comprise a material periphery 34 defined by the outermost longitudinal and lateral edges of one or more layers of the backsheet 26. In an embodiment, the backsheet material periphery 34 may be coterminous with the chassis periphery 30 as illustrated in FIGS. 2 and 3A. In one nonlimiting example, the backsheet 26 comprises the first maximum width, $W_1$, in the front waist region 36, the minimum width, $W_{min}$, in the crotch region 37 and the second maximum width, $W_2$, in the second waist region 38. The second maximum width, $W_2$, can be less than the first maximum width, $W_1$. It is desirable for the backsheet material periphery 34 to define the chassis periphery 30 to prevent the appearance of loose material edges or seams and thereby create a higher quality impression.

In such embodiment, the chassis 22 may be shaped by providing the backsheet 26 at a continuous first maximum width, $W_1$, and subsequently trimming the backsheet 26 to define narrower widths outside of the first maximum width zone 32. The backsheet 26 may be joined to the absorbent core 28 and/or topsheet 24 before, during or after the trimming process. The formation of the material periphery 34 or chassis periphery 30 may be achieved by any known means, including but not limited to die cutting, stamping, shear cutting, or the like.

In a further embodiment, the chassis periphery 30 continually slopes outside of the first maximum width zone 32. By "continually slopes", it is meant that the longitudinal edges are shaped such that the lateral distance between the longitudinal edge 12 and the longitudinal centerline 100 continually changes except within the first maximum width zone 32. That is, any two adjacent points P1, P2 along a longitudinal edge 12 outside of the first maximum width zone 32 are disposed at different lateral distances, $D_{P1}$ and $D_{P2}$, from the longitudinal centerline 100. In one nonlimiting example, the angle α between (i) any straight span, 12SP, on the longitudinal edge 12 outside of the maximum width zone 32 and (ii) the longitudinal centerline 100 is at least about 2 degrees. Where the chassis 22 is formed from a starting material having a continuous width equal to the first maximum width, $W_1$, the continual slope outside of the first maximum width zone 32 permits the chassis 22 to be formed without die cut spans that are parallel to the centerline 100; such parallel spans are known to impact the die-tool life negatively by causing repetitive wear in the same areas resulting in shorter die life, increased maintenance costs, decreased line efficiency and/or increased manufacturing costs.

In a further embodiment, the article 20 may comprise two leg gasketing systems 70 disposed on opposite longitudinal sides (see FIG. 1). In such nonlimiting example, the article 20 may comprise a maximum cuff width, $W_{cuff}$, such dimension being the maximum lateral distance between the outer cuff edges 77. In an embodiment, the maximum cuff width, $W_{cuff}$, may be greater than the minimum chassis periphery width, $W_{min}$, by at least about 10 mm or at least about 15 mm. Leg gasketing systems 70 are discussed in more detail below.

In another embodiment shown in FIG. 3A, the backsheet 26 may comprise a polymeric film layer 261 having a maximum lateral width, $W_{poly}$, which is the maximum lateral dimension of the polymeric film layer. (FIG. 3 schematically depicts the body-facing side 26a of the backsheet 26.) In one nonlimiting example, the polymeric film maximum lateral width, $W_{poly}$, is less than the minimum chassis width, $W_{min}$, as illustrated in FIG. 3A. The polymeric film maximum lateral width, $W_{poly}$, may be less than the minimum chassis periphery width, $W_{min}$, by at least about 5 mm or at least about 8 mm, or at least about 10 mm; and/or the polymeric film maximum lateral width, $W_{poly}$, may be less than the minimum chassis periphery width, $W_{min}$, by at least about 2.5 mm on each longitudinal side 262 of the polymeric layer 261, or at least about 5 mm on each longitudinal side 262. The polymeric film layer 261 may be positioned such that both of the layer's longitudinal edges 262 are disposed inboard of the backsheet material periphery 34 and/or inboard of the chassis longitudinal edges 12. In one nonlimiting example, the material periphery 34 is coterminous with the chassis periphery 30 as discussed above. In another nonlimiting example, the polymeric film maximum width, $W_{poly}$, is greater than the minimum chassis width, $W_{min}$. The polymeric film maximum width, $W_{poly}$, may greater than the minimum chassis periphery width, $W_{min}$, by at least about 10 mm, or at least about 15 mm, or at least about 20 mm, or at least about 5 mm on each longitudinal side 12 of the chassis at the minimum width, $W_{min}$, or at least about 10 mm on each longitudinal side 12 of the chassis at the minimum width, $W_{min}$. The polymeric film maximum width, $W_{poly}$, may be less than the first maximum width, $W_1$, or less than the second maximum width, $W_2$.

An ear 42, having any of the features described above, may be included in the second waist region 38 as shown in FIG. 3A. The back ear 42 may be stretchable 42a, such as an ear 42 formed from a zero strain stretch laminate or other elastomeric material. Further, the stretchable back ear 42a may be highly extensible. In embodiments with stretchable ears 42a, it may be preferable to join a discrete back ear 42 due to the cost of materials utilized for stretchable ears 42a versus the cost of materials used to form the backsheet 26 and remaining chassis 22 components. Where the chassis 22 is shaped by trimming the backsheet 26, the back ear 42 may be joined to the chassis 22 before, after or during the trimming process.

Figure 3B:
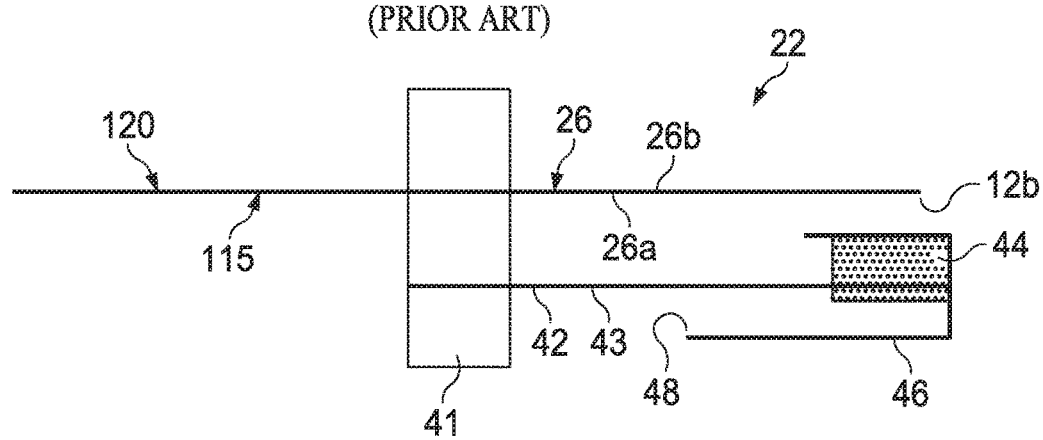
FIGS. 3B-3C are schematic cross-sectional views of prior art backsheet and ear assemblies.
Figure 3C:
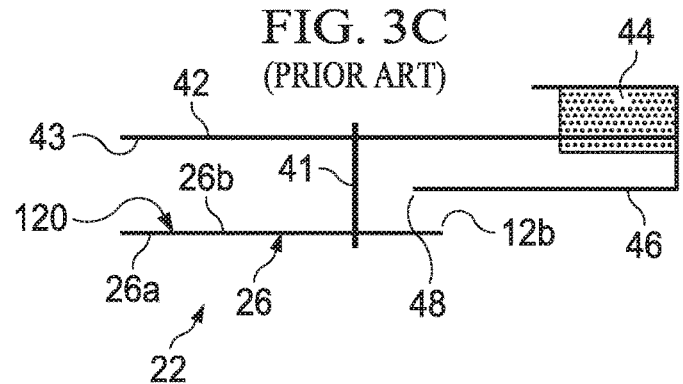
Figure 3D:
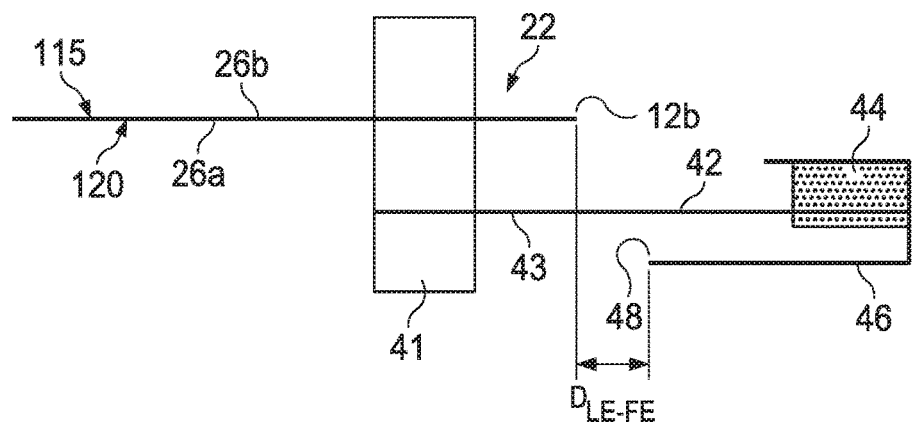
FIG. 3D is a schematic cross-section view of an exemplary embodiment of a backsheet and ear assembly as detailed herein.
Figure 3E:
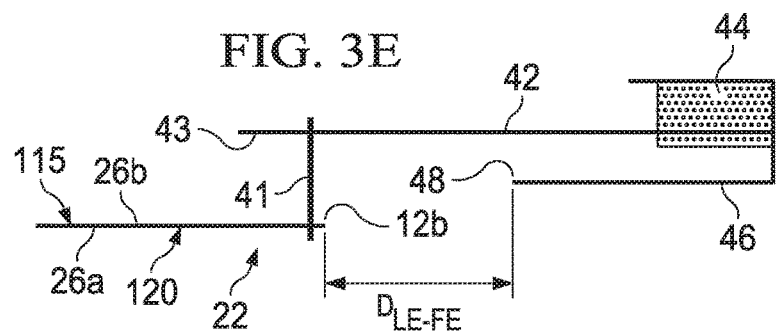
FIG. 3E is a schematic cross-sectional view of an exemplary embodiment of the backsheet of FIG. 3A, the cross-section taken along the line 3E-3E.
Figure 8:
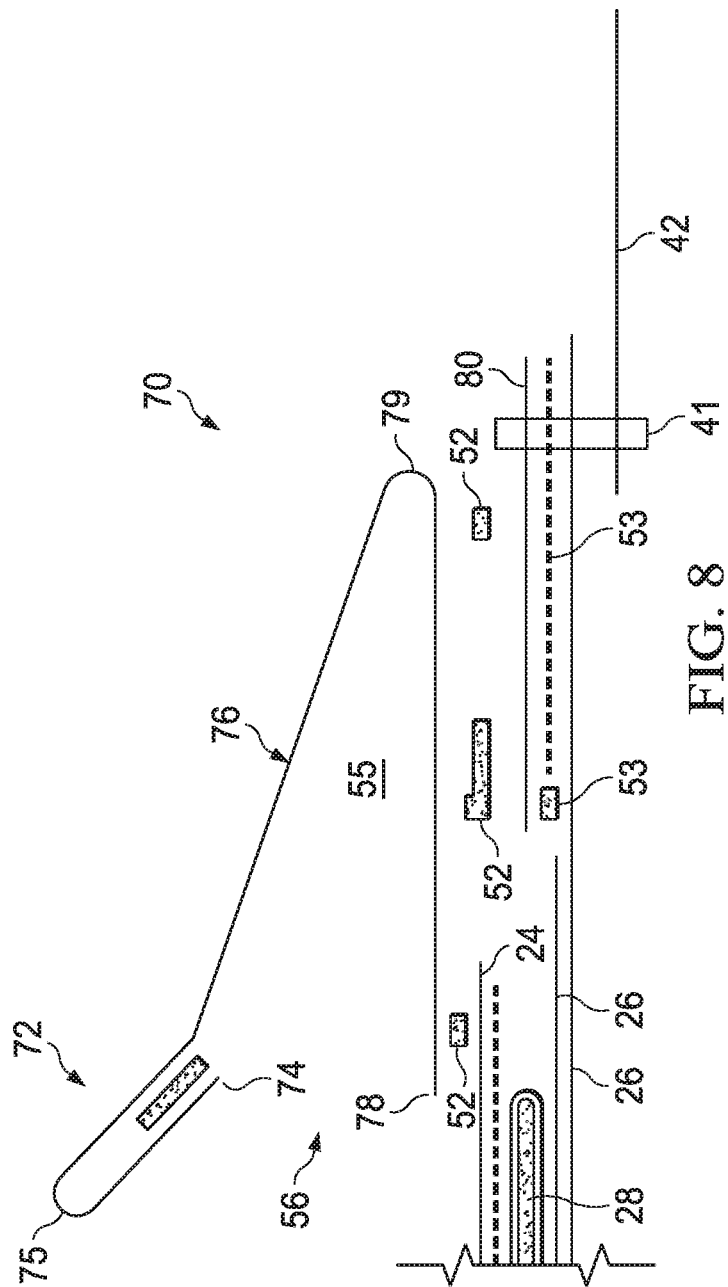
FIG. 8 is a schematic cross sectional view of an exemplary embodiment of the absorbent article of FIG. 1 with an opacity strengthening patch, the cross section taken along the line A-A.

The discrete ear 42 may be joined to any suitable layer of the chassis 22, and to any side of the chosen layer, at an ear attachment site 41. The ear 42 may be joined by any means known in the art. In a nonlimiting example, the discrete ear 42 is joined to the body-facing side 26a of the backsheet 26 as shown in FIGS. 3B and 3D. In another nonlimiting example, the discrete ear 42 is joined to the garment-facing side 26b of the backsheet 26 as shown in FIGS. 3A, 3C and 3E. In another nonlimiting example, the ear 42 is joined to the body-facing side of the opacity strengthening patch 80 as shown in FIG. 8. Alternatively, the ear 42 may also be attached to the leg gasketing system 70.

Returning to FIG. 3A, a fastening system 44 comprising a fastener 46, as described above, may be disposed on the ear 42. The fastener 46 may comprise an inboard fastener edge 48 which is disposed on the body-facing side 43 of the ear 42 and is the longitudinal edge of the fastener 46 closest to the longitudinal centerline 100. The fastener 46 may be foldable such that is partially disposed on the body-facing side 43 of the ear and partially disposed on the garment-facing side 45 of the ear (see, e.g., FIGS. 3B-3E). As depicted in FIGS. 3D and 3E, the inboard fastener edge 48 may be disposed such that the minimum lateral distance, $D_{LE-FE}$, between on the longitudinal edge 12b and the fastener edge 48 (measured between any two parallel points on those edges, said points being disposed along on an imaginary lateral line) is about 0 mm or greater, or from about 0 mm to about 40 mm, or from about 1 mm to about 30 mm, or from about 2 mm to about 20 mm, or about 6 mm, or about 4 mm, reciting for each range every 1 mm interval therebetween. The minimum lateral distance, $D_{LE-FE}$, is measured from the longitudinal edge 12b outboard, such that the ranges provided herein result in the chassis periphery 30 being coterminous with or inboard of the inboard fastener edge at the minimum lateral distance, $D_{LE-FE}$. In this way, the fastener edge becomes easier to access when the ear 42 is attached to the garment-facing side 26b of the backsheet 26, or the garment-side 120 of the chassis 22. The fastener edge 48 may be substantially straight, curvilinear, or combinations thereof.

When the first maximum width, $W_1$, is greater than the second maximum, $W_2$, accessibility of the fastener edge 48 can be further enhanced. Where the second maximum width, $W_2$, is greater than or equal to the first maximum width $W_1$ (as it is in known articles), issues can arise. For example, if $W_2$ were greater or equal to $W_1$ and the ear were joined to the garment-facing side 120, 26b of a layer of the chassis 22, the fastener edge 48 may be covered between the ear 42 and the chassis 22 and thus difficult to find during application, as shown in FIG. 3C. If, in this width scenario ($W_2 \geq W_1$), the ear 42 were alternatively joined to the body-facing side of a chassis layer (e.g., the body-facing side of the backsheet 26a), then an excess, loose portion of chassis 22 material may remain outboard of the attachment site 41 of the ear 42 as shown in FIG. 3B. The excess portion may look unsightly to an end-user. Further, including stretchable ears 42a in the second region 38 in such scenario could result in (i) the article's waist area being too large for a given weight range of users and/or (ii) the ears being otherwise inadequate for their desired purpose. When the second maximum width, $W_2$, is less than the first maximum width, $W_1$, these issues are avoided as shown in FIGS. 3D and 3E. The fastener edge 48 is visible and easier to engage and little to no excess material remains outboard the attachment site 41, without having to increase ear and/or bond site dimensions (either one of which could lead to extra costs and production inefficiencies). Moreover, stretchable ears may be more optimally utilized.

Elasticized Regions

The article 20 may comprise one or more elasticized regions 200 as shown for example in FIGS. 4A through 5B. Elasticized regions 200 may be disposed in leg cuffs 71, waist regions 36, 38, waist gasketing elements 81 disposed in waist regions, ears 40, 42, and/or other portions of the article 20 as is known in the art. For purposes of this section, the location in which the elasticized region is found will be referred to as the component 500. The component 500 comprises an outermost edge 502 (e.g., cuff edge, waist edge, waist gasketing element edge, ear edge), which may be a folded edge 503. The elasticized region 200 may comprise an array 240 of elastic members 210, which may comprise different properties including but not limited to different strain levels and/or different attachment profiles. The array 240 may be longitudinal or lateral depending on the structure of the component 500 and contraction requirements. In some embodiments, elastic members 210 in the array 240 run generally parallel to the component outermost edge 502.

The elastic members 210 may be elastomeric fibers, such as LYCRA® fibers available from INVISTA of Wichita, Kans. in various decitex levels. The skilled person may select the appropriate decitex based on the desired contraction and other principles discussed herein. Other suitable elastics can be made from natural rubber, such as elastic tape sold under the trademark Fulflex 9411 by Fulflex Company of Middletown, R.I. The elastic members 210 may also comprise any heat shrinkable elastic material as is well known in the art. In addition, elastic members 210 may take a multitude of configurations. For example, the width may be varied; a single strand or several parallel or non-parallel strands of elastic material may be used; or a variety of shapes may be used including rectilinear and curvilinear; or a variety of cross sectional shapes can be used (circular, rectangular, square, etc.).

In one embodiment, adjacent elastic members 210a, 210b are spaced at least 3.5 mm apart from one edge of the member to the other edge of the member, optionally at least 4 mm apart; optionally at least 4.5 mm apart; optionally at least 5 mm apart; optionally at least 5.5 mm apart; optionally at least 6 mm apart; optionally at least 6.5 mm apart; optionally at least 7 mm apart; optionally at least 7.5 mm apart; optionally at least 8 mm apart; optionally at least 8.5 mm apart; optionally at least 9 mm apart; optionally at least 9.5 mm apart; optionally at least 10 mm apart; optionally at least 10.5 mm apart; optionally at least 11 mm apart; optionally at least 11.5 mm apart; optionally at least 12 mm apart. The spacing is measured in the direction perpendicular to the direction of extension (i.e., if the elastic members are longitudinally extending, the spacing is a lateral measurement).

Elastic members 210 may be sandwiched (i) between discrete layers of the component 500, (ii) between the component 500 and the backsheet 26 or other portion of the article 20, and/or (iii) between a continuous piece of material folded about itself to form layers of the component 500. Alternatively, elastic members 210 may be joined to an outer side of the component 500 such that the elastic members are not sandwiched between layers. The elastic members 210 may be joined to the component 500 or one or more of said layers by glue bond, heat bond, pressure bond, mechanical bonds, ultrasonic or any other bonding method known in the art. In an embodiment, one or more of the elastic members 210 are joined to the component by strand coating.

The array 240 may comprise a first elastic member 214 and a second elastic member 216. The first elastic member 214 may be disposed between (i) the component's outermost edge 502 and (ii) the second elastic member 216, as shown for example in FIG. 4A. The first and second elastic members 214, 216 may run generally parallel to the component edge 502.

In an embodiment, the first elastic member 214 comprises a first elastic strain, $\varepsilon_1$, and the second elastic member 216 comprises a second elastic strain, $\varepsilon_2$. Strain may be determined by the Strain Test Method herein. The second elastic strain, $\varepsilon_2$, is different from the first elastic strain, $\varepsilon_1$. In one nonlimiting example, the first and second elastic strains, $\varepsilon_1$, $\varepsilon_2$, differ by at least about 50%, or from about 75% to about 200%, or about 100% to about 150%, reciting for each range every 10% increment therein, when said elastic members are joined to the component 500 and/or chassis 22. In another nonlimiting example, the second elastic strain, $\varepsilon_2$, is greater than the first elastic strain, $\varepsilon_1$. In a further nonlimiting example, at time installing the elastics, the second elastic strain, $\varepsilon_2$, is greater than the first elastic strain, $\varepsilon_1$, by at least about 50%, or from about 75% to about 200%, or about 100% to about 150%, reciting for each range every 10% increment therein.

One of skill in the art will recognize that the magnitude of strain differences in comparative elastic members 210 during manufacturing may be different than the magnitude of the strain differences of those same comparative elastic members 210 in the final product; however, the relationship between the elastic members' strain (i.e., one is greater than the other) may remain apparent in the final article 20.

The article 20 may comprise additional elastic members 210 which may comprise strain levels that are different from the first strain, $\varepsilon_1$, and/or different from the second strain, $\varepsilon_2$.

Figure 4A:
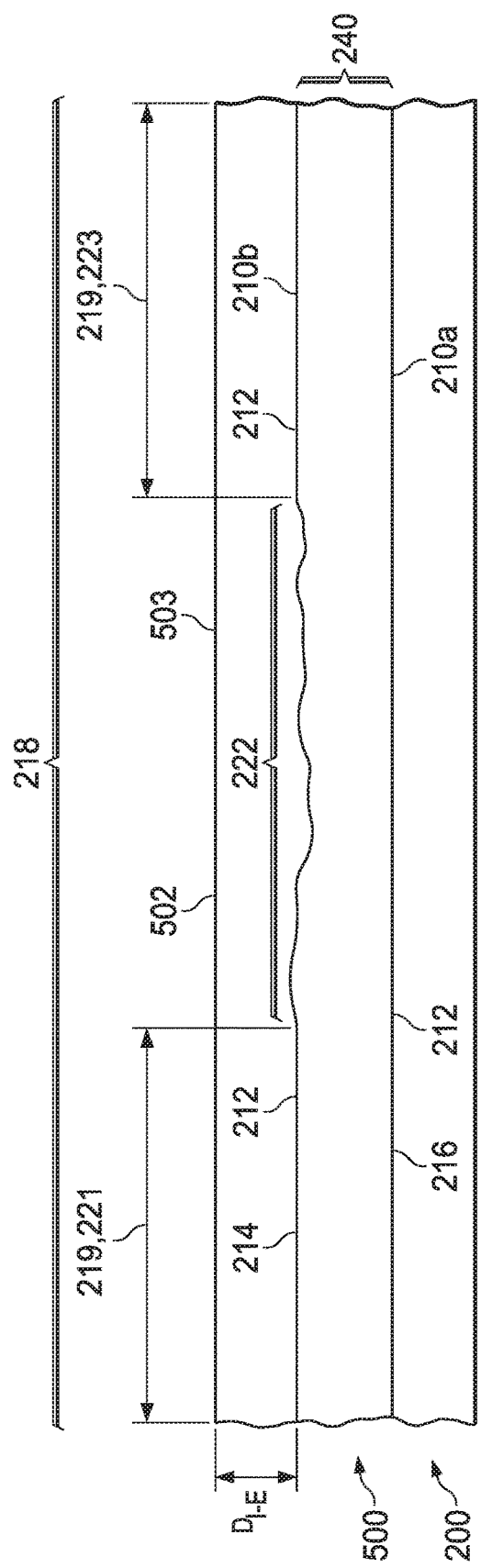
FIGS. 4A-4B are schematic plan views of exemplary embodiments of elasticized components as detailed herein. The elasticized components are shown in a flat, uncontracted state.
Figure 4B:
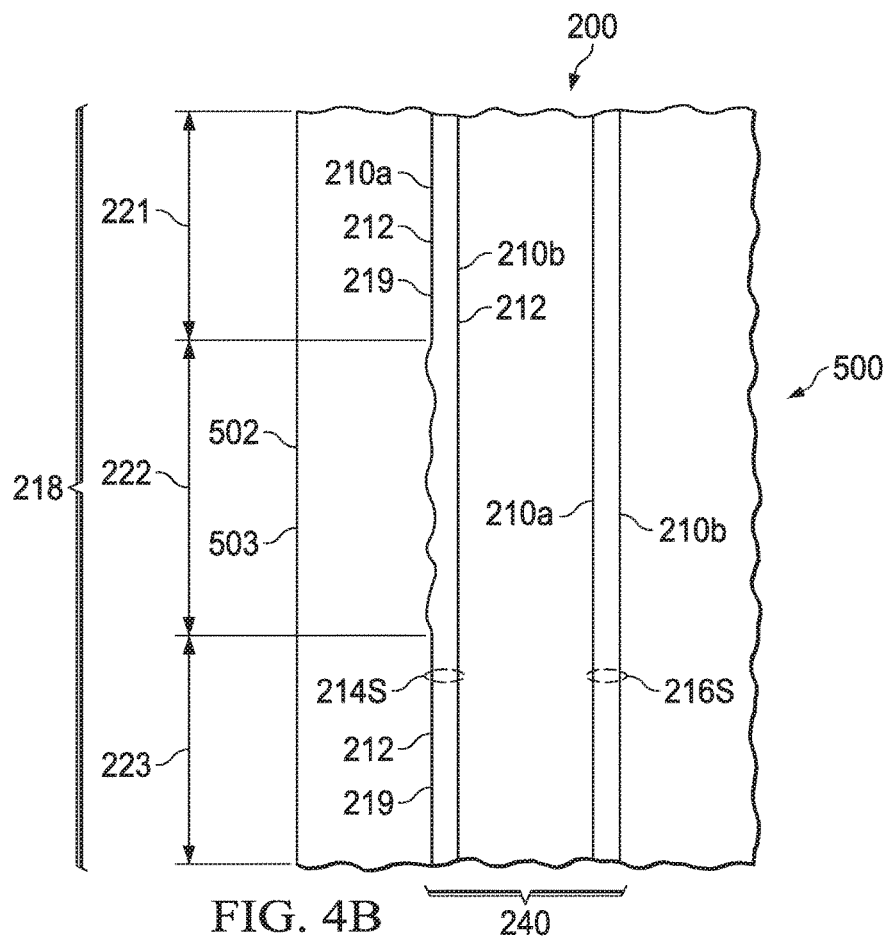
Figure 4C:
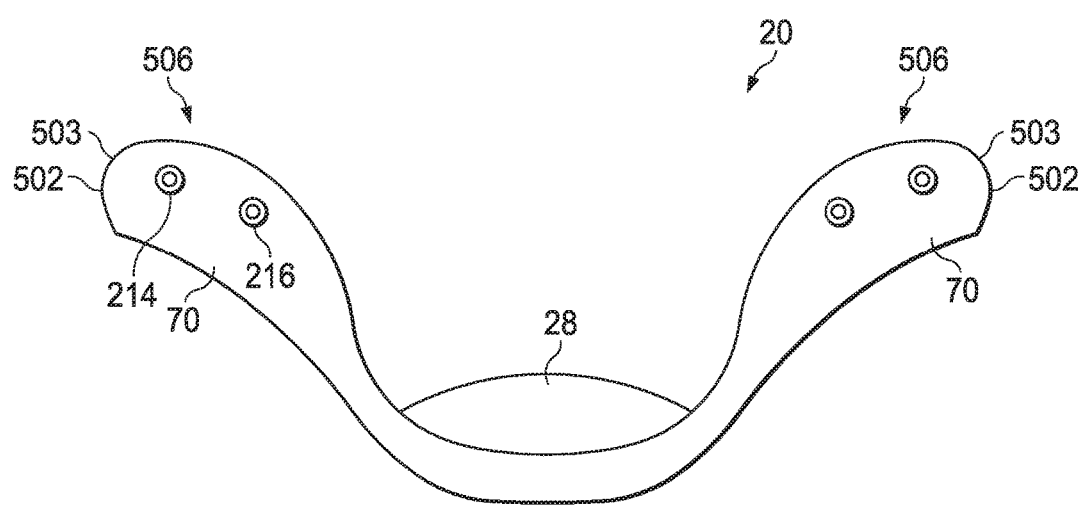
FIG. 4C is a schematic cross-sectional view of an exemplary absorbent article having exemplary elasticized leg cuffs as detailed herein.

In a further embodiment shown in FIG. 4B, the article 20 may comprise a first set of elastic members 214S and a second set of elastic members 216S, where the first set 214S is disposed between (i) the outermost edge 502 and (ii) the second set 216S. The first set 214S comprises a first aggregate strain (i.e., the sum of the strain levels of the elastic members in the set; each strain level being determined by the Strain Test Method herein), $\Sigma\varepsilon_1$, and the second set 216S comprises a second aggregate strain, $\Sigma\varepsilon_2$. The second aggregate strain, $\Sigma\varepsilon_2$, is different than the first aggregate strain, $\Sigma\varepsilon_1$. The second aggregate strain, $\Sigma\varepsilon_2$, may be greater than the first aggregate strain, $\Sigma\varepsilon_1$.

It is believed that, in use, the higher strained elastic members (e.g., 216, 216S) seek to wrap about the smallest possible circumference which represents the path length most closely matching their initial pre-stretched length and the lowest possible energy state the elastic member 210 can achieve. By increasing the strain of an elastic member 216 (or set of elastic members) that is further from the edge 502, said elastic member 216 seeks to fit the wearer at a smaller circumference than the elastic member closer to the edge 502. The increased strain on the inside elastic member 216 causes the outermost edge 502 to curve away wearer as shown in an exemplary leg gasketing system schematically depicted in FIG. 4C. The curvature allows a side portion 506 of the component 500 to contact the wearer's skin. In known constructions, the outermost edge 502 contacts the wearer's skin. The present invention allows for increased contact area between the article 20 and the skin in the elasticized region 200, which reduces localized, effective pressure on the skin and skin redness, pressure marks and/or irritation caused by such localized, effective pressure. Moreover, the differential strain causes fewer larger gathers at a larger wavelength towards the edge 502 where there is less contractive force and more consolidation of gathers away from the edge (towards the inside portion of the elasticized component) where there is more contractive force. Gathers are a result of the contraction of elastic members 210, where an elastic member 210 is contracted from a stretched length to a relaxed length that is shorter than the stretched length. This contraction creates a contraction force (F) that is exerted on the component 500. The contraction force F causes the component 500 to have a reaction force ($F_R$) that results in the creation of gathers that contain the physical characteristics of waves—oscillations that have a wavelength, amplitude, and frequency within a given phase.

Wave Function: $y(t)=A \sin(wt+\Delta)$, where A=amplitude, w=frequency, Λ=phase or length (l). The fewer, larger outer gathers at larger wavelengths reduces the number of ridges at the component's outermost edge 502; such ridges are known to irritate a wearer's skin.

Returning to FIGS. 4A and 4B, in some embodiments, the array 240 may comprise adjacent elastic members 210 each joined in a different manner to the component 500 in an attachment zone 218. The attachment zone 218 is an area of the component 500 where the elastic members 210 in the array 240 are joined to the component 500 and/or to the chassis 22. In the attachment zone, the first elastic member 214 can be joined to the component 500 and/or chassis 22 at two attachment intervals 219. The two attachment intervals 219 are separated by an unattached span 222. The second elastic member 216 may be adjacent to the first elastic member 214, and the second elastic member 216 can be continuously joined to the component 500 and/or chassis 22 in the attachment zone 218. Said differently, the elastic member 214 closest to the edge 502 is joined to the component 500 and/or chassis 22 at two intervals separated by an unattached span and an adjacent elastic member 216 (disposed further away from the edge 502) is continuously joined to the component and/or chassis 22. Alternatively, the first elastic member 214 can be joined to the component and/or to the chassis 22 continuously in the attachment zone 218 and the second elastic member 216 may be joined to the component 500 and/or chassis 22 at two intervals separated by an unattached span.

Further to the above, an unattached span 222 may comprise a length of from about 10 mm to about 60 mm, or at least about 20 mm, or at least about 30 mm or at least about 50 mm. In one nonlimiting example, glue 212 is applied in the first attachment interval 221 and in the second attachment interval 223, where said intervals are separated by an unglued span 222. The first attachment interval 221 may comprise the same shape, length, width, bonding material, bond strength, volume and/or density of bonding material (e.g., glue), and combinations thereof as the second attachment interval 223. Alternatively, the first and second intervals may differ in one or more of the above-mentioned characteristics. In a further nonlimiting example, at least one attachment interval 219 comprises a length of at least about 15 mm, or about 20 mm to about 100 mm, or about 30 mm, or about 40 mm, or about 60 mm, or about 80 mm, reciting for each range every 5 mm increment therein. In another nonlimiting example, at least one attachment interval 219 comprises glue add-on rate of from about 0.0175 g/m to about 0.0525 g/m, or from about 0.020 g/m to about 0.050 g/m, or from about 0.025 g/m to about 0.045 g/m, or from about 0.030 g/m to about 0.040 g/m, or about 0.035 g/m, reciting for each range every 0.005 g/m interval therebetween. The length of the attachment interval 219 may change based on the add-on rate and vice versa. The mentioned length and add-on rates have been shown to increase the likelihood of a partially glued elastic member 210 maintaining its initial bond strength and/or bond dimensions over time. In one nonlimiting example, the attachment interval 219 comprises about a length of about 30 mm and an add-on rate of about 0.035 g/m. Length in this paragraph is measured in the direction that elastic member 210 extends (e.g., longitudinal or lateral).

By differently joining adjacent elastic members in this way, it is believed that the potential for friction and/or pressure between the wearer's skin and the article 20 is reduced. The absence of bonds, such as glue bonds, along the span of the first elastic member 214 reduces the amount of contractive force on the component edge 502 and/or the edge of the article 20 closest and substantially parallel to the elastic member 214. Further, the lack of bonding reduces stiffness and sharpness of said edges. Moreover, when said component edge 502 or the closest, parallel article edge is folded, the lack of bonding may cause a rounded, balloon-like effect wherein the elastic member 210 or portions of the elastic member 210 may be free to move within the folded edge 503.

As noted, the elastic members 210 may be joined to the chassis 22 and/or component 500 by any suitable means. In one embodiment, the elastic members 210 are joined to the component 500 and/or chassis 22 with one or more adhesive bonds 212. The adhesive bonds 212 may be applied using strand coating techniques, such as applying glue directly to the elastic members 210 with one or more glue applicators, such as slot glue applicator. In one nonlimiting example, a glue applicator with independently controlled zones is utilized. The two zones may be programmed to start and stop at different time intervals, such that discrete glue intervals are applied to the first elastic member 214 in the attachment zone 218 and glue is continuously applied to the second elastic member 216 in the attachment zone 218. Alternatively, discrete glue intervals can be applied to the second elastic member 216 in the attachment zone 218 and glue can be continuously applied to the first elastic member 214 in the attachment zone 218.

In another embodiment shown in FIG. 4D, an additional adhesive 253 may be applied. The additional adhesive 253 may disposed in the unattached span 222. If the adhesive 253 is applied in the unattached span 222, portions of the elastic member 210 will be attached to surrounding material in that span 222 and portions will remain unattached. In one nonlimiting example, the additional adhesive 253 is applied through patterned slot coating techniques as taught in U.S. Pat. Pub. Nos. 2014/0148323, 2014/0148773, 2014/0148774 and 2014/0144579. In such embodiment, the first elastic member 214 may comprise an attachment pattern 220 and may be joined to the surrounding material by more than two attachment intervals 219. FIGS. 4D and 4E provide exemplary patterns 220 but numerous patterns are contemplated. By attachment pattern, it is meant a predetermined design comprising one or more shapes and/or lines; in a given pattern, at least one shape or line may repeat.

Figure 5B:
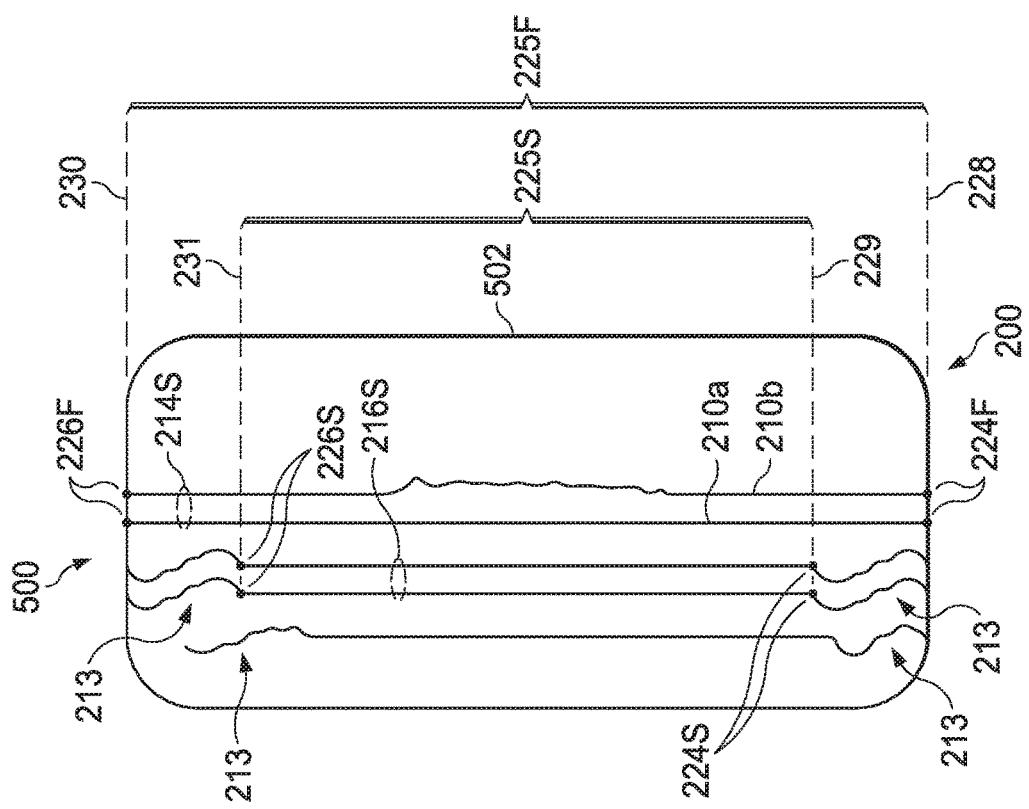
FIGS. 5A-5B are schematic plan views of exemplary embodiments of elasticized components as detailed herein. The elasticized components are shown in a flat, uncontracted state.
Figure 5A:
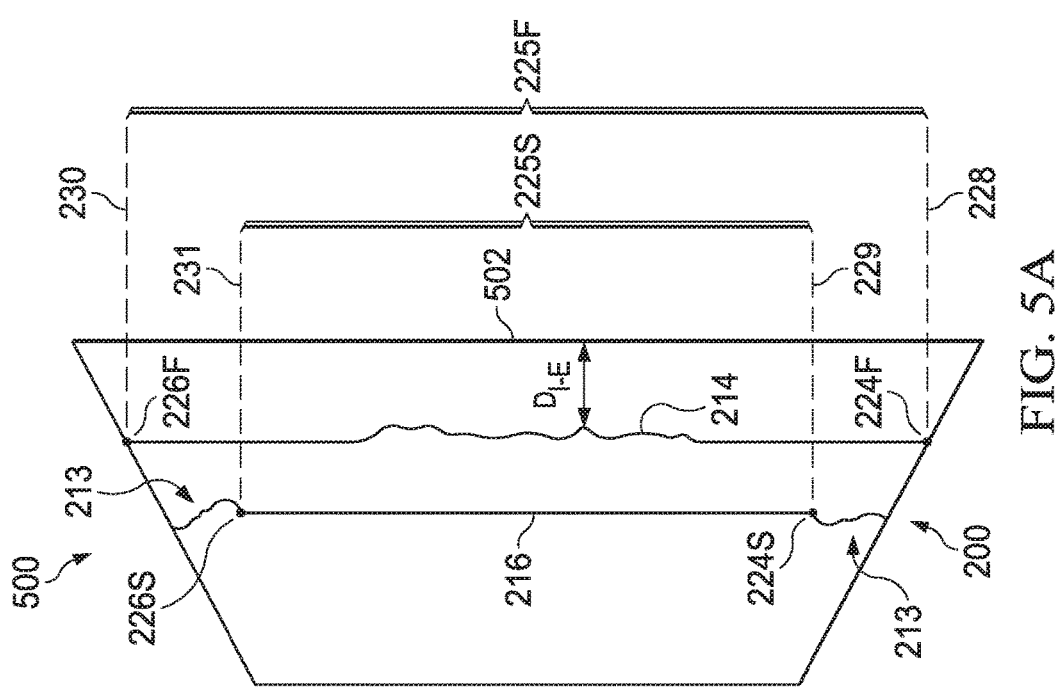

Turning to FIGS. 5A and 5B, in an embodiment, an elastic member 210 is joined to the component 500 and/or chassis 22 at both a contraction starting point 224 and a contraction ending point 226. A contraction region 225 extends between the starting point 224 and ending point 226. Further, the elastic member 210 may be unattached and cut to release tension in the snap back areas 213, which are disposed outside of the contraction region 225. In the snap back areas 213, the elastic member 210 is free to snap back to its original unstretched length without contracting the surrounding material. Each starting point 224 may be disposed along a start axis, and each ending point 226 may be disposed along an end axis. Axis, with respect contraction starting and ending points, means an imaginary line intersecting the respective starting point or ending point and running perpendicular to the direction of extension of the elastic members 210.

Each elastic member 210 in the array 240 may have a contraction region 225 extending between a contraction starting point and a contraction ending point. All of the contraction regions 225 for the elastic members 210 in the array 240 are disposed within the attachment zone 218. Snap-back regions 213 may be disposed outside of the attachment zone 218.

In known absorbent articles, the attachment starting points of multiple elastics are typically linear, meaning that the corresponding mechanical or glue bonds for each elastic member is applied along the same axis (an axis that is perpendicular to the direction of the extension of the elastic members). Likewise, the ending points are disposed along one axis. This has largely been due to limitations of equipment technology that apply bonds at high speeds. If those starting points are located inboard of the chassis periphery, wrinkles to the chassis may be formed especially when the starting points are near other bonds (e.g., cuff tackdown bonds). The wrinkles create the impression of low quality and can contribute to the pulling down of the chassis during use. Other issues are created when the starting or ending points are disposed outboard of the chassis periphery. For instance, in leg cuffs, if starting points or ending points are located outboard of the chassis periphery, an uncontracted triangle shaped zone may be formed in the leg cuff system (between a contoured chassis periphery and the imaginary lateral line created by the attachment starting points). That uncontracted triangle shaped zone creates a gap between the wearer and the leg cuff system, precluding proper fit and creating an impression of inadequate leakage protection.

By independently selecting the starting or ending points of elastic members 210 in the array 240, one or more of these issues may be avoided. In one embodiment shown in FIG. 5A, a first elastic member 214 has first contraction starting point 224F disposed on a first start axis 228 that runs substantially perpendicular to the direction of extension of the elastic members 210 in the array 240. In such embodiment, a second elastic member 216 has a second contraction starting point 224S disposed on a second start axis 229, where the second start axis 229 also runs substantially perpendicular to the direction of extension of the elastic members 210 in the array. The first and second starting axes 228, 229 may be different (i.e., not overlapping). By way of nonlimiting example, two longitudinally extending elastic members may have contraction starting points disposed on two different lateral axes. In a further embodiment, the first elastic member 214 has a first contraction ending point 226F disposed on a first end axis 230, and the second elastic member 216 has a second contraction ending point 226S disposed on a second end axis 231. The first and second end axes 230, 231 each run substantially perpendicular to the direction of extension of the elastic members 210 and may be different (i.e., not overlapping). In some embodiments, the first elastic member may comprise a first contraction region 225F and the second elastic member may comprise a second contraction region 225S. The second contraction region 225S may be different than the first contraction region 225F. In one nonlimiting example, the contraction regions 225F, 225S differ in length (as shown in FIG. 5A and measured in the direction parallel to the direction of extension of the elastic members). Additional nonlimiting examples of differences in the contraction regions 225F, 225S include the amount of contraction, bonding material, bond strength and bond dimensions.

In a further embodiment shown in FIG. 5B, the array 240 comprises a first set of elastic members 214S and a second set of elastic members 216S. The first set 214S comprises a first set of contraction starting points 224F disposed on a first start axis 228 that runs substantially perpendicular to the direction of extension of the elastic members 210 in the array 240. The second set 216S comprises a second set of contraction starting points 224S disposed on a second start axis 229 that also runs substantially perpendicular to the direction of extension of the elastic members 210 in the array 240. The start axes 228, 229 may be different. In a further embodiment, the sets 214S, 216S each comprise a set of contraction ending points 226F, 226S disposed on different axes 230, 231 as shown in FIG. 5B. In a further embodiment, the first set of elastic members 214S may comprise one or more elastic members 214 having a first contraction region 225F. The second set 216S may comprise and one or more elastic members 216 having a second contraction region 225S. The second contraction region 225S may be different than the first contraction region 225F. In one nonlimiting example, the contraction regions 225F, 225S differ in length (as shown in FIG. 5B and measured in the direction parallel to the direction of extension of the elastic members). Additional nonlimiting examples of differences in the contraction regions 225F, 225S include the amount of contraction, bonding material, bond strength and bond dimensions.

Figure 5C:
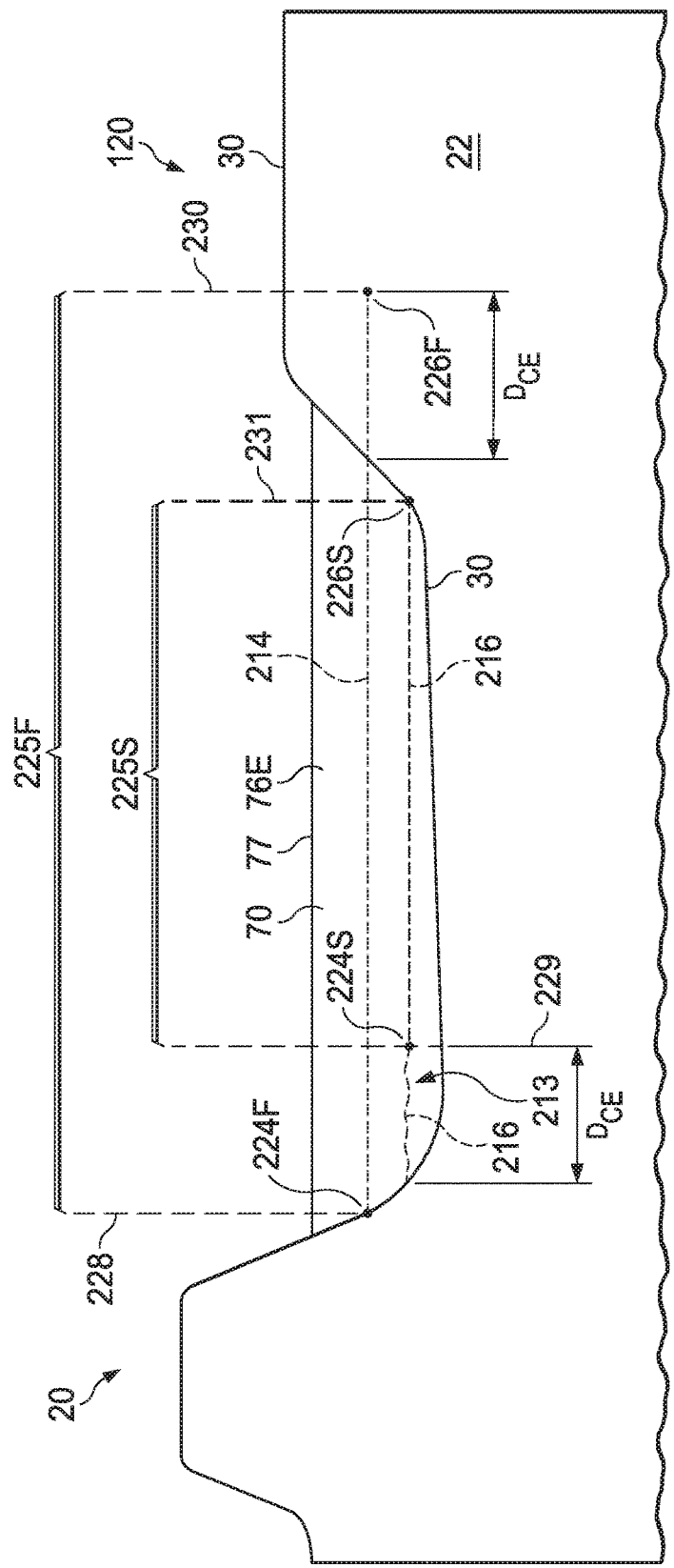
FIG. 5C is a partial, schematic plan view of an exemplary embodiment of an absorbent article shown in its flat, uncontracted state. The elasticized component is shown in a flat, uncontracted state.

Varying the starting points, ending points and/or contraction regions of elastic members 210 in the array 240 can prevent defects like wrinkles, prevent fit problems such as gaps created in snap back areas 213, and enhance fit by deliberating assigning contraction properties to the article at specific locations which may correspond to the article's contours. In one embodiment, at least one the starting points 224F, 224S and/or at least one of the ending points 226F, 226S are disposed on the chassis periphery 30 as shown in FIG. 5C in the context of an exemplary leg gasketing system 70. In a further embodiment also shown in FIG. 5C, at least one of the starting points 224F, 224S and/or at least one of the ending points 226F, 226S are disposed a distance, $D_{CE}$, from 0 mm to 6 mm of the chassis periphery 30 as measured in the direction of extension of the elastic members from the respective elastic starting point or ending point to the nearest point on the chassis periphery in said direction of extension.

Figure 5D:
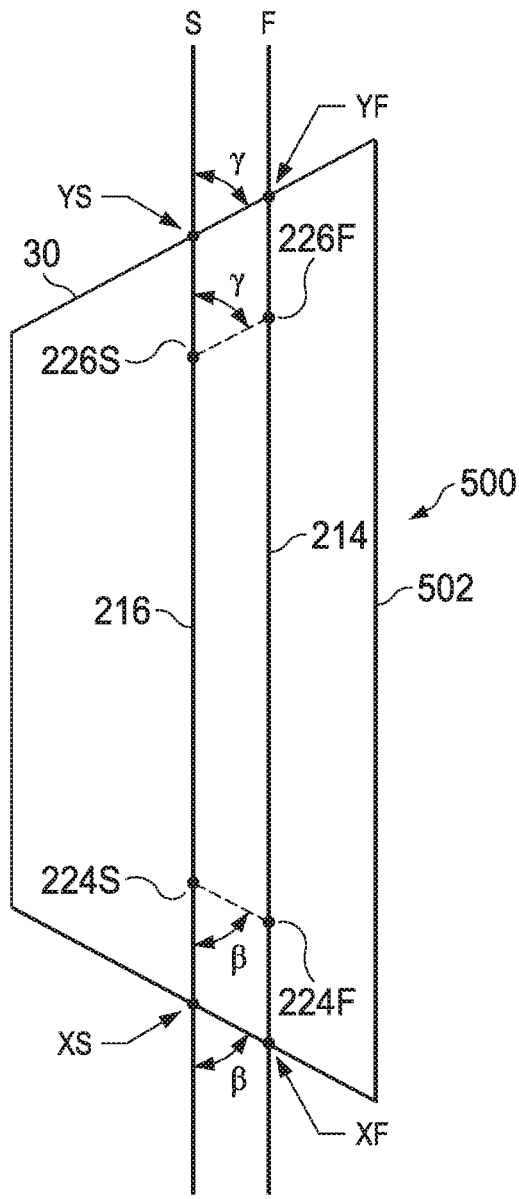
FIG. 5D is a schematic plan view of an exemplary embodiment of an elasticized component as detailed herein. The elasticized component is shown in a flat, uncontracted state.

In another embodiment shown in FIG. 5D, the chassis periphery 30 comprises a first initial intersection point XF. The first initial intersection point XF is a point on the chassis periphery 30 where an imaginary line F intersects the chassis periphery, the line F being superimposed over the first elastic member 214 and extending in the direction that the first elastic member 214 extends as shown in FIG. 5D. For ease of understanding, the component in FIG. 5D is shown to be coterminous with the chassis periphery along its outermost edge 502 and the sides that are adjacent to said edge. The chassis periphery 30 may further comprise a second initial intersection point XS. The second initial intersection point XS is a point on the chassis periphery 30 where an imaginary line S intersects the chassis periphery, the line S being superimposed over the second elastic member 216 and extending in the direction that the second elastic member 216 extends. In one nonlimiting example, the first starting point 224F is disposed at an angle β with respect to the second starting point 224S. The first initial intersection point XF can be disposed at substantially the same angle β with respect to the second initial intersection point XS. In an alternative nonlimiting example, the first initial intersection point XF is disposed at angle β±5 degrees with respect to the second initial intersection point XS. In another embodiment, the chassis periphery 30 comprises a first terminating intersection point YF defined by an imaginary line F intersecting the chassis periphery 30 and being superimposed on the first elastic member 214 and extending in the direction of extension of the first elastic member 214. The chassis periphery 30 may further comprise a second terminating intersection point YS defined by an imaginary line S intersecting the chassis periphery 30 and being superimposed on the second elastic member 216 and extending in the direction of extension of the second elastic member 216. In one nonlimiting example, the first end point 226F is disposed at an angle γ with respect to the second ending point 226S. In such example, the first terminating intersection point YF may be disposed at the same angle γ with respect to the second terminating intersection point YS. Alternatively, the first terminating intersection point YF may be disposed at an angle γ±5 degrees with respect to the second terminating intersection point YS.

Returning to FIG. 5A, in some embodiments, a first elastic member 214 is disposed a minimum distance $D_{1-E}$ from the component outermost edge 502 as measured perpendicularly to the direction of extension of the elastic members (i.e., if the elastic is longitudinally extending, the minimum distance of 3 mm is measured laterally). In one nonlimiting example, the minimum distance $D_{1-E}$ is greater than about 3 mm. Known disposable absorbent articles attach elastic members within 2 mm or less of the component edge 502, which enhances contact with the wearer but increases localized pressure on the skin and ridges near the edge 502 due to small, high frequency gathers at or near the edge 502. Further, in embodiments where the edge is folded 503 and in embodiments where elastic members 210 are sandwiched between two layers each having edges that are coterminous with the component outermost edge 502, a partially attached elastic member 214 nearest the edge 502 will tend to move into the edge 502 during wear, which can also increase localized pressure. This migration occurs because the elastic member 214 seeks the smallest circumference to wrap around in order to achieve its lowest energy state—the smallest circumference being the edge 502 in this case. A minimum distance $D_{1-E}$ of at least about 3 mm between the attached portion of said elastic member 214 and the edge 502 causes the elastic member 214 to be sufficiently trapped away from the outermost edge 502, reducing pressure and friction on the skin and allowing gathers to be felt by the wearer.

To the extent that the elasticized region is located in waist region 36 or 38, the elastic members 210 may be disposed such that the absorbent article 20 may lay substantially flat during application. Positioning and other components of this aspect of the invention are discussed below in the Waist Gasketing Element section.

In embodiments involving sets of elastic members, a set may comprise differentially strained elastic members 210 and/or adjacent elastics 210a, 210b differently joined to the surrounding material as taught herein (see, for example, FIG. 5B).

With respect to all embodiments, the first elastic member 214 or first set of elastic members 214S may be disposed between (i) the component edge 502 and (ii) the second elastic member 216 or second set of elastic members 216S respectively.

Leg Gasketing System

The absorbent article 20 may comprise a leg gasketing system 70 attached to the chassis 22, which may comprise an elasticized region 200 discussed more fully below. The leg gasketing system 70 comprises one or more cuffs 71. The leg gasketing system 70 may be constructed as, and comprise one or more features, disclosed in commonly assigned U.S. App. No. 62/134,622.

In an embodiment, the leg gasketing system 70 comprises an inner cuff 72 having an inner cuff edge 73. The inner cuff edge 73 may comprise an inner cuff material edge 74. Alternatively, the inner cuff material edge 74 may be folded such that the cuff edge 73 comprises a folded inner cuff edge 75. The leg gasketing system 70 may further comprise an outer cuff 76 that comprises an outer cuff edge 77. The outer cuff edge 77 may comprise the outer cuff material edge 78. Alternatively, the outer cuff material edge 78 may be folded such that the outer cuff edge 77 comprises a folded outer cuff edge 79.

FIGS. 6 and 7 depict schematic cross sectional views of the exemplary leg gasketing systems of FIG. 1 in a flat, uncontracted state, the views taken through the lateral centerline 110 (FIG. 6 is a schematic cross section of the left leg gasketing system, and FIG. 7 is a schematic cross section of both leg gasketing systems in relation to the topsheet).

In one embodiment, each leg gasketing system 70 comprises a single, continuous web of material. In other embodiments, the leg gasketing system 70 may be formed from more than one web of material (e.g., multiple webs of material that are joined together to become one web of material, or multiple distinct webs of material that are separate from the disposable absorbent article chassis and form part of the leg gasketing system). Herein, locations (e.g., folded edge, material edge, etc.) on the leg gasketing system 70 are detailed in reference to "a web of material" or "a portion of the web of material." The recitations of "a web of material" or "the web of material" refer to leg gasketing system embodiments that may be formed from a single, continuous web of material, multiple webs of material that are joined together to become one web of material, or multiple distinct webs of material that are separate from the disposable absorbent article chassis and form part of the leg gasketing system. All such embodiments are contemplated.

In some embodiments, the web of material is folded laterally inward (toward the longitudinal centerline 100 of the absorbent article 20) to form the outer cuff folded edge 79 and folded laterally outward (away from the longitudinal centerline 100 of the absorbent article 20) to form the inner cuff folded edge 75.

The cuffs 71 may be attached to the chassis 22 and/or each other 72, 76 by any suitable means. In an embodiment, the outer cuff 76 is attached to the chassis 22 through one or more cuff attachment bonds 52 as illustrated in FIG. 7. Further, a cuff attachment bond 52 may attach at least portion of web material in the outer cuff 76 to the opacity strengthening patch 80 in at least a portion of the first waist region 36 and at least a portion of the second waist region 38 as shown in FIG. 8. The opacity strengthening patch 80 may be attached to the inner layer of the backsheet 26 by at least one OSP bond 53. In an embodiment, the inner cuff edge 73 comprises a folded edge 75 and the outer cuff edge 77 comprises a folded outer cuff edge 79. In such embodiment, at least a portion of the web material between the inner cuff folded edge 75 and the outer cuff folded edge 79 can be attached to at least a portion of the web of material between the outer cuff folded edge 79 and the outer cuff material edge 78 in at least the crotch region 37 and the first waist region 36. The attachment of the web of material between the inner cuff folded edge 75 and the outer cuff folded edge 79 to the web of material between the outer cuff folded edge 79 and the outer cuff material edge 78 in at least the crotch region 37 and the first waist region 36 is made through utilization of one or more cuff separation bonds 54 (see FIG. 7). The leg gasketing system 70 may further comprise a pocket 55 arising from the web of material between the inner cuff folded edge 75 and the outer cuff folded edge 79 being unattached to the web of material between the outer cuff folded edge 79 and the outer cuff material edge 78 in one of the waist regions 36, 38 as shown in FIG. 8. The pocket 55 may provide additional void volume within the leg gasketing system 70 to receive exudates to help isolate fecal material from the wearer's skin as well as contain exudates between the layers of the leg gasketing system 70 to prevent leakage. The pocket 55 may comprise an opening 56 created by a break in the cuff separation bond 54 or a series of breaks in the cuff separation bond 54. The pocket and opening can occur in the first waist region 36, the second waist region 38 or the crotch region 37 as needed for the specific type of exudates and particular situation where leakage prevention is desired. Attachment of the outer cuff 76, the opacity patch 80 and/or inner cuff 72 and/or formation of the pocket 55 may be accomplished in accordance with the disclosure of commonly assigned U.S. Patent App. No. 62/134,622. The pocket 55 may be free from elastics 210.

Figure 9:
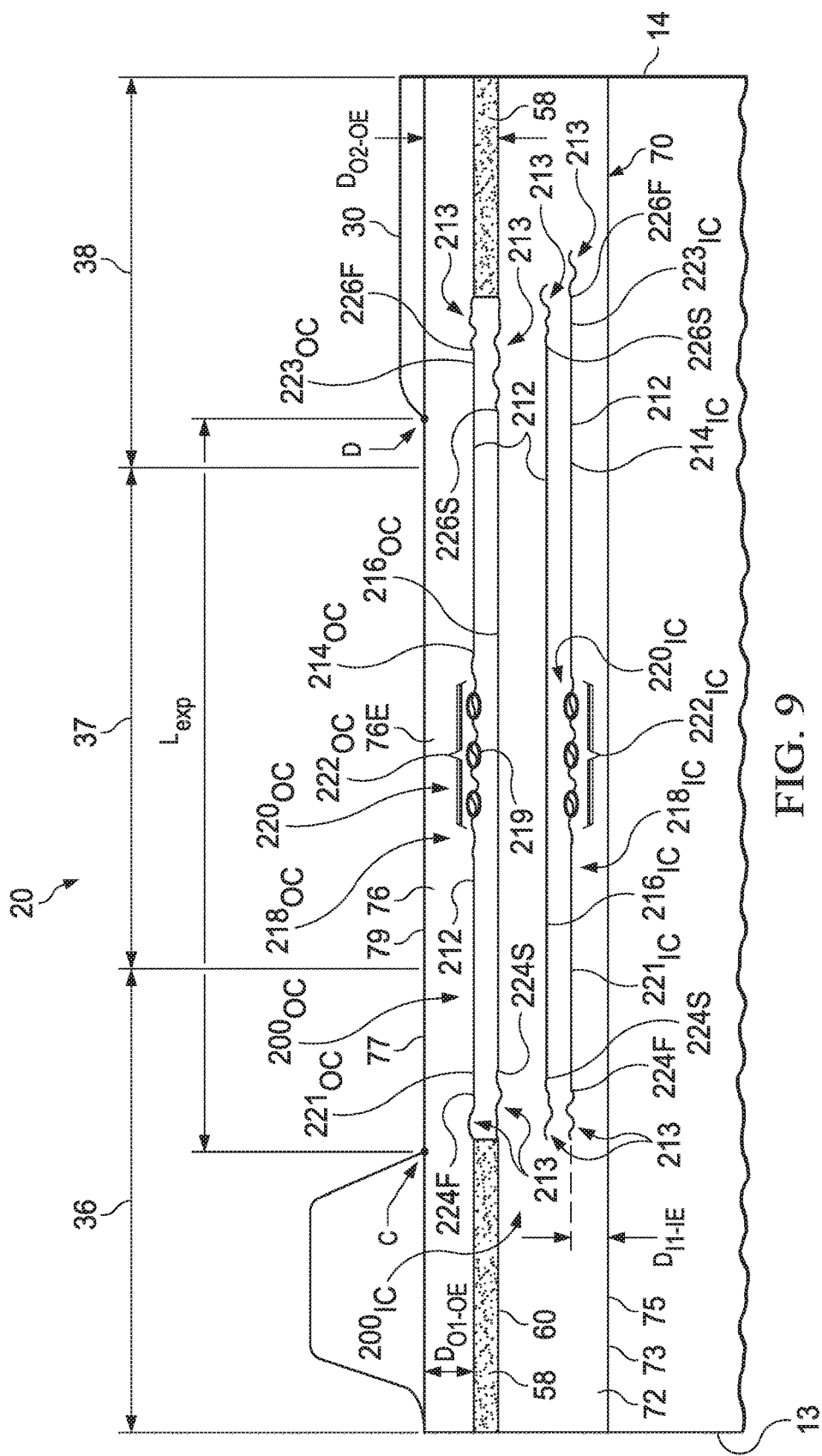
FIG. 9 is a partial, schematic plan view of an exemplary embodiment of an absorbent article having a leg gasketing system as detailed herein. The leg gasketing system is shown in a flat, uncontracted state.

In one embodiment shown in FIG. 9, one or more attachment bonds 52 can comprise a tackdown bond 58 which may be disposed in a waist region 36, 38 and may extend longitudinally in a continuous or substantially continuous manner in the waist region 36, 38. Attachment bonds 52, 58, OSP bonds 53 and/or cuff separation bonds 54 may take the form of glue, heat bond, pressure bond, mechanical bonds, ultrasonic or any other bonding method known in the art. In one nonlimiting example, the tackdown bond 58 takes the form of a glue bond 60.

The leg gasketing system 70 may comprise one or more elasticized regions 200 comprising one or more longitudinally extending elastic members 210 as can be seen in FIGS. 5C-7. The elastic members 210 may be joined to the web material by any suitable means including mechanical bonds and/or adhesive bonds 212. In an embodiment illustrated in FIG. 5C, an elastic member 210 is joined to the leg gasketing system 70 at both a contraction starting point and a contraction ending point. In such embodiment, the elastic member 210 is contracted between the starting point and ending point, forming a contraction region 225. In a nonlimiting example, the longitudinal length of the contraction region 225 of a first elastic member 214 is different than the length of the contraction region 225 of a second elastic member 216. In a further nonlimiting example, the longitudinal length of the contraction region 225 of the first elastic member 214 is greater than the longitudinal length of the contraction region 225 of the second elastic member 216. In another nonlimiting example, the contraction starting points may be disposed on different lateral axes and/or the contraction ending points may be disposed on different lateral axes as shown in FIG. 5C. Additional discussion of the contraction starting and ending points is included in the Elasticized Region section above.

As illustrated in FIGS. 6-7 and 9, the inner cuff 72 may comprise an inner cuff elasticized region $200_{IC}$ comprising one or more longitudinally-extending elastic members $210_{IC}$. The inner cuff elastic members $210_{IC}$ may run substantially parallel to the inner cuff edge 73. In one nonlimiting example, the elastic members $210_{IC}$ may be disposed between the inner cuff folded edge 75 and the outer cuff material edge 78. In an embodiment, the inner cuff elasticized region $200_{IC}$ comprises a first inner cuff elastic member $214_{IC}$ disposed outboard of the inner cuff edge 73 as shown in the flat, uncontracted state in, for example, FIGS. 6-7. The inner cuff elasticized region $200_{IC}$ may further comprise a second inner cuff elastic member $216_{IC}$ disposed outboard the first inner cuff elastic member $214_{IC}$ in the flat, uncontracted state. In some embodiments, the first inner cuff elastic member $214_{IC}$ may be adjacent to the second inner cuff elastic member $216_{IC}$. In one nonlimiting example, the first inner cuff elastic member $214_{IC}$ is disposed a minimum lateral distance, $D_{I1-I2}$, from the second inner cuff elastic member $216_{IC}$ as depicted in FIG. 6. The minimum lateral distance, $D_{I1-I2}$, may be from about 3.5 mm to about 10 mm.

In an embodiment, the first inner cuff elastic member $214_{IC}$ and the second inner cuff elastic member $216_{IC}$ may be differentially strained as discussed in more detail in the Elasticized Region section above. The first inner cuff elastic member $214_{IC}$ comprises a first inner elastic strain, $\varepsilon_{1ic}$, and the second inner cuff elastic member $216_{IC}$ comprises a second inner elastic strain $\varepsilon_{2ic}$. Strain may be determined by the Strain Test Method herein. The first inner elastic strain, $\varepsilon_{1ic}$, may be different than the second inner elastic strain, $\varepsilon_{2ic}$. In a nonlimiting example, the second inner elastic strain, $\varepsilon_{2ic}$, is greater than the first inner elastic strain, $\varepsilon_{1ic}$.

In a further embodiment shown in FIG. 9, the leg gasketing system 70 comprises an inner cuff elastic attachment zone $218_{IC}$ in which adjacent elastics $210_{IC}$ may be joined to the leg gasketing system 70 differently (which is discussed more completely above in the Elasticized Region section). In such embodiment, the inner cuff edge 73 is the outermost edge 503 of the component, the component being the inner cuff 72. In one nonlimiting example, the first inner cuff elastic member $214_{IC}$ is joined to the leg gasketing system 70 at a first inner attachment interval $221_{IC}$ and at a second inner attachment interval $223_{IC}$. The first inner attachment interval $221_{IC}$ may be at least partially disposed in the first waist region 36, and the second inner attachment interval $223_{IC}$ may be at least partially disposed in the second waist region 38. The attachment intervals $221_{IC}$, $223_{IC}$ are separated by an unattached span $222_{IC}$, which may be disposed in the crotch region 37. In such example, the second inner cuff elastic member $216_{IC}$ is continuously joined to the leg gasketing system 70 in the attachment zone $218_{IC}$. In a further nonlimiting example, the second elastic member $216_{IC}$ is continuously joined to the leg gasketing system 70 in the crotch region 37. In a further nonlimiting example, the elastic members $214_{IC}$, $216_{IC}$ are joined the web material in the inner cuff 72 using one or more adhesive bonds 212, and the unattached span $222_{IC}$ comprises an unglued span $222_{IC}$. It is also contemplated that the second inner elastic member $216_{IC}$ may be joined at two attachment intervals 219 separated by an unattached span 222, where the unattached span is disposed in the crotch region 37 and the attachment intervals are partially disposed in waist regions 36, 38, and the first inner elastic member $214_{IC}$ may be continuously joined to the leg gasketing system 70 within the attachment zone $218_{IC}$.

In another embodiment, the outer cuff 76 may comprise an outer cuff elasticized region $200_{OC}$ comprising one or more longitudinally-extending elastic members $210_{OC}$. The outer cuff elastic members $210_{OC}$ may run substantially parallel to the outer cuff edge 77. In one nonlimiting example, the elastic members $210_{OC}$ may be disposed between the outer cuff folded edge 79 and the inner cuff material edge 74. In an embodiment, the outer cuff elasticized region $200_{OC}$ comprises a first outer cuff elastic member $214_{OC}$ disposed inboard of the outer cuff edge 77 as shown in the flat, uncontracted state in FIGS. 6-7. The outer cuff elasticized region $200_{OC}$ may further comprise a second outer cuff elastic member $216_{OC}$ disposed inboard of the first outer cuff elastic member $214_{OC}$. In some embodiments, the first outer cuff elastic member $214_{OC}$ may be adjacent to the second outer cuff elastic member $216_{OC}$. In one nonlimiting example, the first outer cuff elastic member $214_{OC}$ is disposed a minimum lateral distance, $D_{O1-O2}$, from the second outer cuff elastic member $216_{OC}$ as depicted in FIG. 6. The minimum lateral distance, $D_{O1-O2}$, may be from about 3.5 mm to about 10 mm.

In an embodiment, the first outer cuff elastic member $214_{OC}$ and the second outer cuff elastic member $216_{OC}$ may be differentially strained as discussed in more detail in the Elasticized Region section above. The first outer cuff elastic member $214_{OC}$ comprises a first outer elastic strain, $\varepsilon_{1oc}$, and the second outer cuff elastic member $216_{OC}$ comprises a second outer elastic strain, $\varepsilon_{2oc}$. The first outer elastic strain, $\varepsilon_{1oc}$, may be different than the second outer elastic strain, $\varepsilon_{2oc}$. In a nonlimiting example, the second outer elastic strain, $\varepsilon_{2oc}$, is greater than the first outer elastic strain, $\varepsilon_{1oc}$. Strain may be determined by the Strain Test Method herein.

In a further embodiment shown in FIG. 9, the leg gasketing system 70 comprises an outer cuff elastic attachment zone $218_{OC}$ in which the first outer cuff elastic member $214_{OC}$ and the second outer cuff elastic member $214_{OC}$ may be joined to the leg gasketing system 70 differently (which is discussed more completely above in the Elasticized Region section). In one nonlimiting example, the first outer cuff elastic member $214_{OC}$ is joined to the leg gasketing system 70 at a first outer attachment interval $221_{OC}$ and a second outer attachment interval $223_{OC}$. The first outer attachment interval $221_{OC}$ may be at least partially disposed in the first waist region 36, and the second outer attachment interval $223_{OC}$ may be at least partially disposed in the second waist region 38. The attachment intervals $221_{OC}$, $223_{OC}$ are separated by an unattached span $222_{OC}$, which may be disposed in the crotch region 37. In such example, the second outer cuff elastic member $216_{OC}$ is continuously joined to the leg gasketing system 70 in the attachment zone $218_{OC}$. In a further nonlimiting example, the elastic members $214_{OC}$, $216_{OC}$ are joined the web material in the outer cuff 76 using one or more adhesive bonds 212, and the unattached span $222_{OC}$ comprises an unglued span $222_{OC}$. While described above in terms of the second elastic member being continuously joined to the leg gasketing system 70 and the first outer cuff elastic member being attached at two intervals 219 separated by an unattached span 222, it is also contemplated that the second outer elastic member $216_{OC}$ may be joined at two attachment intervals 219 separated by an unattached span 222 and the first elastic member $214_{OC}$ may be continuously joined to the leg gasketing system 70 within the attachment zone $218_{OC}$.

The inner cuff 72 and/or outer cuff 76 may comprise additional cuff elastic members 210. The inner cuff 72 may comprise at least one elastic member 210, at least two elastic members 210, at least three elastic members 210, at least four elastic members 210, or at least five elastic members 210. The outer cuff 76 may comprise at least two elastic members 210, at least three elastic members 210, at least four elastic members 210, at least five elastic members 210, or at least six elastic members 210. In one embodiment, the inner cuff 72 comprises an array of elastic members positioned between the inner cuff folded edge 75 and the inner cuff material edge 74. The elastic members $210_{IC}$ may be attached to the portion of the web of material that forms the inner cuff 72 by elastics adhesive 212. In such an embodiment, the elastics $210_{IC}$ are positioned between i) the portion of the web of material between the inner cuff folded edge 75 and the inner cuff material edge 74, and ii) the portion of the web material between the inner cuff folded edge 75 and the outer cuff folded edge 79. Likewise, the outer cuff 76 may comprise elastic members $210_{OC}$ positioned in a lateral array between the outer cuff folded edge 79 and outer cuff material edge 78. The elastics $210_{OC}$ may be attached to the portion of the web of material that forms the outer cuff by elastics adhesive 212. In such an embodiment, the elastic members $210_{OC}$ are positioned between i) the portion of the web of material between the outer cuff folded edge 79 and the outer cuff material edge 78, and ii) the portion of the web material between the outer cuff folded edge 79 and the inner cuff folded edge 75.

In an embodiment, any elastic members $210_{IC}$ in the inner cuff 72 and/or any elastic members $210_{OC}$ in the outer cuff 76 may be differentially strained. Strain levels in the outer cuff 76 may be the same as or different than strain levels in the inner cuff 72. In a further embodiment, the first inner elastic strain, $\varepsilon_{1ic}$, is different than the first outer elastic strain, $\varepsilon_{1oc}$. In one nonlimiting example, the first inner elastic strain, $\varepsilon_{1ic}$, is greater than the first outer elastic strain, $\varepsilon_{1oc}$. In another nonlimiting example, the first inner elastic strain, $\varepsilon_{1ic}$, is less than the first outer elastic strain, $\varepsilon_{1oc}$. In another embodiment, the second inner elastic strain, $\varepsilon_{2ic}$, is different than the second outer elastic strain, $\varepsilon_{2oc}$. In one nonlimiting example, the second inner elastic strain, $\varepsilon_{2ic}$, is greater than the second outer elastic strain, $\varepsilon_{2oc}$. In another nonlimiting example, the second inner elastic strain, $\varepsilon_{2ic}$, is less than the second outer elastic strain, $\varepsilon_{2oc}$.

In still another embodiment, any adjacent elastic members $210_{IC}$ in the inner cuff 72 and/or any adjacent elastic members $210_{OC}$ in the outer cuff 76 may be differently joined to the leg gasketing system 70 in the respective attachment zones $218_{IC}$, $218_{OC}$. In a further embodiment, adjacent elastic members $210_{OC}$ in the outer cuff 76 may be attached differently than adjacent elastics $210_{IC}$ in the inner cuff 72. In one nonlimiting example, the first inner elastic member $214_{IC}$ is joined to the leg gasketing system in IC attachment pattern $220_{IC}$ and the first outer elastic member $214_{OC}$ is joined to the leg gasketing system 70 in an OC attachment pattern $220_{OC}$. The IC attachment pattern $220_{IC}$ may be different from the OC attachment pattern $220_{OC}$. Alternatively, the IC attachment pattern $220_{IC}$ may be the same as the OC attachment pattern $220_{IC}$. The attachment patterns 220 may be formed by pattern slot coating.

In one embodiment, the outer cuff 76 and inner cuff 72 are the same color. In one embodiment, the outer cuff 76 and inner cuff 72 are different colors. In one embodiment, there is an additional printing on one or more of the cuffs 71 of the leg gasketing system 70. In embodiments with printing on both the inner 72 and outer cuffs 76, the printing may be the same or different on each cuff 71.

In some embodiments, the outer cuff edge 77 extends outboard of the chassis periphery 30 in the crotch region 37 to form an exposed outer cuff 76E as shown in FIGS. 5C and 9. In one nonlimiting example, the backsheet 26 and/or polymeric film layer 261 may be spaced laterally inward of the outer cuff edge 77 by about 10 mm; optionally about 20 mm; optionally about 30 mm; optionally about 40 mm. In another nonlimiting example, the outer cuff edge 77 extends outboard of the chassis periphery 30 for a maximum longitudinal distance, $L_{exp}$, of from about 10 mm to about 35 mm, or from about 15 mm to about 20 mm, as measured between intersection points C and D where the outer cuff edge 77 intersects the chassis periphery 30 as shown in FIG. 9. In a further nonlimiting example, the lateral distance, $D_{O1\text{-}OE}$, between the first outer cuff elastic member $214_{OC}$ and the outer cuff edge 77 may be about 5% to about 55%, or from about 6% to about 50% of the maximum longitudinal distance, $L_{exp}$, for each range reciting every 5% increment therein. The outer cuff edge 77 may comprise a folded outer cuff edge 79 in such example. Alternatively, the outer cuff edge 77 may comprise two or more layers that have edges coterminous with the outer cuff edge 77 in such example. In another nonlimiting example, the lateral distance, $D_{O2\text{-}OE}$, between the second outer cuff elastic member $216_{OC}$ and the cuff edge 77 may be about 30% or greater of the maximum longitudinal distance, $L_{exp}$, or from about 35% to about 95% of the maximum longitudinal distance, $L_{exp}$, for each range reciting each 5% increment therebetween. In such nonlimiting example, the cuff edge 77 may comprise a folded cuff edge 79 or the cuff edge 77 may be coterminous with the edges of two or more layers of the outer cuff 76. In these embodiments, it is believed that the first elastic member $214_{OC}$ will resist the tendency to move into the cuff edge 77 as discussed more completely in the Elasticized Region section.

In one embodiment, the leg gasketing system 70 is spaced laterally inward of the chassis longitudinal edge 12 by about 10 mm, optionally about 20 mm, optionally about 30 mm, optionally about 60 mm or more. In another embodiment, at least a portion of the lateral edge of the outer cuff 76 extends to the laterally outboard edge 13, 14 of the chassis 22 as shown, for example, in FIG. 9. In still another embodiment, at least a portion of the lateral edge of the outer cuff 76 is disposed longitudinally inboard of the laterally outboard edge 13, 14 of the chassis 22.

In one embodiment, the outboard edge 77 of the leg gasketing system 70 is disposed laterally inboard of at least a portion of the longitudinal edge of the article 20 in at least one of the waist regions 36, 38. Thus, in one embodiment, the front ears 40 and/or back ears 42 extend past the leg gasketing system 70.

Figure 10:
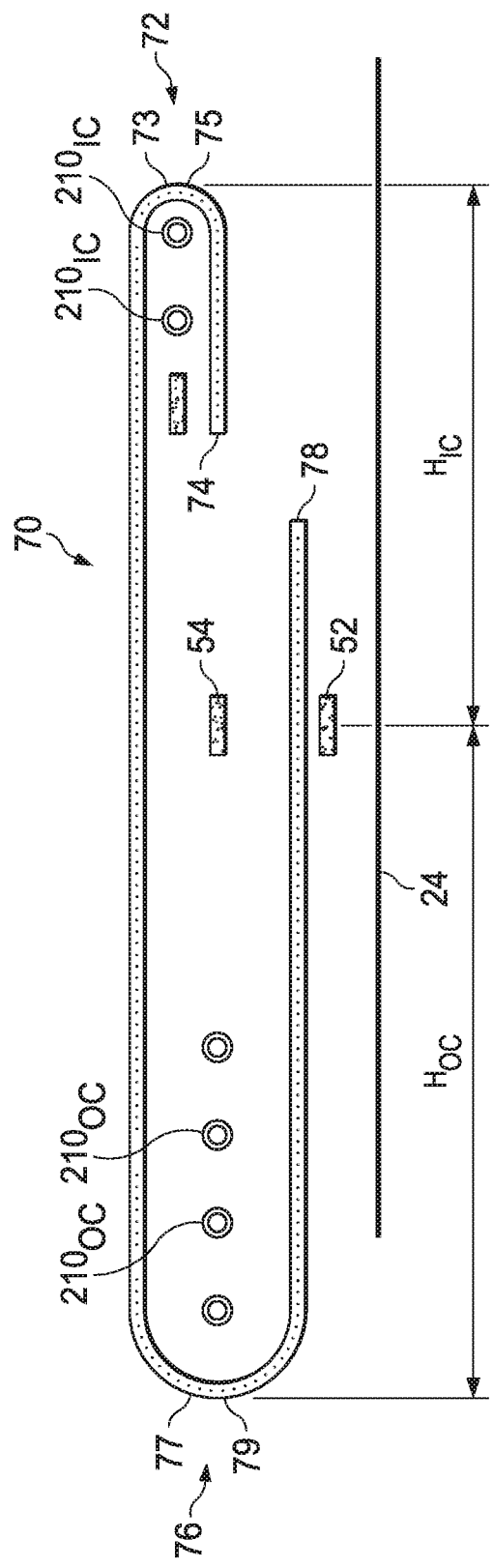
FIG. 10 is a schematic cross-sectional view of an exemplary embodiment of one of the leg gasketing systems of FIG. 1, taken along the lateral centerline. The leg gasketing system is shown in a flat, uncontracted state.

As shown in FIG. 10, the outer cuff 76 has an outer cuff height, $H_{OC}$, and the inner cuff 72 has an inner cuff height, $H_{IC}$. In an embodiment, the inner cuff height, $H_{IC}$, is less than the outer cuff height, $H_{OC}$. In alternative embodiments, the outer cuff height, $H_{OC}$, and the inner cuff height, $H_{IC}$, are substantially equivalent or the inner cuff height, $H_{IC}$, is greater than the outer cuff height, $H_{OC}$. In one embodiment, the height of the inner cuff, $H_{IC}$, is at least about 10 mm, at least about 20 mm, at least about 30 mm, at least about 32 mm, at least about 35 mm, or at least about 38 mm. In one embodiment, the outer cuff height, $H_{OC}$, is at least about 15 mm, at least about 23 mm, at least about 25 mm, at least about 27 mm, or at least about 30 mm. The inner cuff height, $H_{IC}$, is measured along a lateral line from inner cuff edge 73 to the first point of connection to the chassis 20 in the crotch region 37. The outer cuff height is measured along a lateral line from the outer cuff edge 77 to the first point of connection to the chassis 20 in the crotch region 37. In one nonlimiting example, the height of the inner cuff is measured along a lateral line from inner cuff folded edge 75 to the first point of connection to a material beyond the inner cuff material edge 74 in the crotch region. Further, the outer cuff height is measured along a lateral line from the outer cuff folded edge 75 to the first point of connection the inner cuff 72 has to a material beyond the inner cuff material edge 73 in the crotch region 37. Thus, in such example, the inner and outer cuffs are measured from their respective folded edges to the point where the inner cuff is connected to the first material beyond the inner cuff material edge 74. Where the outer cuff height, $H_{OC}$, is greater than or appears greater than the inner cuff height, $H_{IC}$, in the contracted state, the intended function of the outer cuff (as a secondary barrier) is indicated to the user. In some embodiments, the inner cuff elastic members comprise an aggregate strain level that is higher than the aggregate strain of the outer cuff elastics. In this way, the path length of the inner cuff elastic members in the contracted state is shorter than the path length of the outer cuff elastic members, and consequently, the outer cuff may appear to have a greater height than the inner cuff. In such embodiments, the outer cuff height, $H_{OC}$, may actually be greater than the inner cuff height, $H_{IC}$.

In embodiments where the cuff edge 73, 77 comprises a folded cuff edge 75, 79 and/or in embodiments where more than one layers has an edge coterminous with the cuff edge 73, 77, the first elastic member 214 may be disposed a lateral distance, $D_{1\text{-}E}$, of at least about 3 mm from the cuff edge 73, 77. In this way, the first elastic member 214 will resist the tendency to be move into the edge 73, 77 as discussed more completely above in the Elasticized Region section.

The inner and/or outer cuff 72, 76 may comprise sets of elastic members 214S, 216S and any of the embodiments taught with respect to sets in the Elasticized Region section herein. Further, one or more of the cuffs 71 may be constructed of N-fiber as disclosed in U.S. patent application Ser. No. 15/074,047.

Waist Gasketing Element

Figure 11:
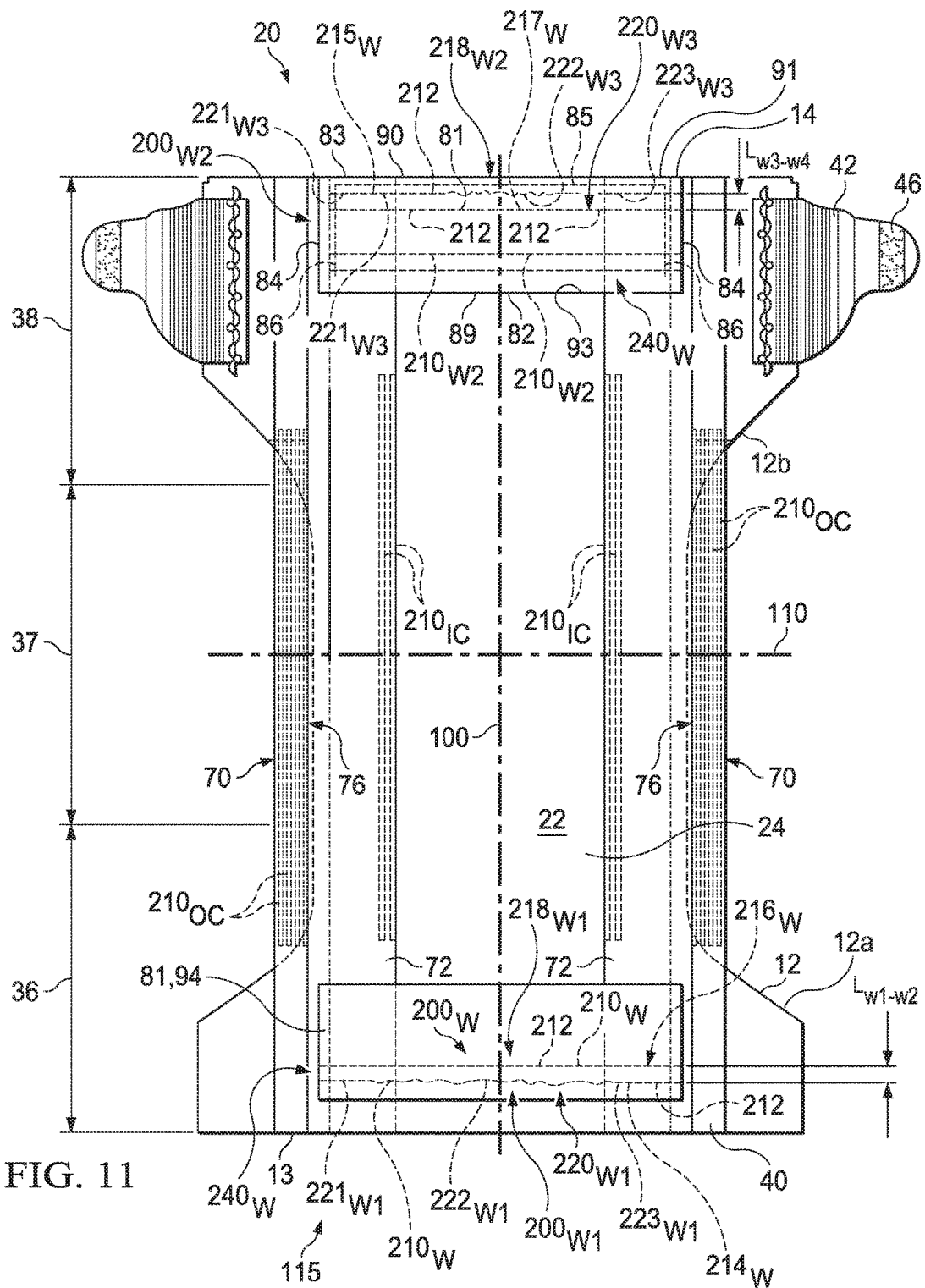
FIG. 11 is a schematic plan view of an exemplary embodiment of an absorbent article as detailed herein. The article is shown in a flat, uncontracted state.

The disposable absorbent article 20 may include at least one waist gasketing element 81 attached to the chassis 22. The waist gasketing element 81 may be disposed on the body facing side 115 of the chassis or a body-facing side of a layer of the chassis 22. In an embodiment, the waist gasketing element 81 comprises an elasticized waistband 94 as shown in FIG. 1. In another embodiment, the waist gasketing element 81 comprises a waist gasketing element pocket 93 as shown in FIG. 11. The pocket 93 may be formed from a portion of the waist gasketing element 81 that is unattached from the chassis 22. Waist gasketing elements 81 may be joined to the chassis 22 in the first waist region 36 and/or in the second waist region 38. In one nonlimiting example, the waist gasketing element 81 is disposed in the second waist region 38.

In one embodiment, the at least one waist gasketing element 81 comprises a single, continuous web of material. In other embodiments, the waist gasketing element(s) 81 may be formed from more than one web of material (e.g., multiple webs of material that are joined together to become one web of material, or multiple distinct webs of material that are separate from the disposable absorbent article chassis and form part of the waist gasketing element). Herein, locations (e.g., folded edge, material edge, etc.) on the waist gasketing element 81 are detailed in reference to "a web of material", "a portion of the web of material" or "waist material." The recitations of "a web of material" or "the web of material" or "waist material" refer to waist gasketing element embodiments that may be formed from a single, continuous web of material, multiple webs of material that are joined together to become one web of material, a single material that is folded to form multiple layers of the same material, a single material that is slit apart and rejoined together, or multiple distinct webs of material that are separate from the disposable absorbent article chassis and form part of the waist gasketing element 81. All such embodiments are contemplated.

In one embodiment, the waist gasketing element 81 includes an inboard lateral edge 82, an outboard lateral edge 83, and two longitudinal edges 84. The outboard lateral edge 83 may be coterminous with a waist edge 13, 14. Alternatively, the outboard lateral edge 83 may be disposed longitudinally inward of the waist edge 13, 14.

In some embodiments, the web of material forming the waist gasketing element 81 is folded longitudinally outward (away from the lateral centerline 110 of the absorbent article 20) to form the inboard lateral edge 82. In such embodiments, the inboard lateral edge 82 is also the location of the waist gasketing element folded edge 89 and the outboard lateral edge 83 is also the location of the waist gasketing element first material edge 90 and the waist gasketing element second material edge 91. Although an embodiment depicting a waist gasketing element 81 with one folded edge 89 and two material edges 90, 91 is shown in FIG. 11, alternate constructions of useful waist gasketing elements are contemplated. For example, an alternate waist gasketing element 81 may include two distinct webs of material and therefore have four material edges (two on the inboard lateral edge 82, and two on the outboard lateral edge 83). As another example, an alternate waist gasketing element may have a continuous web material that is formed into having two folded edges (one on the inboard lateral edge 82, and one on the outboard lateral edge 83) and two material edges.

In a further embodiment, the waist gasketing element 81 may be used in conjunction with a leg gasketing system 70 as shown in FIG. 11. In such embodiment, the waist gasketing element 81 is attached to: 1) the chassis 22 and 2) the leg gasketing system 70, such that at least a portion of the outboard lateral edge 83 of the waist gasketing element 81 is attached to the chassis 22 and at least a portion of the outboard lateral edge 83 of the waist gasketing element 81 is attached to the web of material of the leg gasketing system 70. The inboard lateral edge 82 of the waist gasketing element 81 may be unattached, partially unattached or fully attached to the chassis 22 of the disposable absorbent article 20. In embodiments that include a waist gasketing element 81 that has a waist gasketing element folded edge 89, a waist gasketing element first material edge 90, and a waist gasketing element second material edge 91, at least a portion of the web of material between the waist gasketing element folded edge 89 and waist gasketing element second material edge 91 is attached to the topsheet 24 and/or backsheet 26 of the chassis 22. The attachment of the waist gasketing element 81 to the chassis 22 is made through utilization of one or more outboard lateral edge bonds 85 (see, for example, the rear waist gasketing element on FIG. 11). The outboard lateral edge bond 85 attaches at least a portion of the waist gasketing element's web of material between the waist gasketing element folded edge 89 and the waist gasketing element second material edge 91 to the topsheet 24. In one embodiment, the attachment bond 85 is at the second waist edge 14 of the chassis 22; in other embodiments, the attachment bond is placed at least 2 mm inboard from the waist edge of the chassis; at least 10 mm inboard from the waist edge of the chassis; at least 20 mm inboard from the waist edge of the chassis; at least 50 mm inboard from the waist edge of the chassis; or any range or distance within the range of about 2 mm to about 50 mm inboard from the waist edge of the chassis. The outboard lateral edge bond 85 may take the form of glue, heat bond, pressure bond, mechanical bonds, or any other bonding method known in the art. In the exemplary embodiment of FIG. 11, the outboard lateral edge bond 85 takes the form of a glue bond.

In embodiments that include a waist gasketing element 81 that has a waist gasketing element folded edge 89, a waist gasketing element first material edge 90, and a waist gasketing element second material edge 91, at least a portion of the web of material between the waist gasketing element folded edge 89 and waist gasketing element second material edge 91 is attached to the web of material forming the leg gasketing system 70. The attachment of the waist gasketing element 81 to the web of material forming the leg gasketing system 70 is made through utilization of one or more longitudinal edge bond(s) 86. As seen in the embodiment of FIG. 11 (see the rear waist gasketing element), the longitudinal edge bonds 86 attach at least a portion of the waist gasketing element's web of material between the waist gasketing element folded edge 89 and the waist gasketing element second material edge 91 to the web of material forming the leg gasketing system 70. The longitudinal edge bonds 86 can be located adjacent to the longitudinal edges 84 of the waist gasketing element 81 (or may be coterminous therewith). In another embodiment, the longitudinal edge bonds 86 are located adjacent to the inner cuff folded edge 75 of the leg gasketing system 70 (or may be coterminous therewith). The waist gasketing element 81 may be attached to the leg gasketing system 70 over substantially the entire area that the leg gasketing system 70 overlaps with the waist gasketing element 81. In some embodiments, the waist gasketing element 81 is attached to the leg gasketing system 70 over more than about 50%, more than about 60%, more than about 70%, more than about 80%, more than about 90%, or more than about 95%, of the entire area that the leg gasketing system 70 overlaps with the waist gasketing element 81. The longitudinal edge bonds 86 may take the form of glue, heat bond, pressure bond, mechanical bonds, or any other bonding method known in the art. In the exemplary embodiment of FIG. 11, the longitudinal edge bonds 86 take the form of a glue bond.

In one nonlimiting example, the combination of the longitudinal edge bonds 86, the lateral outward edge bond 85 and unattached portion of the inboard lateral edge 82 of the waist gasketing element 81 (i.e., unattached from the chassis 22) forms a pocket 93. When the wearer moves, a portion of the bodily exudates will migrate into the waist gasketing element pocket 93 for containment and be held/trapped between two layers of nonwoven before it can leak out in an area between the wearer's back and the back waist region 38 of the absorbent article 20. In addition, the waist gasketing element pocket 93 provides additional void volume within the waist region to receive the fecal material which helps in isolating the fecal material from wearer's skin.

The waist gasketing element 81 and its attachment to the chassis 22 may be in accordance with U.S. Patent App. No. 62/134,622.

A waist region 36, 38 may comprise an elasticized region 200 comprising one or more laterally extending elastic members 210. The waist elastic members 210 may be disposed in an array 240. In one nonlimiting example, the waist elasticized region $200_W$ is disposed in a waist gasketing element 81 that is disposed within a waist region 36, 38. In the waist elasticized region $200_W$, one or more elastic members $210_w$ may be joined to the chassis 22 in the waist region and/or joined to the web of waist material. The elastic members $210_w$ may be joined to the chassis 22 and/or waist gasketing element 81 by any suitable means including mechanical bonds and/or adhesive bonds 212. In one nonlimiting example, the elastics may be positioned between i) the portion of the web of material between a waist gasketing element folded edge 89 and the waist gasketing element first material edge 90, and ii) the portion of the web material between the waist gasketing element folded edge 89 and the waist gasketing element second material edge 91.

Figure 12:
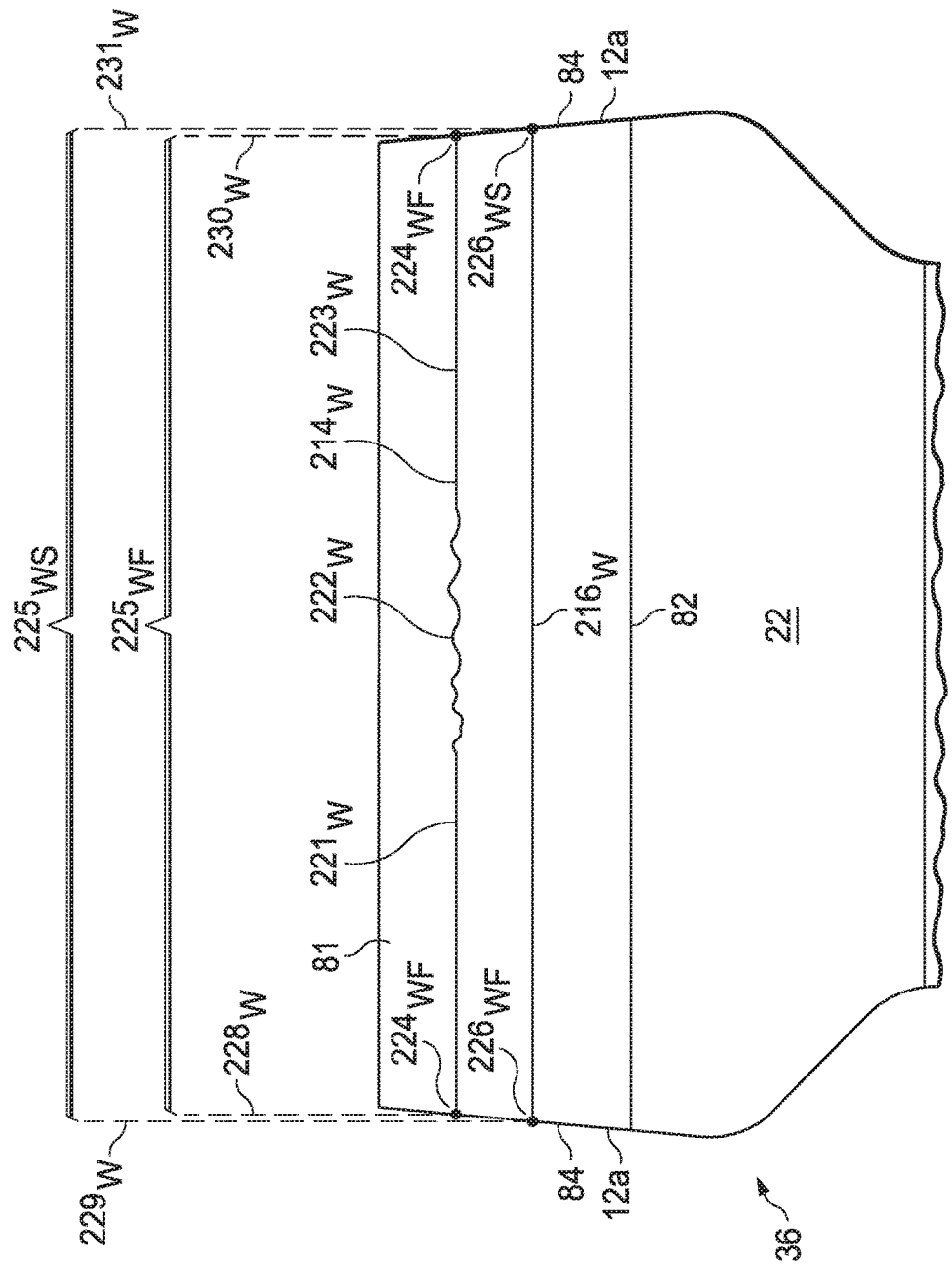
FIG. 12 is a schematic plan view of an exemplary embodiment of a waist gasketing element as detailed herein. The waist gasketing element is shown in a flat, uncontracted state.

In an embodiment, an elastic member $210_w$ can be joined to the chassis and/or to the waist gasketing element 81 at both a contraction starting point and a contraction ending point, forming a contraction region 225 therebetween. In one nonlimiting example shown in FIG. 12, the longitudinal edges 84 of the waist gasketing element 81 are coterminous with the longitudinal edges of the chassis in the waist region 12a, 12b. (FIG. 12 schematically depicts the first waist region but is equally applicable to embodiments where the second waist region comprises an elasticized region $200_w$.) In a further embodiment, the lateral length of the contraction region $225_{WF}$ of a first waist elastic member $214_w$ may be different than the length of the contraction region $225_{WS}$ of a second waist elastic member $216_w$. The contraction starting points $224_{FW}$, $224_{SW}$ of the first and second waist elastic members $214_w$, $216_w$ may be disposed on different longitudinal axes $228_W$, $229_W$. Likewise, the contraction ending points $226_{FW}$, $226_{SW}$ may be disposed on different longitudinal axes $230_W$, $231_W$. Additional discussion of the contraction starting and ending points is included in the Elasticized Region section above.

Returning to FIG. 11, the first waist region 36 and/or second waist region 38 may comprise an elasticized region $200_w$ having an array 240 of waist elastic members $210_w$. In one embodiment, the first waist region 36 comprises a first waist elasticized region $200_{w1}$ comprising a first waist elastic member $214_w$ and a second waist elastic member $216_w$. The first waist elastic member $214_w$ may be disposed between (i) the waist edge 13 and (ii) the second waist elastic member $216_w$. In some embodiments, the first waist elastic member $214_w$ is adjacent to the second waist elastic member $216_w$. In one nonlimiting example, the first and second waist elastic members $214_w$, $216_w$ are disposed a longitudinal distance, $L_{w1-w2}$, apart from about 3.5 mm to about 10 mm.

In another embodiment, the second waist region 38 comprises a second waist elasticized region $200_{W2}$ comprising a first back waist elastic member $215_w$ and a second back waist elastic member $217_w$. The first back waist elastic member $215_w$ may be disposed between (i) the waist edge 14 and (ii) the second back waist elastic member $217_w$. In some embodiments, the first back waist elastic member $215_w$ is adjacent to the second back waist elastic member $217_w$. In one nonlimiting example, the first and second back waist elastic members $215_w$, $217_w$ are disposed a longitudinal distance, $L_{w3-w4}$, apart of from about 3.5 mm to about 10 mm.

In another embodiment, waist elastic members $210_w$ in the array 240 may be differentially strained as discussed in more detail in the Elasticized Region section above. In one embodiment, the first waist elastic member $214_w$ comprises a first waist elastic strain, $\varepsilon_{1w}$, and the second waist elastic member $216_w$ comprises a second waist elastic strain, $\varepsilon_{2w}$. The first waist elastic strain, $\varepsilon_{1w}$, may be different than the second waist elastic strain, $\varepsilon_{2w}$. In one nonlimiting example, the second waist elastic strain, $\varepsilon_{2w}$, is greater than the first waist elastic strain, $\varepsilon_{1w}$. In another embodiment, the first back waist elastic member $215_w$ comprises a first back waist elastic strain, $\varepsilon_{w3}$, and the second back waist elastic member $217_w$ comprises a second back waist elastic strain, $\varepsilon_{w4}$. The first back waist strain, $\varepsilon_{w3}$, may be different than the second back waist elastic strain, $\varepsilon_{w4}$. In one nonlimiting example, the second back waist strain, $\varepsilon_{w4}$, is greater than the first back waist strain, $\varepsilon_{w3}$.

In a further embodiment, the waist elasticized region $200_w$ comprises adjacent waist elastic members joined to the waist gasketing element 81 differently. In such embodiment, the first waist elastic member $214_w$ may be adjacent to the second waist elastic member $216_w$ and/or the first back waist elastic member $215_w$ may be adjacent to the second back waist elastic member $217_w$. In one nonlimiting example, the first waist elastic member $214_w$ is joined to the waist gasketing element 81 at first and second front waist attachment intervals $221_{w1}$, $223_{w1}$. The attachment intervals $221_{w1}$, $223_{w1}$ are separated by an unattached span $222_{w1}$. The first waist attachment interval $221_{w1}$ can be disposed proximate to or touch a longitudinal edge 12, and the second waist attachment interval $223_{w1}$ can be disposed proximate to or touch the opposite longitudinal edge 12 as shown in FIGS. 11-12. In such example, the second waist elastic member $216_w$ is continuously joined to the waist gasketing element 81. It is also contemplated that the second waist elastic member $214_w$ may be joined at two attachment intervals 219 separated by an unattached span 222 and the first waist elastic member $214_w$ may be continuously joined to the waist gasketing element 81 with the attachment zone $218_{w1}$.

In another nonlimiting example, the first back waist elastic member $215_w$ is joined to the waist gasketing element 81 at first back and second back waist attachment intervals $221_{w3}$, $223_{w3}$. The first back waist attachment interval $221_{w3}$ can be disposed proximate to or touch a longitudinal edge 12, and the second back waist attachment interval $223_{w3}$ can be disposed proximate to or touch the opposite longitudinal edge 12 as shown in FIGS. 11-12. In such example, the second back waist elastic member $217_w$ is continuously joined to the waist gasketing element 81. The elastic members $210_w$ may be joined to the waist gasketing element 81 by one or more adhesive bonds 212, and the unattached span $222_{w3}$ may comprise an unglued span $222_{w3}$. It is also contemplated that the second back waist elastic member $217_w$ may be joined at two attachment intervals 219 separated by an unattached span 222 and the first back waist elastic member $215_w$ may be continuously joined to the waist gasketing element 81 with the attachment zone $218_{w2}$.

Elasticized regions in the first and/or the second waist region may comprise additional waist elastic members $210_w$. In an embodiment, the waist elasticized region $200_w$ may comprise at least two waist elastic members $210_w$, at least three waist elastic members $210_w$, at least four elastic members $210_w$, at least five elastic members $210_w$, at least six waist elastic members $210_w$, at least seven waist elastic members $210_w$, at least eight waist elastic members $210_w$, at least nine waist elastic members $210_w$, at least ten waist elastic members $210_w$, at least eleven waist elastic members $210_w$, or at least twelve waist elastic members $210_w$.

In an embodiment, any waist elastic members $210_w$ in the first waist region 36 and/or any waist elastic members $210_w$ in the second waist region 38 may be differentially strained. Further, strain levels in the first waist region 36 may be the same as or different than strain levels in the second waist region 38. In a further embodiment, the first waist elastic strain, $\varepsilon_{W1}$, is different than the first back waist elastic strain, $\varepsilon_{W3}$. In one nonlimiting example, the first waist elastic strain, $\varepsilon_{W1}$, is greater than the first back waist elastic strain, $\varepsilon_{W3}$. In another nonlimiting example, the first waist elastic strain, $\varepsilon_{W1}$, is less than the first back waist elastic strain, $\varepsilon_{W3}$. In another embodiment, the second waist strain, $\varepsilon_{W2}$, is different than the second back waist elastic strain, $\varepsilon_{4W}$. In one nonlimiting example, the second waist strain, $\varepsilon_{W2}$, is greater than the second back waist elastic strain, $\varepsilon_{4W}$. In another nonlimiting example, the second waist strain, $\varepsilon_{W2}$, is less than the second back waist elastic strain, $\varepsilon_{4W}$.

In still another embodiment, any adjacent elastic members $210_w$ in the first waist region 36 and/or any adjacent elastic members $210_w$ in the second waist region 38 may be differently joined to the waist gasketing element 81 in the respective attachment zones $218_{w1}$, $218_{w2}$. In a further embodiment, adjacent elastic members $210_w$ in the first waist region 36 may be attached differently than adjacent elastics $210_w$ in the second waist region 38. In one nonlimiting example, the first waist elastic member $214_W$ is joined to the waist gasketing element 81 in first region attachment pattern $220_{W1}$ and the first back waist elastic member $215_W$ is joined to the waist gasketing element 81 in a second region attachment pattern $220_{W3}$. The first region attachment pattern $220_{W1}$ may be different from the second region attachment pattern $220_{W3}$. Alternatively, the first region attachment pattern $220_{W1}$ may be the same as the second region attachment pattern $220_{W3}$. The attachment patterns $220_{W1}$, $220_{W3}$ may be formed by pattern slot coating.

Figure 13A:
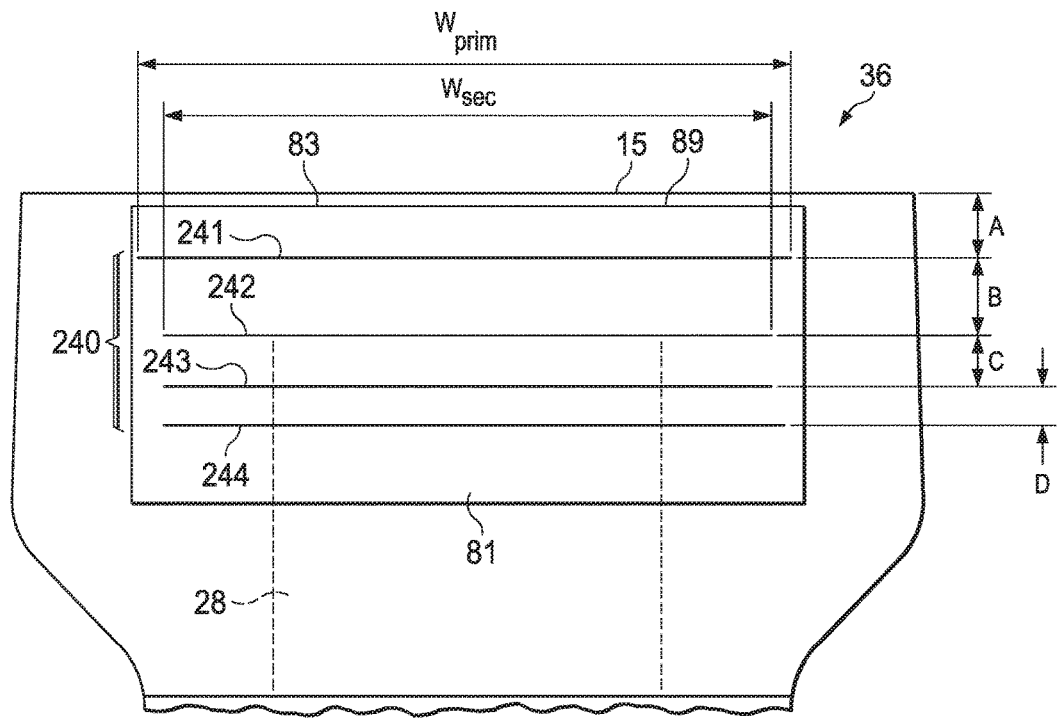
FIGS. 13A-13D are schematic plan views of exemplary embodiments of waist gasketing elements as detailed herein. The waist gasketing elements are shown in a flat, uncontracted state.
Figure 13B:
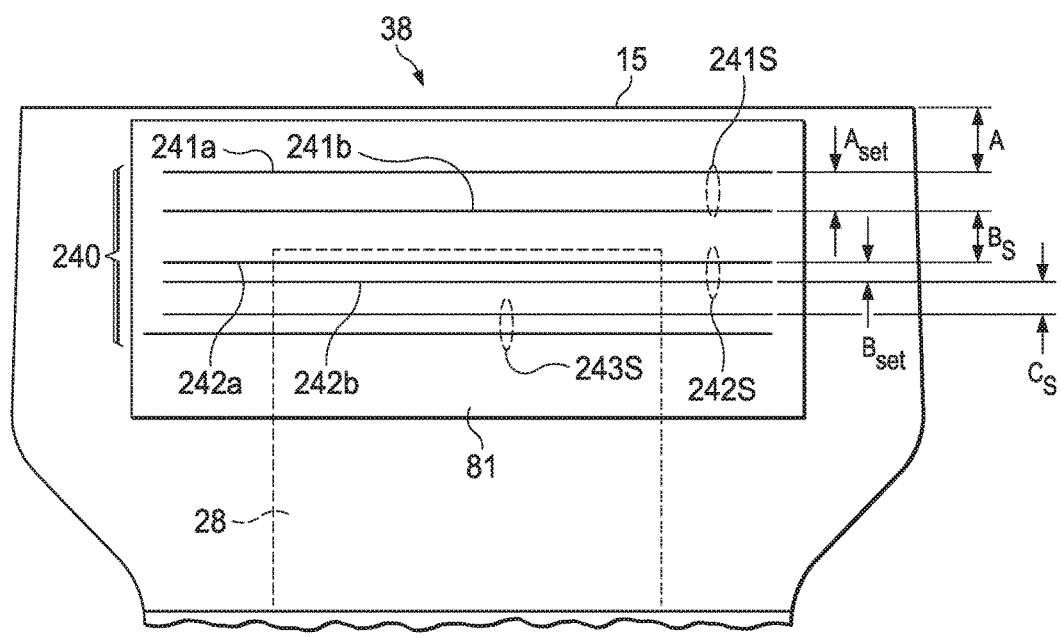

The waist elasticized region $200_w$ is used to the contract the article in the waist region 36, 38 to enhance fit about the wearer. While not intending to be bound by theory, the contractive forces in the elastic members $210_w$ cause the contraction of the portion of the article 20 where the elastic members $210_w$ are disposed. However, identical elastic members $210_w$ (e.g., size, decitex, etc.) under identical strain levels disposed in the elasticized region $200_w$ can each provide a different level of contraction on surrounding materials depending on their respective locations and the stiffness and/or rigidity of the materials to which the elastics $210_w$ are attached or are otherwise in close proximity. By way of example, where the core 28 is disposed inboard of the waist edge (as shown in FIGS. 13A and 13B), an elastic member $210_w$ disposed over the core 28 (and other layers joined to the core 28) and applied at a given condition may exhibit less contraction than an identical elastic member $210_w$ applied at the same given condition but disposed within the topsheet and backsheet laminate alone. Likewise, an elastic member $210_w$ disposed further from the waist edge (and thus being surrounded by more material) will exhibit less contraction than an identical elastic member $210_w$ disposed closer to the waist edge. As a result of the different contraction in individual elastic members $210_w$, the respective surrounding materials (i.e., the materials immediately surrounding each elastic member $210_w$ whether above, below or adjacent) will also experience a difference in contraction. Essentially, the rigid, stiffer materials counteract an elastic member's $210_w$ contractive force, causing the force equilibrium to be reached at a lower contraction level than if the elastic member $210_w$ were placed over less stiff, more flexible materials.

The contraction causes the waist region where the elasticized region $200_w$ is disposed to bend towards the waist edge—that is, in a convex manner with respect to the less stiff, more bendable area, which is closer to the waist edge. The convex shape precludes the article from lying flat and/or causes the lateral edge of the article to curve inwards while lying flat. Each issue makes it harder to find fasteners on the article because (i) the fasteners 46 are disposed at an angle as opposed to linearly, (ii) the lateral distance of the waist region is shorter and the fasteners 46 are therefore less visible when the article is disposed around or under the wearer during application, and (iii) the raising and contraction of the material may cause the waist region to bend even further inward when the wearer is laid upon the article, hiding the fastening system 44. Moreover, the fasteners 46 are not as easily secured to the intended landing zones 47 due to the undesired curvature of the waist region in the elasticized region $200_w$.

The inventors have found that the tendency to bend is reduced or eliminated by increasing the actual contractive force of elastic members $210_w$ disposed inboard (i.e., closer to the core 28) relative to the actual contractive force of the elastic members $210_w$ disposed outboard (i.e., closer to the waist edge). The difference in force between inboard and outboard elastics may be determined using the Tensile Test Method for Force Differential of Waist Gasketing Element as detailed herein. Nonlimiting examples of ways by which the elastic force differential is created include greater applied strain levels on the inboard elastic member(s), greater decitex of the inboard elastic member(s), greater diameter of the inboard elastic member(s), different base materials between inboard and outboard elastic members (i.e., such that an inboard elastic member has a higher Young's modulus or stiffness), more elastic members disposed inboard than outboard, and closer longitudinal spacing between adjacent elastic members $210_w$ that are inboard versus elastic members disposed more outboard. In some embodiments, the waist gasket element may have a Force Ratio of at least about 1.1, or from about 1.1 to about 1.5, reciting every 0.01 increment therein.

In one embodiment shown in FIG. 13A, the elasticized waist region $200_w$ comprises a longitudinal array of waist elastic members 240. In a contracted state (i.e., when the waist gasketing element is not being stretched), an inner elastic member 242, 243 or 244 is substantially equal in lateral width or is shorter (less wide) than the outermost elastic member 241. (FIG. 13A schematically depicts an elasticized waist region). Stated differently, a primary outboard elastic member 241 may comprise a primary lateral width, $W_{prim}$, and a secondary inboard elastic member 242 may comprise a secondary lateral width, $W_{sec}$. Said widths may be measured by projection against the lateral centerline 110. The primary lateral width, $W_{prim}$, may be greater than or equal to the secondary lateral width, $W_{sec}$. In this way, the waist region can be made to remain substantially flat during application of the article 20.

In another embodiment, the array 240 comprises a primary waist elastic member 241 comprising a primary force, FP, and a secondary waist elastic member 242 comprising a secondary force, FS. The secondary waist member is disposed inboard of the primary waist member 241. The secondary FS may be greater than the primary force FP as determined by the Tensile Test Method for Force Differential of Waist Gasketing Element as detailed herein. In one nonlimiting example, the primary waist elastic member 241 comprises a primary decitex, DP, and the secondary elastic member 242 comprises a secondary decitex, DS. The secondary decitex, DS, may be greater than the primary decitex, DP. In another nonlimiting example, the primary waist elastic member 241 comprises a primary diameter, dP, and the secondary elastic member 242 comprises a secondary diameter, dS. The secondary diameter, dS, may be greater than the primary diameter, dP. In yet another nonlimiting example, the primary waist elastic member 241 comprises a primary waist elastic strain, $\varepsilon_{wp}$, and the secondary elastic member 242 comprises a secondary waist elastic strain, $\varepsilon_{ws}$. Strain may be determined in accordance with the Strain Test Method herein. The secondary waist elastic strain, $\varepsilon_{ws}$, may be greater than the primary waist elastic strain, $\varepsilon_{wp}$. It is believed that any of these examples can result in an article 20 having higher contractive elastic force on an inboard elastic 242 resulting in greater contraction of the area immediately surrounding the inboard elastic member 242 than if the elastic members 241, 242 comprised the same levels of the above-referenced factors.

In still another nonlimiting example, the array 240 may comprise additional elastic members $210_w$ including a tertiary elastic member 243 disposed inboard of the secondary elastic member 242 and a quaternary elastic member 244 disposed inboard of the tertiary elastic member 243. The tertiary elastic member 243 may comprise a tertiary force FT that may be greater than the primary force FP or greater than the secondary force FS. In one nonlimiting example, the tertiary member 243 may comprise a tertiary waist strain, $\varepsilon_{wt}$, that is greater than the secondary waist strain, $\varepsilon_{ws}$ and/or greater than the primary waist strain, $\varepsilon_{wp}$. Further, the tertiary member 243 may comprise a tertiary decitex, DT, that may be greater than the secondary decitex, DS or greater than the primary decitex, DP. In another nonlimiting example, the tertiary member 243 may comprise a tertiary diameter, dT, that may be greater than the secondary diameter, dS, or greater than the primary diameter, dP. The quaternary elastic member 244 may comprise a quaternary force, FQ, that may be greater than the primary force, FP, or greater than the secondary force, FS, or greater than the tertiary force, FT. Further, the quaternary elastic member 244 may comprise a quaternary waist strain, $\varepsilon_{wq}$, that may be greater than the primary waist strain, $\varepsilon_{wp}$, or greater than the secondary waist strain, $\varepsilon_{ws}$, or greater than the tertiary waist strain, $\varepsilon_{wt}$. The quaternary member 244 may comprise a quaternary decitex, DQ, that may be greater than the primary decitex, DP, or greater than the secondary decitex, DS, or greater than the tertiary decitex, DT. In another nonlimiting example, the quaternary member 244 may comprise a quaternary diameter, dQ, that may be greater than the secondary diameter, dS, or greater than the primary diameter, dP, or greater than the tertiary diameter, dT.

In a further embodiment, the primary waist elastic member 241 may be disposed a minimum longitudinal distance A from the waist edge 13, 14 or from outboard edge 83 of the waist gasketing element 81. In one nonlimiting example, the minimum longitudinal distance A is at least about 3 mm and the edge comprises a folded edge 15, 89. The secondary waist elastic member 242 may be disposed a minimum longitudinal distance B from the primary waist elastic member 241. The tertiary elastic member 243 may be disposed a minimum longitudinal distance C from the secondary waist elastic member 242, and B may be greater than C. In this way, the contraction inboard is greater than the contraction outboard. The quaternary elastic member 244 may be disposed a minimum longitudinal distance D from the tertiary waist elastic member 243, and C may be greater than D.

It is believed that the above embodiments (relating to force, strain, diameter, decitex, spacing) can result in an increase in the contraction of the inboard portion of the elasticized waist region $200_w$ more than would be otherwise achieved without making the above-referenced provisions. All embodiments are contemplated that can increase the ability of the inboard portion of the elasticized region 200 to contract at the same or higher level than the outboard portion despite the relative stiffer materials in the inboard portion and the tendency of those relatively stiffer materials to resist contraction. Other nonlimiting examples include weakening the materials in or near the inboard portion, using additional materials to increase contractive forces of the elastic members (such as elasticized nonwovens, films) in the inboard portion, corrugating materials near or in the inboard portion, removing materials in the inboard portion, and combinations thereof. All of these embodiments aim to achieve the goal of reducing the convex curvature toward the waist edge of the article 20, and therefore allowing the elasticized region to lay flat.

The same principles may be applied to a set of elastic members (i.e., one or more elastic members, or at least two elastic members) as illustrated in FIG. 13B. In other words, in the contracted state, an outboard set 241S can comprise substantially the same lateral width or a greater lateral width than an inboard set of elastic members 242S. Likewise, the array 240 may comprise a primary set of elastic members 241S having an aggregate primary force $\Sigma FP$, defined as the sum of the force values for each elastic member in the primary set 241S. The array 240 may further comprise a secondary set of elastic members 242S having an aggregate secondary force $\Sigma FS$, defined as the sum of the force values for each elastic member in the secondary set 242S. The aggregate secondary force $\Sigma FS$ may be greater than the aggregate primary force $\Sigma FP$ as determined by the Tensile Test Method for Force Differential of Waist Gasketing Element herein. In some embodiments, the Force Ratio (as determined by the Tensile Test Method for Force Differential) may be at least about 1.1, or from about 1.1 to about 1.5, reciting every 0.01 increment therein. A greater aggregate force may be achieved by having (i) an aggregate secondary elastic strain $\Sigma\varepsilon_{ws}$ that is greater than the aggregate primary elastic strain, (ii) an aggregate secondary decitex $\Sigma DS$ that is greater than the aggregate primary decitex, $\Sigma DP$, (iii) an aggregate secondary diameter $\Sigma dS$ that is greater than the aggregate primary diameter $\Sigma dP$, (iv) a greater number of secondary elastic members 242 in the secondary set 242S than primary elastic members 241 in the primary set 241S, (v) closer longitudinal spacing between adjacent elastic members 242 in the secondary set than the longitudinal spacing between adjacent primary elastic members 241 in the primary set 241S and/or (vi) any of the other embodiments taught with reference to primary 241 and secondary 242 elastic members above.

In a further nonlimiting example, the array 240 may include additional elastic members $210_w$ including a tertiary set of elastic members 243S. The tertiary set 243S may comprise an aggregate tertiary force $\Sigma FT$ greater than the aggregate primary force, $\Sigma FP$, or greater than the aggregate secondary force, $\Sigma FS$. The force differential may be created in accordance with the teachings herein and other known methods. The force differential may be determined in accordance with the Tensile Test Method for Force Differential of Waist Gasketing Element herein.

Further, the minimum longitudinal distance between sets may be such that inboard sets are spaced closer together than outboard sets (i.e., the minimum longitudinal distance between sets being the minimum longitudinal distance between adjacent elastic members belonging to different sets). In one nonlimiting example, the primary set 241S and secondary set 242S are separated by a minimum longitudinal distance of $B_s$, and the secondary set 242S and tertiary set 243S are separated by a minimum longitudinal distance $C_s$. In such example, $B_s$ may be greater $C_s$. In another nonlimiting example, adjacent elastics 241a, 241b within the primary set 241S are separated by a primary minimum longitudinal distance $A_{set}$ and adjacent elastic members 242a, 242b within the secondary set 242S are separated by a secondary minimum longitudinal distance $B_{set}$. $A_{set}$ may be greater than $B_{set}$. In yet another nonlimiting example, the secondary set 242S comprises a greater number of elastic members $210_w$ than the first set 241S. The primary set 241S may comprise n primary elastic members 241, and the secondary set may comprise at least n+1 secondary elastic members 242.

Figure 13C:
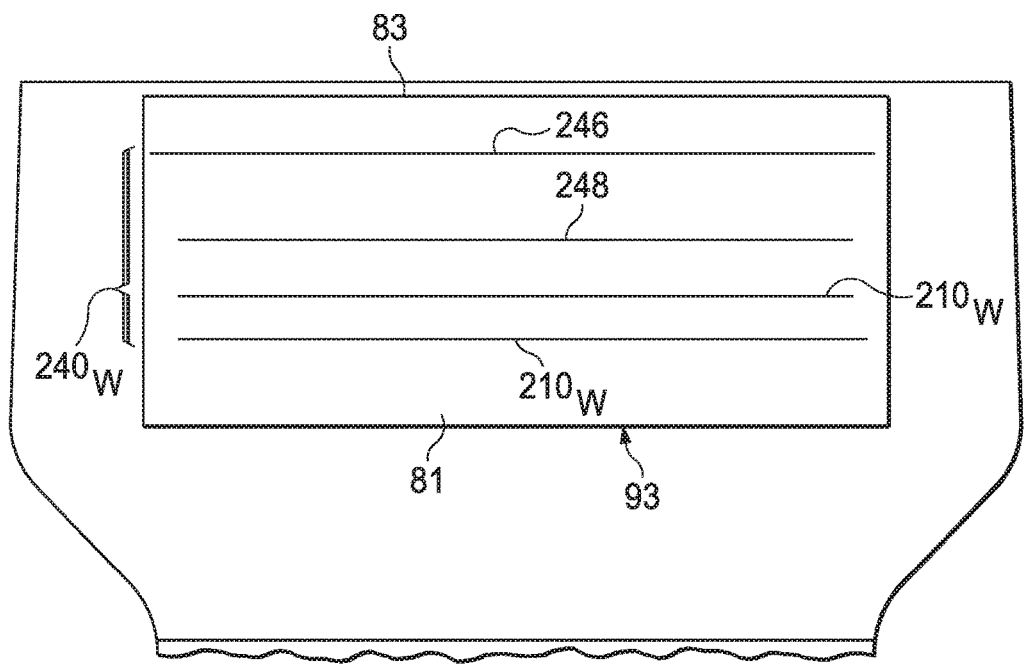
Figure 13D:
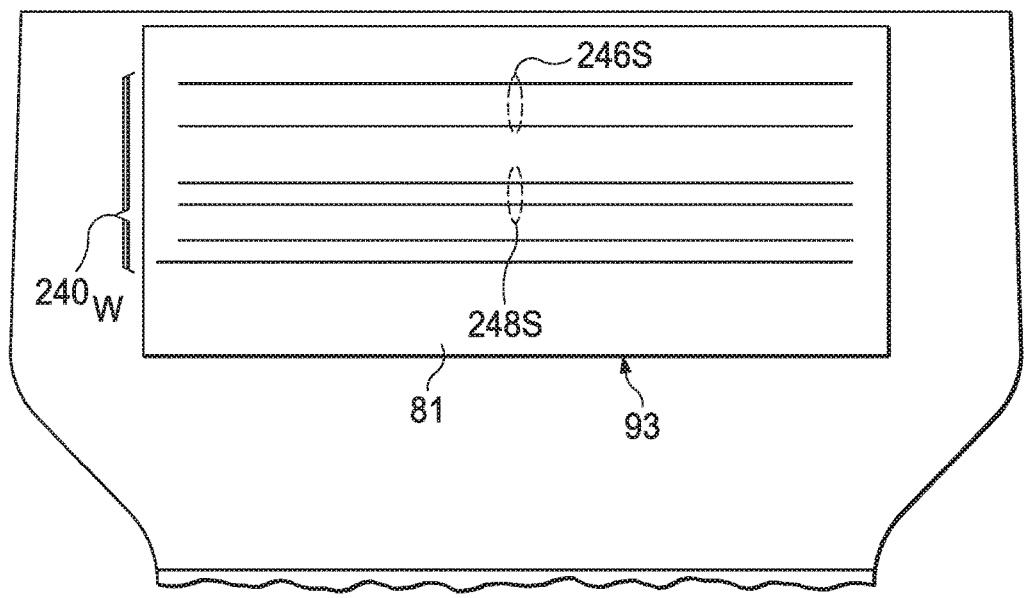

In another embodiment, the elasticized region $200_w$ is disposed in a waist gasketing element 81 that comprises a pocket 93 as shown in FIGS. 13C and 13D. An array 240 may include a first outboard pocket elastic member 246 disposed inboard of the outboard lateral edge 83 and having a first outboard pocket force, FOP. The array may further comprise a second inboard pocket elastic member 248, disposed inboard of the first outboard pocket elastic 246 and having a second inboard pocket force SIP. The second inboard pocket force, SIP, may be greater than the first outboard pocket force FOP. In this way, a greater amount of void volume may be created. The difference in forces can be determined by the Tensile Test Method for Force Differential herein. In one nonlimiting example, the Force Ratio in a waist element having a pocket 93 as determined by the Tensile Test Method for Force Differential herein is at least about 1.1, or from about 1.1 to about 1.5, reciting each 0.01 increment therein. In a further nonlimiting example, the first outboard pocket elastic 246 comprises an outboard pocket elastic decitex, DOP, and the second inboard pocket elastic 248 comprises an inboard pocket elastic decitex, DIP. The second inboard pocket elastic decitex, DIP, may be greater than the first outboard pocket elastic decitex, DOP. In another nonlimiting example, the first outboard pocket elastic 246 comprises an outboard pocket strain, $\varepsilon_{wop}$, and the secondary inboard pocket elastic 248 comprises an inboard pocket strain, $\varepsilon_{wip}$. Again, strain may be determined by the Strain Test Method herein. The inboard pocket strain, $\varepsilon_{wip}$, may be greater than the outboard pocket strain, $\varepsilon_{wop}$. As explained in detail above and illustrated in FIG. 13C, the array 240w may comprise additional elastic members $210_w$ which may comprise differential spacing such that inboard elastic members $210_w$ are more closely spaced than outboard elastic members. Likewise, an embodiment may include sets of elastics (as depicted in FIG. 13D) that vary by aggregate force, including but not limited to aggregate strain, aggregate decitex, aggregate diameter, the number of elastic members in a set, longitudinal spacing and/or other nonlimiting examples described herein. In embodiments where the waist gasketing element 81 comprises a pocket 93, it is believed that a higher inboard contraction level can be achieved via equal inboard and outboard forces because the unattached portion of the pocket (described above) has less surrounding material counteracting the contraction of elastic member(s) 248 disposed closer to the unattached portion. Therefore, under the same actual contractive force, the inboard pocket elastic member(s) 248 can contract more than the outboard elastic member(s) 246. However, by creating an even higher inboard elastic force using the teachings and embodiments herein, the pocket 93 may comprise greater void volume for the capture and containment of exudates.

Figure 14A:
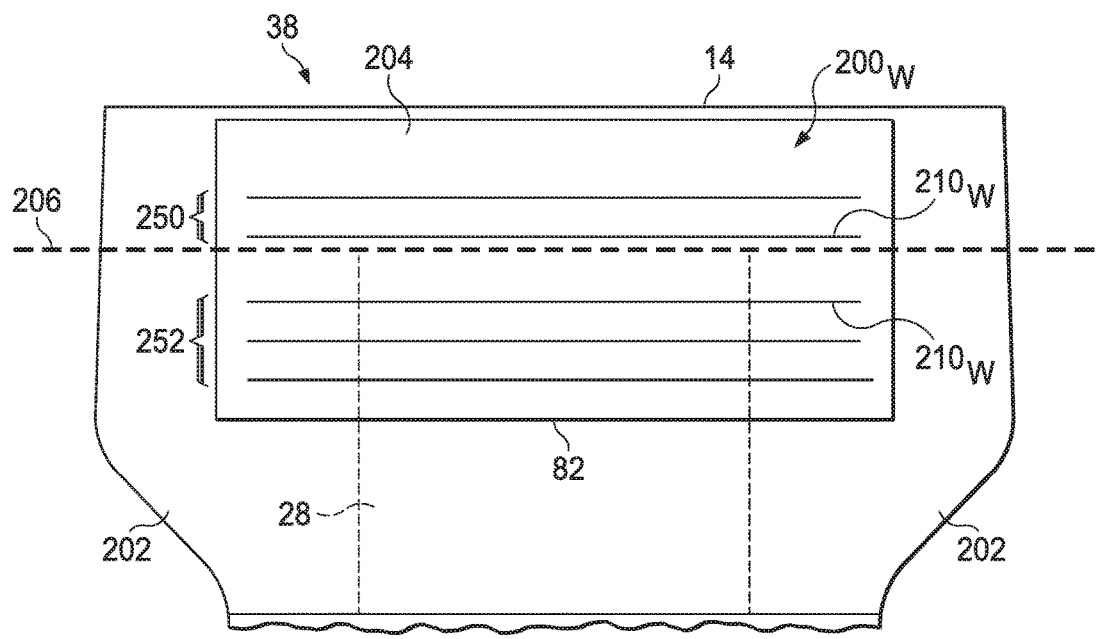
FIGS. 14A-14B are schematic plan views of exemplary embodiments of waist gasketing elements as detailed herein. The waist gasketing elements are shown in a flat, uncontracted state.
Figure 14B:
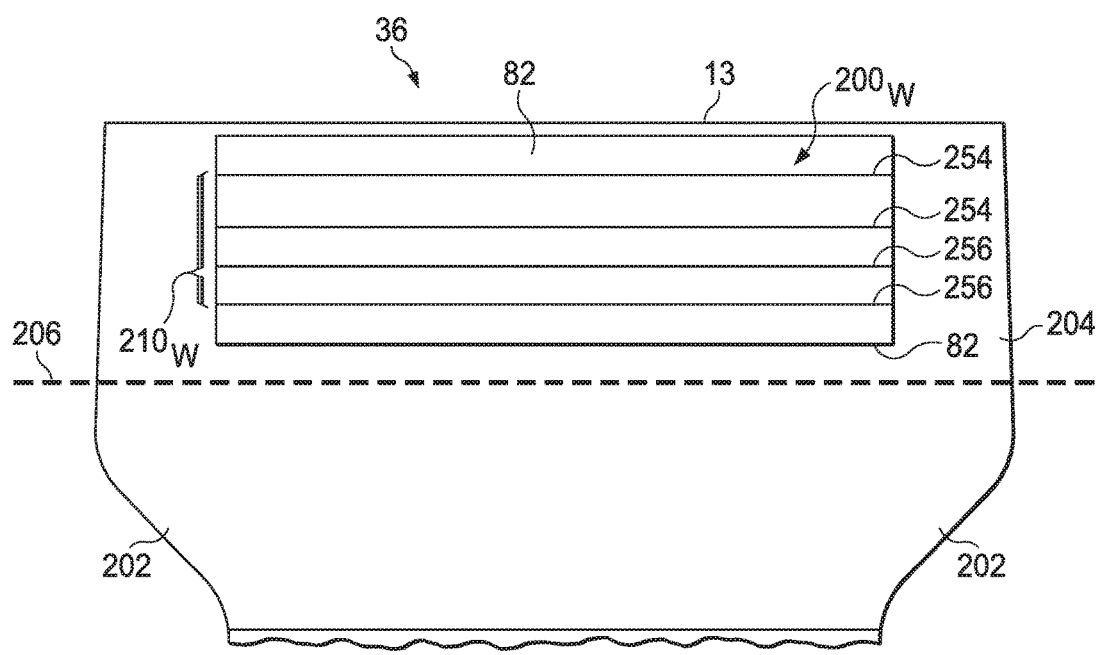

Turning to FIGS. 14A and 14B, the article 20 may comprise a lateral bending line 206 in a waist region 36, 38. The lateral bending line 206 is the lateral line in the article 20 where the article tends to bend in the waist region 36, 38 once an elasticized waist region $200_w$ is included; the article 20 will bend in a z-direction bending line (a line perpendicular to the majority of the surface of article 20 and intersects the lateral bending line 206) and/or the article will bend upwards towards the edge 13, 14 of the respective waist region 36, 38. The lateral bending line 206 is determined by finding the lateral line where an elastic member $210_w$ exhibits a change in contraction of at least 8%. The lateral bending line 206 separates a rigid region 202 and a bendable region 204. In one nonlimiting embodiment, the lateral bending line 206 is coterminous with the lateral edge of the core 28, where the core 28 is disposed in the rigid region 202. An elasticized waist region $200_w$ may be disposed between the waist edge 13, 14 and the lateral bending line 206 as shown in FIG. 14B.

Alternatively, the elasticized waist region $200_w$ may overlay by the lateral bending line 206 as shown in FIG. 14A. When elastic members $210_w$ are symmetrically spaced on either side of the bending line 206 and exhibit the same actual contractive force F, the article 20 will tend to bend in a generally convex manner about the bendable region 204. This is because the elastic members $210_w$ in the bendable region 204 can contract farther before reaching the force equilibrium with the surrounding materials than in the more rigid region 202 (i.e., the force has a greater effect on the less stiff, more bendable materials in the bendable region 204). Stated differently, the elastic members $210_w$ in the rigid region 202 will be subject to a dampening effect, c, which dampens said elastic member's actual contractive force. The inventors have found that adjusting the forces of the waist elastic members $210_w$ will reduce the tendency of the waist gasketing element 81 to bend. The moment of force is defined by the equation:

$$\text{Moment}_i = r_i \times F_i c_i$$

where:
moment$_i$ is the moment of force for a waist elastic member $210_i$;
$c_i$ is the dampening effect on actual contractive force of waist elastic member $210i$;
$r_i$ is the perpendicular distance between $F_i$ and the bending line 206; and
$F_i$ is the actual contractive force of the waist elastic member $210i$.

The skilled person will recognize that elastic members 210w disposed in a rigid region 202 will exhibit a dampening coefficient, c, of less than 1. The actual value of the dampening coefficient can be empirically determined by the skilled person. Likewise, the skilled person will recognize that elastic members $210_w$ disposed in a bendable region 204 will exhibit a dampening coefficient, c, that is equal to 1 (i.e., there is no dampening effect). Further, the skilled person will recognize that in the context of disposable absorbent articles, changes in force will have more of an effect on the moment than changes in radius. This is because the area within the elasticized region $200_w$ is generally limited and only permits small changes in radius.

The aggregate moment of force is the sum of the moments of force for the individual elastic members in a given area (e.g., outboard of the line 206, inboard of the line 206). In some embodiments, the aggregate moment of force of elastic members in a given portion of the elasticized region may be greater than aggregate moment of elastic members in another portion in order to compensate for the effect of surrounding materials on the elastic members' contractive forces. Said differently, when the inboard and outboard portions of an elasticized region $200_w$ contract the same amount, the summation of both the contractive forces and the compression resisting forces (in the material) in the outboard portion should counterbalance the summation of both the contractive forces and the compression resisting forces in the inboard portion (i.e., the sums should zero out). Adjusting the aggregate moments of force may achieve this state.

In one nonlimiting example, where the elasticized region $200_w$ is disposed between the bending line and the waist edge as shown in FIG. 14B, the tendency to bend is reduced or eliminated by ensuring that the aggregate moment of force of waist elastic members 256 closer to the bending line 206 is greater than the aggregate moment of force of waist elastic members 254 closer to the waist edge in the region in which the elasticized region is disposed (i.e., the first waist edge 13 if the elasticized region is disposed in the first waist region 36, the second waist edge 14 if the elasticized region is in the second waist region 38). A greater aggregate moment of force may be achieved by a greater aggregate force and/or a greater aggregate radius. As taught above, the aggregate force ΣFaxis of the inboard elastic members 256 closer to the bending line 206 may be greater than the aggregate force ΣFedge of elastic members closer to the waist edge by (i) a greater aggregate inboard strain than aggregate outboard strain, (ii) a greater aggregate inboard decitex than aggregate outboard decitex, (iii) a greater aggregate inboard diameter than aggregate outboard diameter, (iv) a greater number of elastic members $210_w$ in the inboard set 256 than in the outboard set 254, (iv) closer longitudinal spacing between adjacent inboard elastic members 256 than the longitudinal spacing between adjacent outboard elastic members 254, and/or (v) any other nonlimiting examples disclosed herein. Differences in force may be determined by the Tensile Test Method for Force Differential herein. In some embodiments, the Force Ratio created by inboard elastic members and outboard elastic members is at least about 1.1, or from about 1.1 to about 1.5, reciting each 0.01 increment therein.

In another nonlimiting example, where the elasticized region $200_w$ overlays the bending line 206 as shown in FIG. 14A, the tendency to bend is reduced or eliminated by ensuring the aggregate moment of force, $\Sigma M_{in}$, of the waist elastic members 252 disposed inboard of the bending line 206 is greater than the aggregate moment of force, $\Sigma M_{out}$, of the waist elastic members 250 disposed outboard of the bending line 206.

In a further nonlimiting example, a primary outboard set of waist elastic members 250 is disposed outboard of the bending line 206. The primary outboard set of waist elastic members 250 comprises one or more elastic members $210_w$, or at least two elastic members $210_w$, disposed between the waist edge and the bending line 206. The primary set of outboard waist elastic members 250 comprises a primary aggregate moment of force ΣMp, which is the sum of the moments of force for each elastic member $210_w$ in the set 250. The elasticized region $200_w$ may further comprise a secondary inboard set of elastic members 252 disposed inboard of the bending line 206. Where the elasticized region $200_w$ is disposed in a waist gasketing element 81, the secondary inboard set of waist elastic members 252 is disposed between the bending line 206 and the inboard lateral edge 82 of the element 81. The secondary set of inboard waist elastic members 252 comprises one or more elastic members 210w, or at least two elastic members $210_w$. The secondary inboard set of elastic members 252 also comprises a secondary aggregate moment of force ΣMs, which is the sum of the moments of force for each elastic member in the secondary inboard set 252. The secondary aggregate moment of force ΣMs may be greater than the aggregate primary moment of force, ΣMp. A greater aggregate moment of force may be achieved by a greater aggregate force and/or a greater aggregate radius. As taught above, the aggregate force ΣFin of the secondary set of inboard elastic members 252 may be greater than the aggregate primary outboard force ΣFout by (i) a greater aggregate secondary inboard strain $\Sigma\varepsilon_{inw}$ than aggregate primary outboard strain $\Sigma\varepsilon_{outw}$, (ii) a greater aggregate secondary decitex, ΣDin, than aggregate primary outboard decitex, ΣDout, (iii) a greater aggregate secondary diameter, Σdin, than aggregate primary outboard diameter, Σdout, (iv) a greater number of elastic members $210_w$ in the second inboard set 252 than in the primary outboard set 250, (iv) closer longitudinal spacing between adjacent secondary inboard elastic members 252 than the longitudinal spacing between adjacent primary outboard elastic members 250, and/or (v) any other nonlimiting examples disclosed herein. Differences in force may be determined by the Tensile Test Method for Force Differential herein. In some embodiments, the Force Ratio created by inboard elastic members and outboard elastic members is at least about 1.1, or from about 1.1 to about 1.5, reciting each 0.01 increment therein.

In an embodiment, the waist gasketing element 81 may comprise N-fiber. Exemplary N-fiber material is disclosed in U.S. Pat. App. No. 62/134,622; 62/186,727.

Opacity Strengthening Patch:

In some embodiments of the disposable absorbent articles detailed herein, an opacity strengthening patch 80 may be included as part of the chassis 22. The opacity strengthening patch 80 is an additional layer of material. The opacity strengthening patch 80 may be connected to the leg gasketing system 70, the polymeric film layer 261, and/or the backsheet 26. The opacity strengthening patch 80 may be disposed between the backsheet 26 and leg gasketing system 70 in either the first waist region 36, the second waist region 38, or both the first waist region 36 and the second waist region 38 of the article; the opacity strengthening patch 80 may overlap at least one of the leg gasketing system 70 and/or the polymeric film layer 261 (i.e., inner layer of the backsheet 26). The opacity strengthening patch 80 may be attached to one or both of the leg gasketing system 70 or the polymer film layer using any suitable means such as glue, mechanical bonds, thermal bonds, or the like, so that loads generated during the application process or during wear can be transferred from the lateral edge of the article to the leg gasketing system 70 and/or the polymeric film layer. The opacity strengthening patch is useful in providing the strength needed to prevent the article from extending excessively during application and wearing; it also may provide opacity at the sides and waist to prevent the skin of the user from showing through the article. Thus, the patch 80 may be located at any portion of the chassis 22 where strength and opacity is desirable. Suitable opacity strengthening patches are disclosed in U.S. Pat. App. No. 62/134,622; 62/186,727; Ser. No. 15/074,047.

Construction Materials:

It is recognized that there are many combinations of material lateral tensile properties that could form a substantially suitable force transmission pathway in the waist region or the article without excessive lateral stretch in the waist region, and that the material force pathways may go from the opacity strengthening patch directly into the polymeric film layer or into the polymeric film layer through a variety of other layers in the region immediately outboard the polymeric film layer. These layers may include the topsheet, backsheet nonwoven, cuff, absorbent assembly, leg gasketing system, or any other layer that is located in a region adjacent to the polymeric film layer.

In one embodiment, the material of the leg gasketing system 70 is made from a substantially liquid impervious material. The material may be selected from the group consisting of an SMS nonwoven, SMMS nonwoven material, or a nonwoven component layer comprising "N-fibers".

Various nonwoven fabric webs may comprise spunbond, meltblown, spunbond ("SMS") webs comprising outer layers of spunbond thermoplastics (e.g., polyolefins) and an interior layer of meltblown thermoplastics. In one embodiment of the present invention, the leg gasketing system 70 comprises a nonwoven component layer having fine fibers ("N-fibers") with an average diameter of less than 1 micron (an "N-fiber layer") may be added to, or otherwise incorporated with, other nonwoven component layers to form a nonwoven web of material. In some embodiments, the N-fiber layer may be used to produce a SNS nonwoven web or SMNS nonwoven web, for example. Suitable construction materials, including N-fibers, are disclosed in U.S. Pat. App. No. 62/134,622; 62/186,727; Ser. No. 15/074,047.

Package

Figure 15:
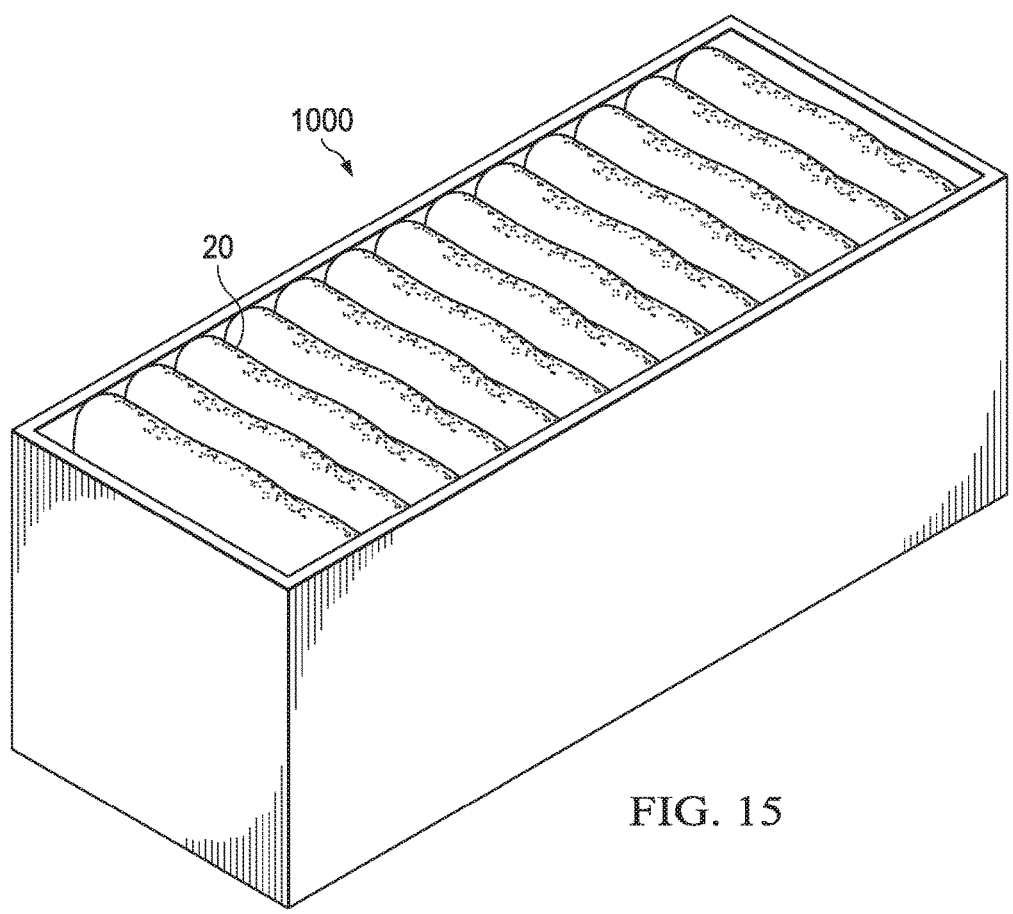
FIG. 15 is a schematic perspective view of a package in accordance with one embodiment of the present invention.

Turning to FIG. 15, a disposable absorbent article 20 having any of the above-disclosed features may be provided in a package 1000 comprising about 5 or more articles 20, or about 8 or more, or about 10 or more articles 20.

Combination of Embodiments

While embodiments are described separately herein for brevity and clarity, combinations of the various embodiments are contemplated and within the scope of the present disclosure. For example, the combination of differently joined and different strained elastic members, where the outermost elastic member comprises an unattached span between two attachment intervals and is disposed at least 3 mm from the edge, would result in an enhancement of various benefits described herein.

Test Methods:

Strain Test Method

Strain is measured individually for each elastic member in a waist gasketing element. Linear measurements are made with a steel ruler traceable to NIST or similar standards organization. All testing is performed in a room controlled at 23° C.±3 C.° and 50%±2% relative humidity.

Open the article and place it, backsheet down, on a lab bench. Identify the waist gasketing element and carefully remove from the article in a non-destructive manner. For example, a minimal amount of cryogenic spray can be applied through the outermost layer of the article to remove the waist gasketing element. Cut two longitudinal lines perpendicular to the waist element lateral edge immediately inboard of the shortest elastic member for both the left and right side of the waist element.

Cut the specimen in the lateral direction, midway between each elastic member, to isolate the individual elastic members within the waist gasketing element. Carefully label each strip to denote its position in the original waist gasketing element (e.g. top to bottom, position 1 through position n).

Submerge a specimen strip in an appropriate solvent, such as tetrahydrofuran, that will dissolve the adhesives but not the nonwovens or elastic member. After the components have separated, remove each component from the solvent and place on a flat bench within a ventilated hood to allow the solvent to dry. Arrange the elastic member on the bench in a substantially linear configuration in a relaxed state and measure and record its length to the nearest 0.1 mm. Likewise, arrange the nonwoven strip flat on the bench, extended to its full dimension without stretching and measure the length to the nearest 0.1 mm. If the elastic member is sandwiched between two nonwovens, measure the length of both nonwoven strips and report the nonwoven length as their average to the nearest 0.1 mm. Calculate the Elastic Member Strain as the [Nonwoven Length (mm)−Elastic Member Length (mm)]/Elastic Member Length (mm)×100 and report to the nearest 0.1%. Repeat for each strip isolated from that waist gasketing element.

The measure is performed for a total of five replicate waist gasketing elements. An average Elastic Member Strain is then calculated for each position (1 through n) and reported to the nearest 0.1%.

Tensile Test Method for Force Differential of Waist Gasketing Element

The tensile properties of an elasticized sample are measured on a constant rate of extension tensile tester with computer interface (a suitable instrument is the MTS Alliance using Testworks 4.0 Software, as available from MTS Systems Corp., Eden Prairie, Minn.) using a load cell for which the forces measured are within 10% to 90% of the limit of the cell. The load cell is calibrated per the vendor instructions prior to testing. Both the movable (upper) and stationary (lower) pneumatic jaws are fitted with rubber faced grips that are 15 mm wide by 8 mm tall. Linear measurements are made with a steel ruler traceable to NIST or similar standards organization. All testing is performed in a room controlled at 23° C.±3 C.° and 50%±2% relative humidity.

Open the article and place it, backsheet down, on a lab bench. Identify the Outboard Lateral Edge and Inboard Lateral Edge of the waist gasketing element. Mark the chassis at the four corners of the waist gasketing element. Carefully remove the waist gasketing element from the article in a non-destructive manner. For example, a minimal amount of cryogenic spray can be applied through the outermost layer of the article to remove the waist gasketing element. Mark the waist gasketing element at both of its longitudinal edges 7.5 mm up from the Inboard Lateral Edge and 7.5 mm down from the Outboard Lateral Edge. Repeat for both the left and right longitudinal edges. After the waist gasketing elements have been removed from the article, they are conditioned at 23° C.±3 C.° and 50%±2% relative humidity two hours prior to testing. In like fashion, prepare three waist gasketing elements from three replicate articles.

Fully extend the back region of the chassis where the waist gasketing element was removed and secure to the bench. Measure the distance between the marks on the chassis corresponding to the Outboard Lateral Edge (OBLE extension) and then the distance corresponding to the Inboard Lateral Edge position (IBLE extension) and record to the nearest 0.1 mm. Subtract 16.0 mm from the OBLE extension to give the Final OBLE extension. Likewise subtract 16.0 mm from the IBLE extension to give the Final IBLE extension.

Take the waist gasketing element and measure the lateral width at the marks closest to the Outboard Lateral Edge (OBLE gage) and the lateral width at the marks closest to the Inboard Lateral Edge (IBLE gage) and record both to the nearest 0.1 mm. Subtract 16.0 mm from the OBLE gage to give the Final OBLE gage. Likewise subtract 16.0 mm from the IBLE gage to give the Final IBLE gage.

Program the tensile tester to perform an extension test. From the original gage move the crosshead at 100 mm/min to the final extension endpoint and then return the crosshead to its original position. Force and extension data are collected at a rate of 100 Hz. The gage length and extension endpoint are entered manually for each specimen and test location.

Set the gage length between grip faces to the Final OBLE Gage and zero the crosshead. Set the final extension equal to the Final OBLE Extension (mm). Insert the specimen into the upper grips, aligning it vertically within the upper and lower jaws. Align the top of the grip face flush with the left longitudinal edge of the specimen and centered at the mark proximal to the Outboard Lateral Edge. Close the upper grips. Insert the specimen into the lower grips with the grip face centered at the mark proximal to the Outboard Lateral Edge and close. The specimen should be under enough tension to eliminate any slack, but less than 0.05 N of force on the load cell. Start the test and collect force and extension data. Remove the specimen and allow to condition for 15 minutes. In like fashion repeat the tensile experiment for the Inboard Lateral Edge using the Final IBLE Gage length and Final IBLE Extension. The analysis is repeated in like fashion for a total of 3 replicate waist gasketing element specimens.

From the paired force (N) vs extension (mm) curves, record the force at the Final OBLE Extension (N) and Final IBLE Extension (N) to the nearest 0.001 N. Calculate the Force Ratio as Force at Final IBLE Extension divided by Force at Final OBLE Extension for each of the 3 replicate specimens and report the arithmetic mean to the nearest 0.001.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article for wearing about the lower torso of a wearer, the disposable absorbent article comprising:
    a first waist region having a first waist edge, a second waist region having a second waist edge, a crotch region disposed between the first and second waist regions; and a first longitudinal edge and a second longitudinal edge; and a longitudinal centerline;
    a chassis comprising a topsheet, a backsheet, and an absorbent core disposed between the topsheet and backsheet; and
    a back ear joined to the chassis in the second waist region;
    wherein the first longitudinal edge, second longitudinal edge, first waist edge and second waist edge define a chassis periphery and the chassis periphery comprises a varying width, $W_v$, the varying width $W_v$ comprising a first maximum width, $W_1$, in the first waist region, a minimum width, $W_{min}$, in the crotch region, and a second maximum width, $W_2$, in the second waist region, wherein $W_1$ is greater than $W_2$ and
    wherein the backsheet comprises a polymeric film layer having a polymeric maximum lateral width, $W_{poly}$, wherein the polymeric maximum lateral width, $W_{poly}$, is less than the minimum width, $W_{min}$.

2. The disposable absorbent article of claim 1 wherein the back ear comprises a highly extensible ear.

3. The disposable absorbent article of claim 1 wherein the backsheet comprises a material perimeter, the material periphery being coterminous with the chassis periphery.

4. The disposable absorbent article of claim 3 wherein the back ear is joined to a garment-facing side of the backsheet.

5. The disposable absorbent article of claim 4 further comprising a fastening system joined to the back ear, the fastening system having an inboard fastening edge wherein the lateral distance, $D_{LE-FE}$, between the inboard fastening edge and one of the first longitudinal edge or the second longitudinal edge along the length of the inboard fastening edge is 0 mm or greater.

6. The disposable absorbent article of claim 3 wherein the back ear is joined to a body-facing side of a layer of the chassis.

7. The disposable absorbent article of claim 1 wherein the first waist edge and/or the second waist edge comprises a edge width, $W_E$, and the edge width, $W_E$, is less than the first maximum width, $W_1$.

8. The disposable absorbent article of claim 1 comprising a first maximum width to minimum width ratio, $W_1:W_{min}$, of from about 1.4 and about 2.7.

9. The disposable absorbent article of claim 1 wherein the first waist region comprises a first maximum width zone and wherein the first longitudinal edge and the second longitudinal edge are continually sloping outside of the first maximum width zone.

10. The disposable absorbent article of claim 1 wherein the first waist region comprises a landing zone disposed a lateral distance of about 2 mm or less from the longitudinal centerline.

11. The disposable absorbent article of claim 1 further comprising a leg gasketing system comprising an outer cuff having an outer cuff edge and an inner cuff.

12. The disposable absorbent article of claim 11 wherein the article comprises two leg gasketing systems disposed along opposite longitudinal edges and a maximum cuff width, $W_{cuff}$, the maximum cuff width, $W_{cuff}$, being the maximum lateral distance between the outer cuff edges of each leg gasketing system, and wherein the $W_{cuff}$ is at least about 10 mm greater than the minimum width, $W_{min}$.

13. A disposable absorbent article for wearing about the lower torso of a wearer, the disposable absorbent article comprising:
   a first waist region having a first waist edge, a second waist region having a second waist edge, a crotch region disposed between the first and second waist regions; and a first longitudinal edge and a second longitudinal edge; and a longitudinal centerline;
   a chassis comprising a topsheet, a backsheet, and an absorbent core disposed between the topsheet and backsheet; wherein the first longitudinal edge, second longitudinal edge, first waist edge and second waist edge define a chassis periphery and the chassis periphery comprises a varying width, $W_v$, the varying width $W_v$ comprising a first maximum width, $W_1$, in the first waist region, a minimum width, $W_{min}$, in the crotch region, and a second maximum width, $W_2$, in the second waist region, wherein $W_1$ is greater than $W_2$; and
   an elasticized component joined to the chassis, and comprising an elasticized region and wherein the elasticized region comprises an attachment zone, a first elastic member, and second elastic member and wherein in the attachment zone:
   the first elastic member is joined to the elasticized component by two attachment intervals separated by an unattached span; and
   the second elastic member is continuously joined to the elasticized component.

14. The disposable absorbent article of claim 13 wherein the elasticized region comprises:
   a first elastic member having a first strain, $\varepsilon_1$; and
   a second elastic member having a second strain, $\varepsilon_2$;
   wherein the first strain, $\varepsilon_1$, is different than the second strain, $\varepsilon_2$.

15. The disposable absorbent article of claim 13 wherein the backsheet comprises a material periphery, the material periphery being coterminous with the chassis periphery.

16. The disposable absorbent article of claim 13 further comprising a back ear joined to the chassis in the second waist region.

17. The disposable absorbent article of claim 13 wherein the backsheet comprises a polymeric film layer having a polymeric maximum lateral width, $W_{poly}$, wherein the polymeric maximum lateral width, $W_{poly}$, is different than the minimum width, $W_{min}$ and less than the first maximum width, $W_1$.

18. The disposable absorbent article of claim 13 wherein the elasticized component comprises a leg gasketing system, a waist gasketing element, or an ear.

19. The disposable absorbent article of claim 18 wherein the elasticized component comprises a waist gasketing element, disposed in the second waist region.

20. The disposable absorbent article of claim 19 wherein the first waist region comprises a landing zone disposed a lateral distance of about 2 mm or less from the longitudinal centerline.

21. A disposable absorbent article for wearing about the lower torso of a wearer, the disposable absorbent article comprising:
   a first waist region having a first waist edge, a second waist region having a second waist edge, a crotch region disposed between the first and second waist regions; and a first longitudinal edge and a second longitudinal edge; and a longitudinal centerline;
   a chassis comprising a topsheet, a backsheet, and an absorbent core disposed between the topsheet and backsheet; and
   a back ear joined to the chassis in the second waist region;
   wherein the first longitudinal edge, second longitudinal edge, first waist edge and second waist edge define a chassis periphery and the chassis periphery comprises a varying width, $W_v$, the varying width $W_v$ comprising a first maximum width, $W_1$, in the first waist region, a minimum width, $W_{min}$, in the crotch region, and a second maximum width, $W_2$, in the second waist region, wherein $W_1$ is greater than $W_2$, and
   wherein the first waist region comprises a landing zone disposed a lateral distance of about 2 mm or less from the longitudinal centerline.

22. The disposable absorbent article of claim 21 wherein the backsheet comprises a polymeric film layer having a polymeric maximum lateral width, $W_{poly}$, wherein the polymeric maximum lateral width, $W_{poly}$, is less than the first maximum width, $W_1$, and the polymeric maximum lateral width, $W_{poly}$, is greater than the minimum width, $W_{min}$.

* * * * *